United States Patent
Bengtsson et al.

(10) Patent No.: US 12,064,464 B2
(45) Date of Patent: Aug. 20, 2024

(54) PLANTARICIN NC8 ALPHA BETA MARKEDLY ENHANCES THE EFFECTS OF ANTIBIOTICS

(71) Applicant: CURENC AB, Linköping (SE)

(72) Inventors: Torbjörn Bengtsson, Linköping (SE); Hazem Khalaf, Örebro (SE)

(73) Assignee: CURENC AB, Linkoping (SE)

( * ) Notice: Subject to any disclaimer, the term of this patent is extended or adjusted under 35 U.S.C. 154(b) by 496 days.

(21) Appl. No.: 17/046,659

(22) PCT Filed: Feb. 20, 2019

(86) PCT No.: PCT/EP2019/054165
§ 371 (c)(1),
(2) Date: Oct. 9, 2020

(87) PCT Pub. No.: WO2019/162301
PCT Pub. Date: Aug. 29, 2019

(65) Prior Publication Data
US 2021/0162001 A1    Jun. 3, 2021

(30) Foreign Application Priority Data
Feb. 20, 2018   (SE) .................................. 1850186-6

(51) Int. Cl.
| A61K 38/16 | (2006.01) |
|---|---|
| A61K 45/06 | (2006.01) |
| A61L 15/46 | (2006.01) |
| A61L 29/16 | (2006.01) |
| A61L 31/16 | (2006.01) |
| C07K 14/335 | (2006.01) |

(52) U.S. Cl.
CPC ............ *A61K 38/164* (2013.01); *A61L 29/16* (2013.01); *A61L 31/16* (2013.01); *A61L 2300/406* (2013.01)

(58) Field of Classification Search
CPC ....... A61K 38/164; A61L 29/16; A61L 31/16; A61L 2300/406
See application file for complete search history.

(56) References Cited

U.S. PATENT DOCUMENTS

| 2011/0150917 A1 | 6/2011 | Hancock et al. |
| 2013/0244923 A1 | 9/2013 | Nishina et al. |
| 2014/0142028 A1 | 5/2014 | Eckert et al. |

FOREIGN PATENT DOCUMENTS

| CN | 105254723 A | | 1/2016 | |
|---|---|---|---|---|
| EP | WO2014060610 | * | 4/2014 | ............ A61K 38/00 |
| SE | 1650188 A1 | | 8/2017 | |

OTHER PUBLICATIONS

Mombelli et al., "topical and systematic antibiotics in the management of periodontal diseases," international dental Journal 54:3-14 (2004) (Year: 2004).*
Bork, P. Powers and pitfalls in sequence analysis: the 70% hurdle. Genome Res 10: 398-400, 2000 (Year: 2000).*
Skolnick et al. From genes to protein structure and function: novel applications of computational approaches in the genomic era. Trends Biotechnol 18(1):34-39 2000 (Year: 2000 ).*
Doerks et al. Protein annotation: detective work for function prediction. Trends in Genetics 14:248-250, 1998 (Year: 1998).*
Smith et al. The challenges of genome sequence annotation or "the devil is in the details". Nature Biotechnol 15: 1222-1223, 1997 (Year: 1997).*
Brenner. S.E. Errors in genome annotation. Trends in Genetics 15:132-133, 1999 (Year: 1999).*
Tokuriki et al. Stability effects of mutations and protein evolvability. Curr Opin Structural Biol 19: 596-604, 2009 ( (Year: 2009).*
Fenton et al. Rheostat positions: a new classification of protein positions relevant to pharmacogenomics. Medicinal Chem Res 29:1133-1146, 2020 (Year: 2020).*
Bhattacharya et al. Impact of genetic variation on three dimensional structure and function of proteins. PLoS One 12(3): e0171355, 2017 (Year: 2017).*
Guo et al. Protein tolerance to random amino acid change. Proc Natl Acad Sci USA 101(25): 9205-9210, 2004 (Year: 2004).*
UniProtKB Q84HW0, accessed Aug. 27, 2023 at URL rest.uniprot.org/uniprotkb/Q84HW0.txt, pp. 1-2 (Year: 2023).*
UniProtKB Q84HW1 (accessed Aug. 27, 2023 at URL rest.uniprot.org/uniprotkb/Q84HW1.txt, pp. 1-2) (Year: 2023).*
Gallo et al, "Biology and clinical relevance of naturally occurring," J Allergy Clin Immunol 110: 823-831 (2002) (Year: 2002).*
Adessi et al., "Converting a Peptide into a Drug: Strategies to Improve Stability and Bioavailability," Current Medicinal Chemistry 9: 963-978 (2002) (Year: 2002).*
Bengtsson, Torbjörn et al., Dualaction of bacteriocin PLNC8 αβ through inhibition of Porphyromonas gingivalis infection and promotion of cell proliferation, Pathogens and Disease, vol. 75, No. 5, pp. 1-10 (Jun. 12, 2017).

(Continued)

*Primary Examiner* — Julie Ha
*Assistant Examiner* — Kristina M Hellman
(74) *Attorney, Agent, or Firm* — Porter Wright Morris & Arthur LLP

(57) ABSTRACT

In the invention, a pharmaceutical composition is provided, comprising a first and a second peptide. The first peptide is a peptide of the bacteriocin PLNC8 αβ, wherein the peptide of the bacteriocin PLNC8 αβ is a peptide A having at least 90%, 95%, 96%, 97%, 98% or 99% sequence identity (% SI) with SEQ ID NO 1, or a peptide B having at least 90%, 95%, 96%, 97%, 98% or 99% sequence identity (% SI) with SEQ ID NO 2. When the first peptide is peptide A, the second peptide B' having 14 to 34 amino acids and comprising a peptide having at least 90%>, 95%>, 96%>, 97%>, 98%> or 99% sequence identity (% SI) with SEQ ID NO 3. When the first peptide is peptide B, the second peptide A' having 15 to 29 amino acids and comprising a peptide having at least 90%, 95%, 96%, 97%, 98% or 99% sequence identity (% SI) with SEQ ID NO 4. The pharmaceutical composition further comprises at least one antibiotic. The pharmaceutical composition may be used in the treatment or prophylaxis of a bacterial infection.

60 Claims, 25 Drawing Sheets

Specification includes a Sequence Listing.

(56) References Cited

OTHER PUBLICATIONS

Cavera, Veronica L. et al., Bacteriocins and their position in the next wave of conventional antibiotics, International Journal of Antimicrobial Agents, vol. 46, pp. 494-501 (2015).

Khalaf, Hazem et al., Anitbacterial effects of Lactobacillus and bacteriocin PLNC8 αβ on the periodontal pathogen Porphyromonas gingivalis, BMC Microbiology, vol. 16, No. 188, pp. 1-11 (2016).

Maldonado, Antonio et al., Purification and Genetic Characterization of Plantaricin NC8, a Novel Coculture-Inducible Two-Peptide Bacteriocin from Lactobacillus plantarum NC8, Applied and Environmental Microbiology, p. 383-389 (2003).

Mataraci, Emel et al., In Vitro Activities of Antibiotics and Antimicrobial Cationic Peptides Alone and in Combination against Methicillin-Resistant *Staphylococcus aureus* Biofilms, Antimicrobial Agents and Chemotherapy, vol. 56, No. 12, pp. 6366-6371 (2012).

Tong et al., Antibacterial peptide nisin: A potential role in the inhibition of oral pathogenic bacteria, Peptides, vol. 60, pp. 32-40 (2014).

\* cited by examiner

Table 1

| Bacteria | Characteristics |
|---|---|
| *S. aureus* ATCC 29213 (MSSA) | Methicillin sensitive |
| *S. aureus* CCUG 35601 (MRSA) | Methicillin resistant |
| *S. epidermidis* ATCC 12228 | Biofilm negative |
| *S. epidermidis* RP62A | Biofilm positive |
| *S. epidermidis* N15 | Isolated from nose of a healthy individual |
| *S. epidermidis* 117 | Isolated from an infected hip joint prosthesis |

(B)

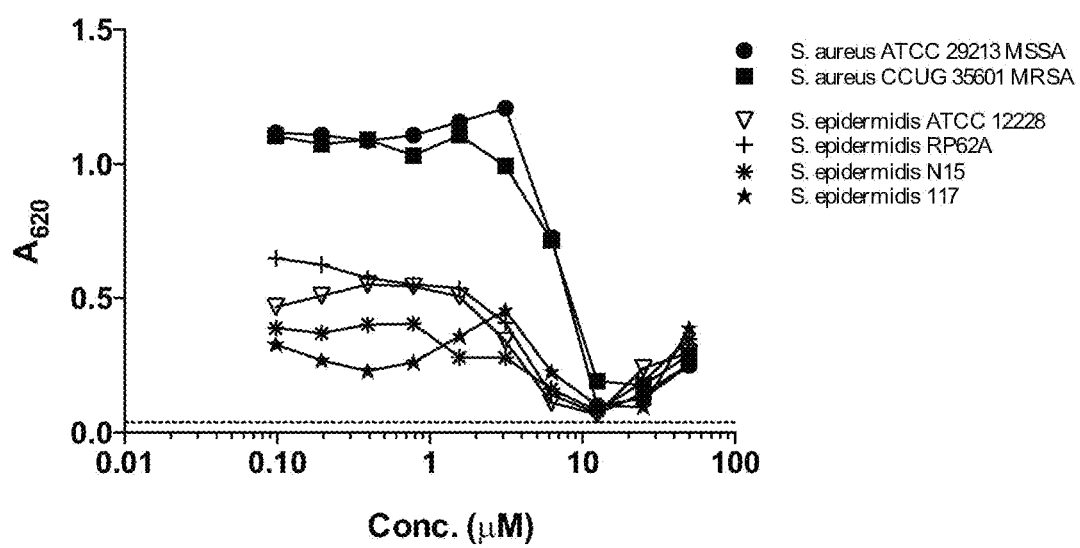

(C)

| L-PLNC8 αβ | MIC | MBC |
|---|---|---|
| *S. aureus* ATCC 29213 (MSSA) | 12.5 | 25 |
| *S. aureus* CCUG 35601 (MRSA) | 12.5 | 25 |
| *S. epidermidis* ATCC 12228 | 6.25 | 12.5 |
| *S. epidermidis* RP62A | 6.25 | 6.25 |
| *S. epidermidis* N15 | 6.25 | 6.25 |
| *S. epidermidis* 117 | 12.5 | 12.5 |

Figure 7
A
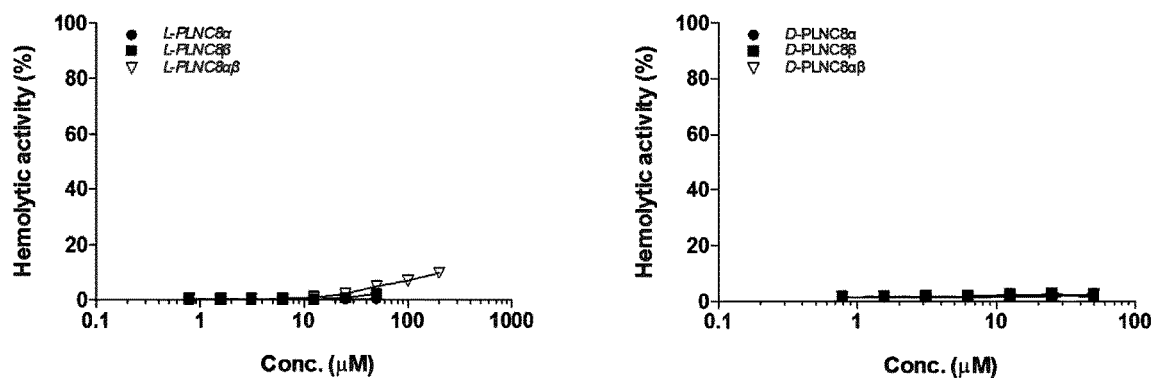
B
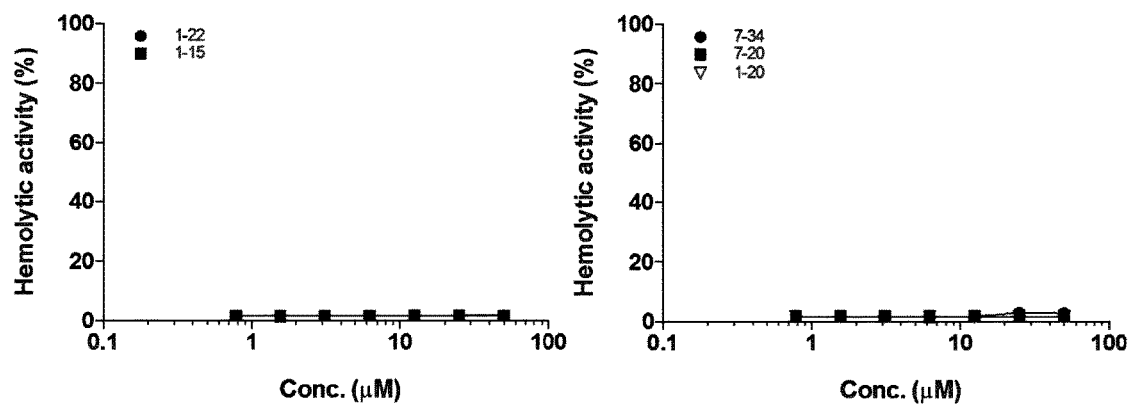

Figure 8

PLNC8α

| SEQ ID NO | Peptide ID | MW | H₂N- 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 -COOH |
|---|---|---|---|---|---|---|---|---|---|---|---|---|---|---|---|---|---|---|---|---|---|---|---|---|---|---|---|---|---|---|---|
| 38 | 23-29 | 918.05 | | | | | | | | | | | | | | | | | | | | | | | K | H | P | Y | V | Q | F |
| 39 | 16-29 | 1815.13 | | | | | | | | | | | | | | | | K | K | A | R | W | N | L | K | H | P | Y | V | Q | F |
| 40 | 9-29 | 2642.02 | | | | | | | | | S | W | G | Y | Y | L | G | K | K | A | R | W | N | L | K | H | P | Y | V | Q | F |
| 1 | 1-29 | 3587.09 | D | L | L | K | L | W | S | S | W | G | Y | Y | L | G | K | K | A | R | W | N | L | K | H | P | Y | V | Q | F |
| 41 | 16-22 | 915.09 | | | | | | | | | | | | | | | | K | K | A | R | W | N | L | | | | | | | |
| 42 | 9-22 | 1741.99 | | | | | | | | | S | W | G | Y | Y | L | G | K | K | A | R | W | N | L | | | | | | | |
| 43 | 1-22 | 2687.06 | D | L | L | K | L | W | S | S | W | G | Y | Y | L | G | K | K | A | R | W | N | L | | | | | | | |
| 44 | 9-15 | 844.93 | | | | | | | | | S | W | G | Y | Y | L | G | | | | | | | | | | | | | | |
| 45 | 1-15 | 1789.98 | D | L | L | K | L | W | S | S | W | G | Y | Y | L | G | | | | | | | | | | | | | | | |
| 46 | 1-8 | 963.08 | D | L | L | K | L | W | S | S | | | | | | | | | | | | | | | | | | | | | |

PLNC8β

| SEQ ID NO | Peptide ID | MW | H₂N- 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 -COOH |
|---|---|---|---|---|---|---|---|---|---|---|---|---|---|---|---|---|---|---|---|---|---|---|---|---|---|---|---|---|---|---|---|---|---|---|---|
| 47 | 28-34 | 913 | | | | | | | | | | | | | | | | | | | | | | | | | | | | F | N | K | G | F | Y | H |
| 48 | 21-34 | 1754.98 | | | | | | | | | | | | | | | | | | | | | R | K | T | I | E | K | S | F | N | K | G | F | Y | H |
| 49 | 14-34 | 2640.99 | | | | | | | | | | | | | L | W | S | A | Y | K | H | R | K | T | I | E | K | S | F | N | K | G | F | Y | H |
| 50 | 7-34 | 3439.96 | | | | | | | Y | T | L | G | K | I | L | W | S | A | Y | K | H | R | K | T | I | E | K | S | F | N | K | G | F | Y | H |
| 51 | 14-20 | 904.02 | | | | | | | | | | | | | L | W | S | A | Y | K | H | | | | | | | | | | | | | | |
| 52 | 7-20 | 1693.00 | | | | | | | Y | T | L | G | K | I | L | W | S | A | Y | K | H | | | | | | | | | | | | | | |
| 53 | 1-30 | 2263.63 | S | V | P | T | S | V | Y | T | L | G | K | I | L | W | S | A | Y | K | H | R | K | T | I | E | K | S | F | N | K | G |
| 2 | 1-34 | 4000.6 | S | V | P | T | S | V | Y | T | L | G | K | I | L | W | S | A | Y | K | H | R | K | T | I | E | K | S | F | N | K | G | F | Y | H |
| 54 | 7-13 | 806.99 | | | | | | | Y | T | L | G | K | I | L | | | | | | | | | | | | | | | | | | | | |
| 55 | (1-6)(7-13)₂ | 2166.6 | S | V | P | T | S | V | Y | T | L | G | K | I | L | | | | | | | | | | | | | | | | | | | | |
| 56 | 1-6 | 588.65 | S | V | P | T | S | V | | | | | | | | | | | | | | | | | | | | | | | | | | | |
| 57 | 1-13 | 1377.62 | S | V | P | T | S | V | Y | T | L | G | K | I | L | | | | | | | | | | | | | | | | | | | | |
| 58 | 10-17 | 887.08 | | | | | | | | | | G | K | I | L | W | S | A | | | | | | | | | | | | | | | | | |
| 59 | 4-17 | 1551.82 | | | | T | S | V | Y | T | L | G | K | I | L | W | S | A | | | | | | | | | | | | | | | | | |

Figure 10
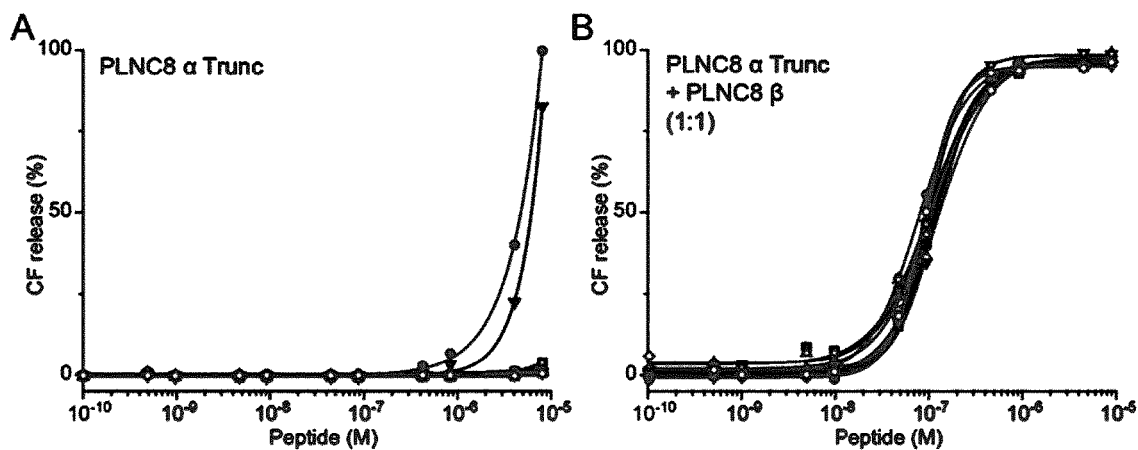
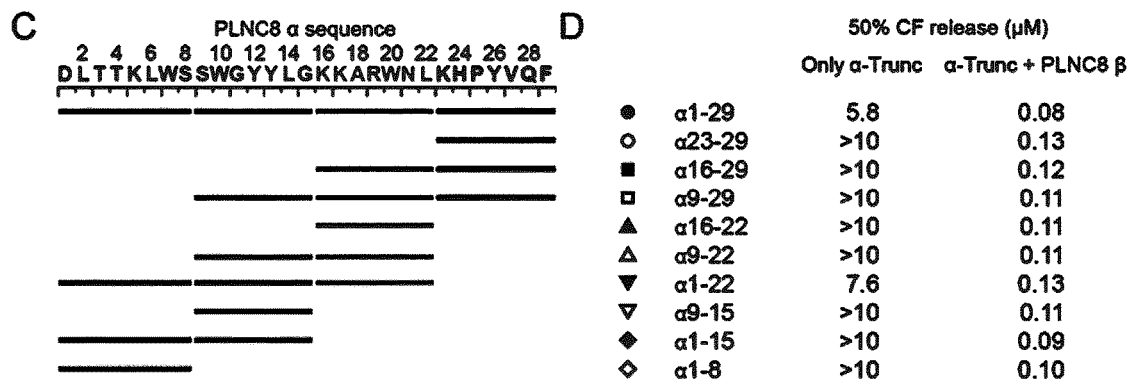

Figure 11

| Peptide (1:1) | MIC | MBC |
|---|---|---|
| α1-22/β1-20 | 12.5 | >50 |
| α1-22/β7-20 | 25 | >50 |
| α1-15/β1-20 | 25 | >50 |
| α1-15/β7-20 | 25 | >50 |

Figure 14

|  | Strain | MIC | MBC |
|---|---|---|---|
| hGISE | 157 | 12.5 | >50 |
|  | 126 | 12.5 | 50 |
|  | 145 | 6.25 | >50 |
|  | 109 | 6.25 | >50 |
|  | 127 | 12.5 | 50 |
|  | 117 | 6.25 | 25 |
|  | 154 | 6.25 | 12.5 |
|  | 138 | 6.25 | 6.25 |
|  | 152 | 6.25 | 12.5 |
|  | 124 | 6.25 | 6.25 |

Figure 17
(A)
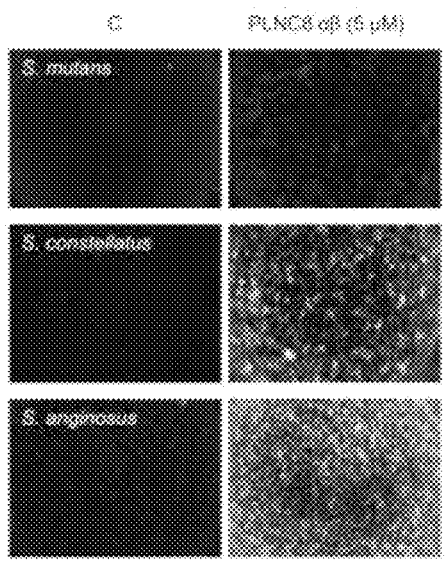
(B)
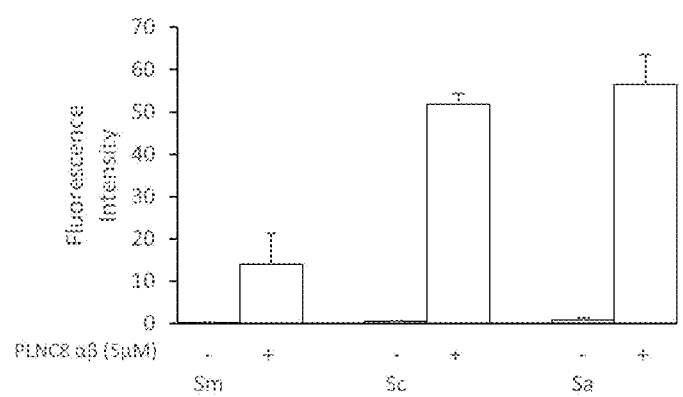

Figure 27
A
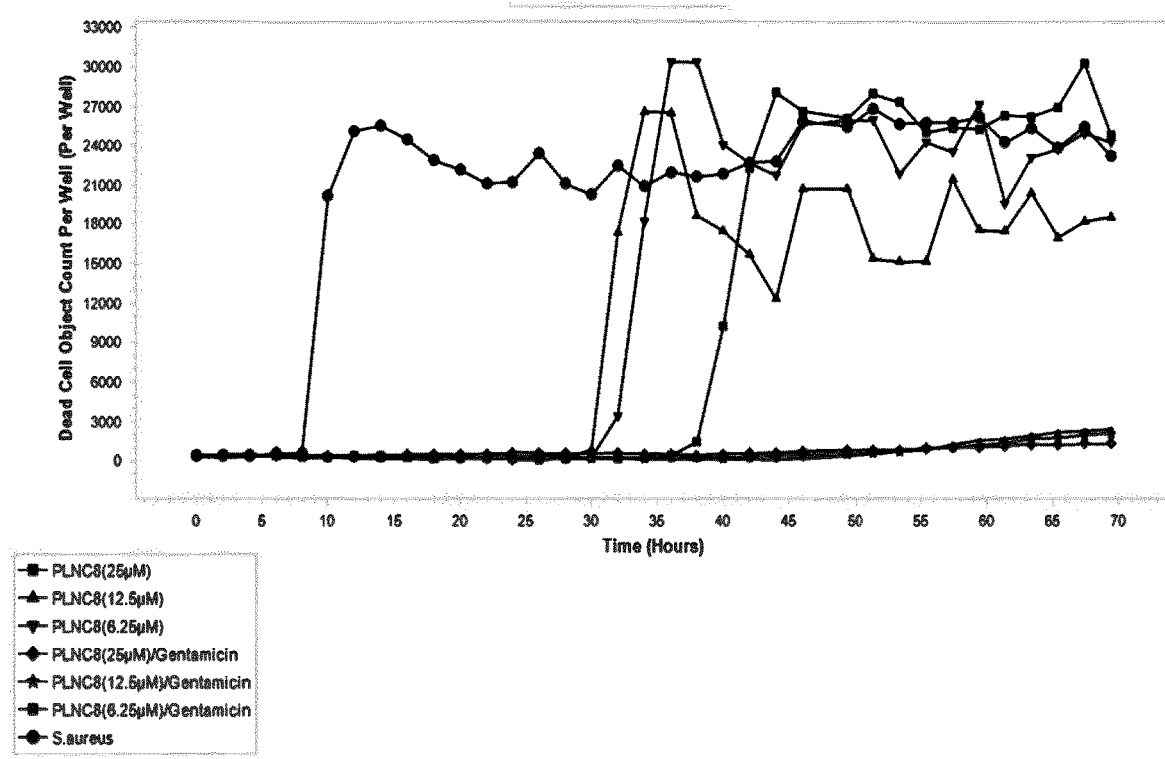
B
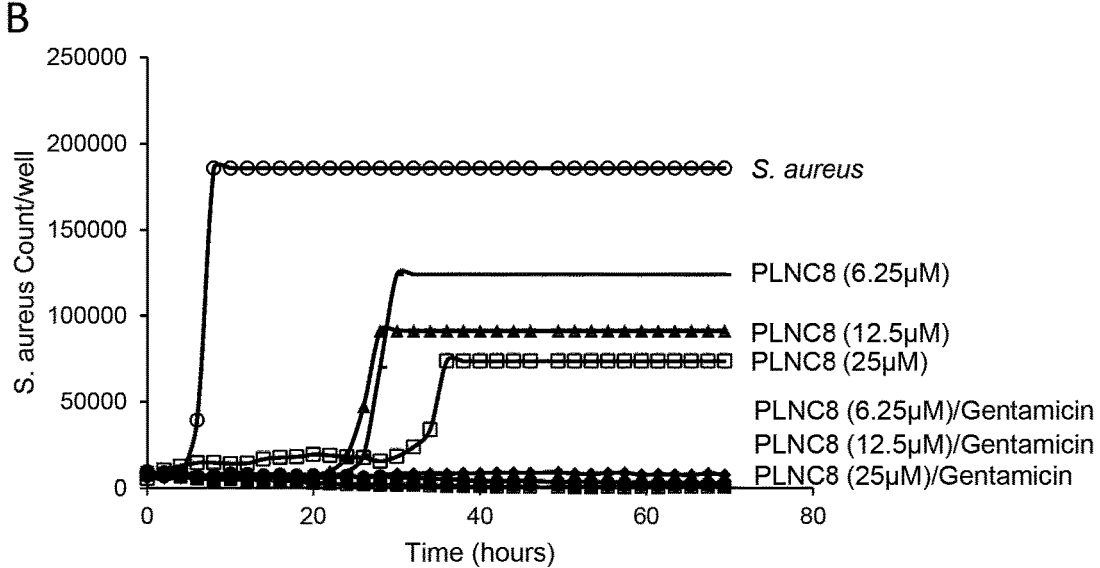

SEQUENCE LISTING

```
<160> NUMBER OF SEQ ID NOS: 61

<210> SEQ ID NO 1
<211> LENGTH: 29
<212> TYPE: PRT
<213> ORGANISM: Lactobacillus plantarum NC8

<400> SEQUENCE: 1

Asp Leu Thr Thr Lys Leu Trp Ser Ser Trp Gly Tyr Tyr Leu Gly Lys
1               5                   10                  15

Lys Ala Arg Trp Asn Leu Lys His Pro Tyr Val Gln Phe
            20                  25

<210> SEQ ID NO 2
<211> LENGTH: 34
<212> TYPE: PRT
<213> ORGANISM: Lactobacillus plantarum NC8

<400> SEQUENCE: 2

Ser Val Pro Thr Ser Val Tyr Thr Leu Gly Ile Lys Ile Leu Trp Ser
1               5                   10                  15

Ala Tyr Lys His Arg Lys Thr Ile Glu Lys Ser Phe Asn Lys Gly Phe
            20                  25                  30

Tyr His

<210> SEQ ID NO 3
<211> LENGTH: 14
<212> TYPE: PRT
<213> ORGANISM: Lactobacillus plantarum NC8

<400> SEQUENCE: 3

Tyr Thr Leu Gly Ile Lys Ile Leu Trp Ser Ala Tyr Lys His
1               5                   10
```

```
<210> SEQ ID NO 4
<211> LENGTH: 15
<212> TYPE: PRT
<213> ORGANISM: Lactobacillus plantarum NC8

<400> SEQUENCE: 4

Asp Leu Thr Thr Lys Leu Trp Ser Ser Trp Gly Tyr Tyr Leu Gly
1               5                   10                  15

<210> SEQ ID NO 5
<211> LENGTH: 20
<212> TYPE: PRT
<213> ORGANISM: Lactobacillus plantarum NC8

<400> SEQUENCE: 5

Ser Val Pro Thr Ser Val Tyr Thr Leu Gly Ile Lys Ile Leu Trp Ser
1               5                   10                  15

Ala Tyr Lys His
            20

<210> SEQ ID NO 6
<211> LENGTH: 19
<212> TYPE: PRT
<213> ORGANISM: Lactobacillus plantarum NC8

<400> SEQUENCE: 6

Val Pro Thr Ser Val Tyr Thr Leu Gly Ile Lys Ile Leu Trp Ser Ala
1               5                   10                  15

Tyr Lys His

<210> SEQ ID NO 7
<211> LENGTH: 18
<212> TYPE: PRT
<213> ORGANISM: Lactobacillus plantarum NC8

<400> SEQUENCE: 7

Pro Thr Ser Val Tyr Thr Leu Gly Ile Lys Ile Leu Trp Ser Ala Tyr
1               5                   10                  15

Lys His

<210> SEQ ID NO 8
<211> LENGTH: 17
<212> TYPE: PRT
<213> ORGANISM: Lactobacillus plantarum NC8

<400> SEQUENCE: 8

Thr Ser Val Tyr Thr Leu Gly Ile Lys Ile Leu Trp Ser Ala Tyr Lys
1               5                   10                  15

His

<210> SEQ ID NO 9
<211> LENGTH: 16
<212> TYPE: PRT
<213> ORGANISM: Lactobacillus plantarum NC8

<400> SEQUENCE: 9

Ser Val Tyr Thr Leu Gly Ile Lys Ile Leu Trp Ser Ala Tyr Lys His
1               5                   10                  15

<210> SEQ ID NO 10
<211> LENGTH: 15
<212> TYPE: PRT
```

<213> ORGANISM: Lactobacillus plantarum NC8

<400> SEQUENCE: 10

Val Tyr Thr Leu Gly Ile Lys Ile Leu Trp Ser Ala Tyr Lys His
1               5                   10                  15

<210> SEQ ID NO 11
<211> LENGTH: 15
<212> TYPE: PRT
<213> ORGANISM: Lactobacillus plantarum NC8

<400> SEQUENCE: 11

Tyr Thr Leu Gly Ile Lys Ile Leu Trp Ser Ala Tyr Lys His Arg
1               5                   10                  15

<210> SEQ ID NO 12
<211> LENGTH: 16
<212> TYPE: PRT
<213> ORGANISM: Lactobacillus plantarum NC8

<400> SEQUENCE: 12

Tyr Thr Leu Gly Ile Lys Ile Leu Trp Ser Ala Tyr Lys His Arg Lys
1               5                   10                  15

<210> SEQ ID NO 13
<211> LENGTH: 17
<212> TYPE: PRT
<213> ORGANISM: Lactobacillus plantarum NC8

<400> SEQUENCE: 13

Tyr Thr Leu Gly Ile Lys Ile Leu Trp Ser Ala Tyr Lys His Arg Lys
1               5                   10                  15

Thr

<210> SEQ ID NO 14
<211> LENGTH: 18
<212> TYPE: PRT
<213> ORGANISM: Lactobacillus plantarum NC8

<400> SEQUENCE: 14

Tyr Thr Leu Gly Ile Lys Ile Leu Trp Ser Ala Tyr Lys His Arg Lys
1               5                   10                  15

Thr Ile

<210> SEQ ID NO 15
<211> LENGTH: 19
<212> TYPE: PRT
<213> ORGANISM: Lactobacillus plantarum NC8

<400> SEQUENCE: 15

Tyr Thr Leu Gly Ile Lys Ile Leu Trp Ser Ala Tyr Lys His Arg Lys
1               5                   10                  15

Thr Ile Glu

<210> SEQ ID NO 16
<211> LENGTH: 20
<212> TYPE: PRT
<213> ORGANISM: Lactobacillus plantarum NC8

<400> SEQUENCE: 16

Tyr Thr Leu Gly Ile Lys Ile Leu Trp Ser Ala Tyr Lys His Arg Lys
1               5                   10                  15

Thr Ile Glu Lys
        20

<210> SEQ ID NO 17
<211> LENGTH: 21
<212> TYPE: PRT
<213> ORGANISM: Lactobacillus plantarum NC8

<400> SEQUENCE: 17

Tyr Thr Leu Gly Ile Lys Ile Leu Trp Ser Ala Tyr Lys His Arg Lys
1               5                   10                  15

Thr Ile Glu Lys Ser
        20

<210> SEQ ID NO 18
<211> LENGTH: 22
<212> TYPE: PRT
<213> ORGANISM: Lactobacillus plantarum NC8

<400> SEQUENCE: 18

Tyr Thr Leu Gly Ile Lys Ile Leu Trp Ser Ala Tyr Lys His Arg Lys
1               5                   10                  15

Thr Ile Glu Lys Ser Phe
        20

<210> SEQ ID NO 19
<211> LENGTH: 23
<212> TYPE: PRT
<213> ORGANISM: Lactobacillus plantarum NC8

<400> SEQUENCE: 19

Tyr Thr Leu Gly Ile Lys Ile Leu Trp Ser Ala Tyr Lys His Arg Lys
1               5                   10                  15

Thr Ile Glu Lys Ser Phe Asn
        20

<210> SEQ ID NO 20
<211> LENGTH: 24
<212> TYPE: PRT
<213> ORGANISM: Lactobacillus plantarum NC8

<400> SEQUENCE: 20

Tyr Thr Leu Gly Ile Lys Ile Leu Trp Ser Ala Tyr Lys His Arg Lys
1               5                   10                  15

Thr Ile Glu Lys Ser Phe Asn Lys
        20

<210> SEQ ID NO 21
<211> LENGTH: 25
<212> TYPE: PRT
<213> ORGANISM: Lactobacillus plantarum NC8

<400> SEQUENCE: 21

Tyr Thr Leu Gly Ile Lys Ile Leu Trp Ser Ala Tyr Lys His Arg Lys
1               5                   10                  15

Thr Ile Glu Lys Ser Phe Asn Lys Gly
        20                  25

<210> SEQ ID NO 22
<211> LENGTH: 26
<212> TYPE: PRT
<213> ORGANISM: Lactobacillus plantarum NC8

```
<400> SEQUENCE: 22

Tyr Thr Leu Gly Ile Lys Ile Leu Trp Ser Ala Tyr Lys His Arg Lys
1               5                   10                  15

Thr Ile Glu Lys Ser Phe Asn Lys Gly Phe
            20                  25

<210> SEQ ID NO 23
<211> LENGTH: 27
<212> TYPE: PRT
<213> ORGANISM: Lactobacillus plantarum NC8

<400> SEQUENCE: 23

Tyr Thr Leu Gly Ile Lys Ile Leu Trp Ser Ala Tyr Lys His Arg Lys
1               5                   10                  15

Thr Ile Glu Lys Ser Phe Asn Lys Gly Phe Tyr
            20                  25

<210> SEQ ID NO 24
<211> LENGTH: 28
<212> TYPE: PRT
<213> ORGANISM: Lactobacillus plantarum NC8

<400> SEQUENCE: 24

Tyr Thr Leu Gly Ile Lys Ile Leu Trp Ser Ala Tyr Lys His Arg Lys
1               5                   10                  15

Thr Ile Glu Lys Ser Phe Asn Lys Gly Phe Tyr His
            20                  25

<210> SEQ ID NO 25
<211> LENGTH: 28
<212> TYPE: PRT
<213> ORGANISM: Lactobacillus plantarum NC8

<400> SEQUENCE: 25

Asp Leu Thr Thr Lys Leu Trp Ser Ser Trp Gly Tyr Tyr Leu Gly Lys
1               5                   10                  15

Lys Ala Arg Trp Asn Leu Lys His Pro Tyr Val Gln
            20                  25

<210> SEQ ID NO 26
<211> LENGTH: 27
<212> TYPE: PRT
<213> ORGANISM: Lactobacillus plantarum NC8

<400> SEQUENCE: 26

Asp Leu Thr Thr Lys Leu Trp Ser Ser Trp Gly Tyr Tyr Leu Gly Lys
1               5                   10                  15

Lys Ala Arg Trp Asn Leu Lys His Pro Tyr Val
            20                  25

<210> SEQ ID NO 27
<211> LENGTH: 26
<212> TYPE: PRT
<213> ORGANISM: Lactobacillus plantarum NC8

<400> SEQUENCE: 27

Asp Leu Thr Thr Lys Leu Trp Ser Ser Trp Gly Tyr Tyr Leu Gly Lys
1               5                   10                  15

Lys Ala Arg Trp Asn Leu Lys His Pro Tyr
            20                  25
```

-continued

```
<210> SEQ ID NO 28
<211> LENGTH: 25
<212> TYPE: PRT
<213> ORGANISM: Lactobacillus plantarum NC8

<400> SEQUENCE: 28

Asp Leu Thr Thr Lys Leu Trp Ser Ser Trp Gly Tyr Tyr Leu Gly Lys
1               5                   10                  15

Lys Ala Arg Trp Asn Leu Lys His Pro
            20                  25

<210> SEQ ID NO 29
<211> LENGTH: 24
<212> TYPE: PRT
<213> ORGANISM: Lactobacillus plantarum NC8

<400> SEQUENCE: 29

Asp Leu Thr Thr Lys Leu Trp Ser Ser Trp Gly Tyr Tyr Leu Gly Lys
1               5                   10                  15

Lys Ala Arg Trp Asn Leu Lys His
            20

<210> SEQ ID NO 30
<211> LENGTH: 23
<212> TYPE: PRT
<213> ORGANISM: Lactobacillus plantarum NC8

<400> SEQUENCE: 30

Asp Leu Thr Thr Lys Leu Trp Ser Ser Trp Gly Tyr Tyr Leu Gly Lys
1               5                   10                  15

Lys Ala Arg Trp Asn Leu Lys
            20

<210> SEQ ID NO 31
<211> LENGTH: 22
<212> TYPE: PRT
<213> ORGANISM: Lactobacillus plantarum NC8

<400> SEQUENCE: 31

Asp Leu Thr Thr Lys Leu Trp Ser Ser Trp Gly Tyr Tyr Leu Gly Lys
1               5                   10                  15

Lys Ala Arg Trp Asn Leu
            20

<210> SEQ ID NO 32
<211> LENGTH: 21
<212> TYPE: PRT
<213> ORGANISM: Lactobacillus plantarum NC8

<400> SEQUENCE: 32

Asp Leu Thr Thr Lys Leu Trp Ser Ser Trp Gly Tyr Tyr Leu Gly Lys
1               5                   10                  15

Lys Ala Arg Trp Asn
            20

<210> SEQ ID NO 33
<211> LENGTH: 20
<212> TYPE: PRT
<213> ORGANISM: Lactobacillus plantarum NC8

<400> SEQUENCE: 33

Asp Leu Thr Thr Lys Leu Trp Ser Ser Trp Gly Tyr Tyr Leu Gly Lys
1               5                   10                  15
```

```
Lys Ala Arg Trp
            20

<210> SEQ ID NO 34
<211> LENGTH: 19
<212> TYPE: PRT
<213> ORGANISM: Lactobacillus plantarum NC8

<400> SEQUENCE: 34

Asp Leu Thr Thr Lys Leu Trp Ser Ser Trp Gly Tyr Tyr Leu Gly Lys
1               5                   10                  15

Lys Ala Arg

<210> SEQ ID NO 35
<211> LENGTH: 18
<212> TYPE: PRT
<213> ORGANISM: Lactobacillus plantarum NC8

<400> SEQUENCE: 35

Asp Leu Thr Thr Lys Leu Trp Ser Ser Trp Gly Tyr Tyr Leu Gly Lys
1               5                   10                  15

Lys Ala

<210> SEQ ID NO 36
<211> LENGTH: 17
<212> TYPE: PRT
<213> ORGANISM: Lactobacillus plantarum NC8

<400> SEQUENCE: 36

Asp Leu Thr Thr Lys Leu Trp Ser Ser Trp Gly Tyr Tyr Leu Gly Lys
1               5                   10                  15

Lys

<210> SEQ ID NO 37
<211> LENGTH: 16
<212> TYPE: PRT
<213> ORGANISM: Lactobacillus plantarum NC8

<400> SEQUENCE: 37

Asp Leu Thr Thr Lys Leu Trp Ser Ser Trp Gly Tyr Tyr Leu Gly Lys
1               5                   10                  15

<210> SEQ ID NO 38
<211> LENGTH: 7
<212> TYPE: PRT
<213> ORGANISM: Lactobacillus plantarum NC8

<400> SEQUENCE: 38

Lys His Pro Tyr Val Gln Phe
1               5

<210> SEQ ID NO 39
<211> LENGTH: 14
<212> TYPE: PRT
<213> ORGANISM: Lactobacillus plantarum NC8

<400> SEQUENCE: 39

Lys Lys Ala Arg Trp Asn Leu Lys His Pro Tyr Val Gln Phe
1               5                   10

<210> SEQ ID NO 40
<211> LENGTH: 21
```

```
<212> TYPE: PRT
<213> ORGANISM: Lactobacillus plantarum NC8

<400> SEQUENCE: 40

Ser Trp Gly Tyr Tyr Leu Gly Lys Lys Ala Arg Trp Asn Leu Lys His
1               5                   10                  15

Pro Tyr Val Gln Phe
            20

<210> SEQ ID NO 41
<211> LENGTH: 7
<212> TYPE: PRT
<213> ORGANISM: Lactobacillus plantarum NC8

<400> SEQUENCE: 41

Lys Lys Ala Arg Trp Asn Leu
1               5

<210> SEQ ID NO 42
<211> LENGTH: 14
<212> TYPE: PRT
<213> ORGANISM: Lactobacillus plantarum NC8

<400> SEQUENCE: 42

Ser Trp Gly Tyr Tyr Leu Gly Lys Lys Ala Arg Trp Asn Leu
1               5                   10

<210> SEQ ID NO 43
<211> LENGTH: 22
<212> TYPE: PRT
<213> ORGANISM: Lactobacillus plantarum NC8

<400> SEQUENCE: 43

Asp Leu Thr Thr Lys Leu Trp Ser Ser Trp Gly Tyr Tyr Leu Gly Lys
1               5                   10                  15

Lys Ala Arg Trp Asn Leu
            20

<210> SEQ ID NO 44
<211> LENGTH: 7
<212> TYPE: PRT
<213> ORGANISM: Lactobacillus plantarum NC8

<400> SEQUENCE: 44

Ser Trp Gly Tyr Tyr Leu Gly
1               5

<210> SEQ ID NO 45
<211> LENGTH: 15
<212> TYPE: PRT
<213> ORGANISM: Lactobacillus plantarum NC8

<400> SEQUENCE: 45

Asp Leu Thr Thr Lys Leu Trp Ser Ser Trp Gly Tyr Tyr Leu Gly
1               5                   10                  15

<210> SEQ ID NO 46
<211> LENGTH: 8
<212> TYPE: PRT
<213> ORGANISM: Lactobacillus plantarum NC8

<400> SEQUENCE: 46

Asp Leu Thr Thr Lys Leu Trp Ser
1               5
```

```
<210> SEQ ID NO 47
<211> LENGTH: 7
<212> TYPE: PRT
<213> ORGANISM: Lactobacillus plantarum NC8

<400> SEQUENCE: 47

Phe Asn Lys Gly Phe Tyr His
1               5

<210> SEQ ID NO 48
<211> LENGTH: 14
<212> TYPE: PRT
<213> ORGANISM: Lactobacillus plantarum NC8

<400> SEQUENCE: 48

Arg Lys Thr Ile Glu Lys Ser Phe Asn Lys Gly Phe Tyr His
1               5                   10

<210> SEQ ID NO 49
<211> LENGTH: 21
<212> TYPE: PRT
<213> ORGANISM: Lactobacillus plantarum NC8

<400> SEQUENCE: 49

Leu Trp Ser Ala Tyr Lys His Arg Lys Thr Ile Glu Lys Ser Phe Asn
1               5                   10                  15

Lys Gly Phe Tyr His
            20

<210> SEQ ID NO 50
<211> LENGTH: 28
<212> TYPE: PRT
<213> ORGANISM: Lactobacillus plantarum NC8

<400> SEQUENCE: 50

Tyr Thr Leu Gly Ile Lys Ile Leu Trp Ser Ala Tyr Lys His Arg Lys
1               5                   10                  15

Thr Ile Glu Lys Ser Phe Asn Lys Gly Phe Tyr His
            20                  25

<210> SEQ ID NO 51
<211> LENGTH: 7
<212> TYPE: PRT
<213> ORGANISM: Lactobacillus plantarum NC8

<400> SEQUENCE: 51

Leu Trp Ser Ala Tyr Lys His
1               5

<210> SEQ ID NO 52
<211> LENGTH: 14
<212> TYPE: PRT
<213> ORGANISM: Lactobacillus plantarum NC8

<400> SEQUENCE: 52

Tyr Thr Leu Gly Ile Lys Ile Leu Trp Ser Ala Tyr Lys His
1               5                   10

<210> SEQ ID NO 53
<211> LENGTH: 20
<212> TYPE: PRT
<213> ORGANISM: Lactobacillus plantarum NC8
```

<400> SEQUENCE: 53

Ser Val Pro Thr Ser Val Tyr Thr Leu Gly Ile Lys Ile Leu Trp Ser
1               5                   10                  15

Ala Tyr Lys His
            20

<210> SEQ ID NO 54
<211> LENGTH: 7
<212> TYPE: PRT
<213> ORGANISM: Lactobacillus plantarum NC8

<400> SEQUENCE: 54

Tyr Thr Leu Gly Ile Lys Ile
1               5

<210> SEQ ID NO 55
<211> LENGTH: 20
<212> TYPE: PRT
<213> ORGANISM: Lactobacillus plantarum NC8

<400> SEQUENCE: 55

Ser Val Pro Thr Ser Val Tyr Thr Leu Gly Ile Lys Ile Tyr Thr Leu
1               5                   10                  15

Gly Ile Lys Ile
            20

<210> SEQ ID NO 56
<211> LENGTH: 6
<212> TYPE: PRT
<213> ORGANISM: Lactobacillus plantarum NC8

<400> SEQUENCE: 56

Ser Val Pro Thr Ser Val
1               5

<210> SEQ ID NO 57
<211> LENGTH: 13
<212> TYPE: PRT
<213> ORGANISM: Lactobacillus plantarum NC8

<400> SEQUENCE: 57

Ser Val Pro Thr Ser Val Tyr Thr Leu Gly Ile Lys Ile
1               5                   10

<210> SEQ ID NO 58
<211> LENGTH: 8
<212> TYPE: PRT
<213> ORGANISM: Lactobacillus plantarum NC8

<400> SEQUENCE: 58

Gly Ile Lys Ile Leu Trp Ser Ala
1               5

<210> SEQ ID NO 59
<211> LENGTH: 14
<212> TYPE: PRT
<213> ORGANISM: Lactobacillus plantarum NC8

<400> SEQUENCE: 59

Thr Ser Val Tyr Thr Leu Gly Ile Lys Ile Leu Trp Ser Ala
1               5                   10

<210> SEQ ID NO 60

```
<211> LENGTH: 29
<212> TYPE: PRT
<213> ORGANISM: Lactobacillus plantarum NC8

<400> SEQUENCE: 60

Thr Trp Leu Lys Tyr Gly His Gly Asp Ala Lys Leu Trp Ser Trp Ser
1               5                   10                  15

Lys Pro Leu Asn Leu Thr Phe Arg Tyr Gln Tyr Val Lys
            20                  25

<210> SEQ ID NO 61
<211> LENGTH: 34
<212> TYPE: PRT
<213> ORGANISM: Lactobacillus plantarum NC8

<400> SEQUENCE: 61

Leu Lys Leu Trp Asn Thr Tyr Gly Thr Phe Ser Arg Phe Tyr Thr Ser
1               5                   10                  15

Lys Ser Glu Val Lys Ile Ala His Gly Ile Lys Ser Ile His Val Pro
            20                  25                  30

Tyr Lys
```

PLANTARICIN NC8 ALPHA BETA MARKEDLY ENHANCES THE EFFECTS OF ANTIBIOTICS

SEQUENCE LISTING

The Sequence Listing submitted herewith, entitled "June-5-2023-Sequence-Listing_ST25", created May 23, 2023, and having a size of 15,375 bytes, is incorporated herein by reference.

FIELD OF THE INVENTION

This invention pertains in general to the field of treatment of infections. More particularly the invention relates to a use of a pharmaceutical composition comprising bacteriocin PLNC8 αβ for the prevention and/or treatment of infections wherein the pharmaceutical composition further comprises at least one antibiotic.

BACKGROUND OF THE INVENTION

Hospital-acquired infection (HAI), also known as a nosocomial infection, is an infection that is acquired in a hospital or other health care facility. Such an infection can be acquired in hospital, nursing home, rehabilitation facility, outpatient clinic, or other clinical settings. Infection is spread to the susceptible patient in the clinical setting by various means. Health care staff can spread infection, in addition to contaminated equipment, bed linens, or air droplets. It is estimated that 6 million patients in the EU and USA contract a HAI per year, resulting in up to 150 000 deaths annually. Prevention of HAI often includes hospital sanitation protocols regarding uniforms, equipment sterilization, washing, and other preventive measures. Thorough hand washing and/or use of alcohol rubs by all medical personnel before and after each patient contact is one of the most effective ways to combat nosocomial infections. More careful use of antimicrobial agents, such as antibiotics, is also considered vital.

Among the categories of bacteria most known to infect patients are the ESKAPE pathogens (*Enterococcus faecium, Staphylococcus aureus, Klebsiella pneumoniae, Acinetobacter baumannii, Pseudomonas aeruginosa* and *Enterobacter*), including MRSA (Methicillin-resistant *Staphylococcus aureus*) and VRE (Vancomycin-resistant *Enterococcus*), *Streptococcus* spp and *Escherichia coli*. Development of new effective antimicrobial strategies in the treatment of infections caused by antibiotic-resistant bacteria presents one of the major challenges in medicine today. Since most infections are caused by pathogens that live protected in complex biofilms, antibacterial substances need a good ability to penetrate or dissolve biofilm. Such ability is usually limited/lacking in traditional antibiotics, which must therefore be compensated with very high concentrations, often 100-1000 times higher than the doses required for bactericidal effects on planktonic bacteria. This overdose contributes to accelerated development of antibiotic resistance and severe cytotoxic effects. Furthermore, infections are often associated with high proteolytic activity caused by both bacteria and the body's immune system, which means that antimicrobial agents may quickly become inactivated.

It is known that bacteriocins constitute a promising potential alternative or complement to traditional antibiotics and have several advantages such as low risk of resistance development, limited effects on normal flora and beneficial effects on human tissue. Bacteriocins are a group of bacterially produced peptides used to fight other bacteria. Bacteriocins may have a net positive charge and express amphipathic structures that interact with negatively charged microbial membranes and kill microbes usually through pore-forming mechanisms. These mechanisms are more difficult to evade by developing resistance, compared to metabolic enzymes, which usually are targets for conventional antibiotics.

Thus, there is a need for alternative method of antibiotic therapy in the prevention or treatment of bacteria and bacterial infections, especially spread of antibiotic resistance in health care (e.g. methicillin-resistant *Staphylococcus aureus* (MRSA), methicillin-resistant *Staphylococcus epidermidis* (MRSE), and vancomycin-resitant *Enterococcus* (VRE)).

SUMMARY OF THE INVENTION

Accordingly, the present invention preferably seeks to mitigate, alleviate or eliminate one or more of the above-identified deficiencies in the art and disadvantages singly or in any combination and solves at least the above mentioned problems by providing a pharmaceutical composition comprising a first and a second peptide, wherein the first peptide is a peptide of the bacteriocin PLNC8 αβ, wherein the peptide of the bacteriocin PLNC8 αβ is a peptide A having at least 90%, 95%, 96%, 97%, 98% or 99% sequence identity (% SI) with DLTTKLWSSWGYYLGK-KARWNLKHPYVQF SEQ ID NO 1, or a peptide B having at least 90%, 95%, 96%, 97%, 98% or 99% sequence identity (% SI) with SVPTSVYTLGIKILWSAYKHRKTIEKSFNKGFYH SEQ ID NO 2, and wherein when the first peptide is peptide A, the second peptide B' having 14 to 34 amino acids and comprising a peptide having at least 90%, 95%, 96%, 97%, 98% or 99% sequence identity (% SI) with YTLGIKILWSAYKH SEQ ID NO 3 when the first peptide is peptide B, the second peptide A' having 15 to 29 amino acids and comprising a peptide having at least 90%, 95%, 96%, 97%, 98% or 99% sequence identity (% SI) with DLTTKLWSSWGYYLG SEQ ID NO 4, and wherein the pharmaceutical composition further comprises at least one antibiotic.

The peptide(s) and the antibiotic act synergistically and enhance the effect of each other.

Provided is a pharmaceutical composition wherein at least 90% of the amino acids in the first peptide and/or second peptide are D-amino acid residues.

Such peptides are more stable and less sensitive to proteolytic cleavage compared to their corresponding L-variants.

Provided is a pharmaceutical composition wherein the antibiotic is selected from the group consisting of antibiotics that inhibit bacterial cell wall synthesis, antibiotics that inhibit nucleic acid synthesis and antibiotics that inhibit protein synthesis.

Provided is a pharmaceutical composition for use in the treatment or prophylaxis of a bacterial infection.

Also provided is the use of a pharmaceutical composition in coating at least part of a device to limit colonization of bacteria on the surface of the device.

BRIEF DESCRIPTION OF THE DRAWINGS

These and other aspects, features and advantages of which the invention is capable of will be apparent and elucidated from the following description of embodiments of the present invention, reference being made to the accompanying drawings, in which FIGS. 1A-1C show PLNC8 αβ markedly inhibits the growth and survival of different strains of S. aureus and S. epidermidis. Different Staphylococcus species were cultured for 20 h in the presence of increasing concentrations of PLNC8 αβ (1:1). S. epidermidis was generally more susceptible to PLNC8 αβ than S. aureus. Minimum inhibitory concentration (MIC) and minimum bactericidal concentration (MBC) for Staphylococcus species in response to PLNC8 αβ.

FIG. 7. (A) Both the L- and D-form of PLNC8 αβ display a low hemolytic activity. Human erythrocytes were incubated with different concentrations (0.5-50 μM) of L- or D-variant of PLNC8 α, β or αβ (1:1) for 1 h. In (B) this is shown for truncated forms α1-15, α1-22, β7-20, β1-20, β7-34.

FIG. 8. Amino acid sequences of truncated peptides of PLNC8 α and PLNC8 β.

FIG. 10. Antimicrobial activities of truncated forms of PLNC8 α. (A) Release of (6)-carboxyfluorescein (CF) from liposomes was obtained with α1-22 and full-length α1-29. When combined with a full length PLNC8 β peptide, effects were also obtained with the other truncated peptides, although at higher concentrations. (C) Amino acid sequences of truncated peptides of L-PLNC8 α. (D) Quantification of 50% CF release by truncated L-PLNC8 α peptides, with and without L-PLNC8 β. (E) Minimum inhibitory concentration (MIC) and minimum bactericidal concentration (MBC) of truncated PLNC8 α against S. epidermidis ATCC 12228. Growth and survival of S. epidermidis was inhibited by α1-29 and α1-22 in combination with the β-peptide.

FIG. 11. Antimicrobial activity of a combination of truncated PLNC8 α and PLNC8 β. Minimum inhibitory concentration (MIC) and minimum bactericidal concentration (MBC) of a combination of truncated PLNC8 α and PLNC8 β against S. epidermidis ATCC 12228. The inhibition of growth and survival of S. epidermidis by β1-20 and β7-20, respectively, was not further enhanced by a co-incubation with α1-22 or α1-15.

FIG. 14. PLNC8 αβ is effective against heterogeneous strains of S. epidermidis. S. epidermidis isolated from prosthetic joint infections, including heterogeneous glycopeptide intermediate S. epidermidis (hGISE), was exposed to L-PLNC8 αβ for 20 h and MIC (minimum inhibitory concentration) and MBC (minimum bactericidal concentration) were determined.

DESCRIPTION OF EMBODIMENTS

Figure 2:
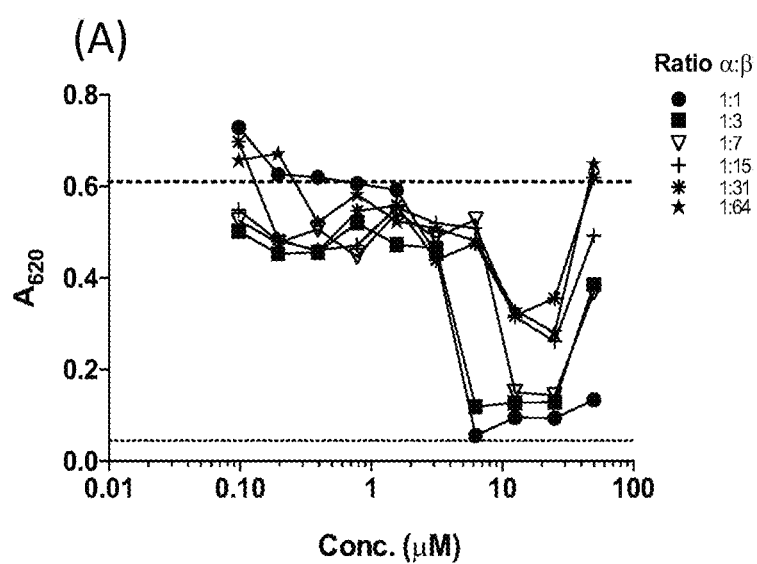
FIGS. 2A and 2B. The molar ratio of PLNC8 α and PLNC8 β is critical for optimal antimicrobial activity. S. epidermidis ATCC 12228 was exposed to different molar ratios of PLNC8 α and β for 20 h. A molar ratio of 1:1 between PLNC8 α and PLNC8 β is most efficient at inhibiting and killing S. epidermidis. Minimum inhibitory concentration (MIC) and minimum bactericidal concentration (MBC) for different molar ratios of PLNC8 α and β. * The highest total concentration of the peptides was kept constant at 50 μM, while the concentrations of PLNC8 α and β individually were altered to obtain different molar ratios.

The following description focuses on an embodiment of the present invention applicable to combating infection, and especially Hospital-acquired infection (HAI) (but also other types of infections) using peptides derived from a L. plantarum NC8 bacteriocin used together with antibiotics. However, it will be appreciated that the invention is not limited to this application but these peptides may be applied to many other uses, including for example disinfection and coating of surfaces.

There are several problems associated with combating infections, such as Hospital-acquired infection (HAI). These include: Inadequate treatment strategies for many severe and serious bacterial infections; Development and spread of antibiotic resistance in health care (e.g. methicillin-resistant Staphylococcus aureus (MRSA) and Staphylococcus epidermidis (MRSE)); Large costs for society for prevention and treatment of infectious diseases (e.g. annual hospital costs of treating healthcare-associated infections (HAIs) in US is estimated to 40 billion dollar and in Sweden to 6.5 billion SEK): Human suffering from infectious diseases (annually approx. 6 million patients with HAIs in US and EU and 150 000 die).

These problem are not trivial to approach, since they include aspects such as intractable infections in the form of biofilms, high proteolytic activity in infections antagonizing the action of antibacterial agents, limited stability and activity of antibacterial agents, chronic infection and inflammation, and slow and complicated wound healing.

It was envisaged by the present inventors that specific Lactobacillus species indeed may be able to contribute to solving these problems, from its ability to suppress pathogens primarily through expression and secretion of certain bacteriocins.

Lactobacillus plantarum is a highly versatile lactic acid bacterium found in saliva and gastrointestinal tract as well as fermented vegetables, meat and dairy products. L. plantarum NC8 has been used as a model strain in many laboratories worldwide, and is a naturally plasmid-free L. plantarum strain. *L. plantarum* NC8 has previously been shown to produce a two-peptide bacteriocin, PLNC8 αβ, classified as a class IIb bacteriocin. The inventors have previously shown that PLNC8 αβ is efficient against the periodontal pathogen *Porphyromonas gingivalis* and stimulates cell proliferation (1,2).

The idea of the invention is to exploit the antibacterial effects of bacteriocin PLNC8αβ, unmodified or truncated, in soluble or immobilized form, together with antibiotics, for the prevention and treatment of acute and chronic infections, such as periodontitis, wound infections, implant-associated infections and urinary tract infections. Products based on bacteriocins in conjunction with traditional antibiotics can be of enormous importance in health care, with improved public health and a positive impact on the social economy.

Since development and spread of antibiotic resistance in health care primarily concerns methicillin-resistant *Staphylococcus aureus* (MRSA) and *Staphylococcus epidermidis* (MRSE), the effect of PLNC8αβ on different strains of *S. aureus* and *S. epidermidis* were studied. As can be seen in FIG. 1 and Table 1, PLNC8αβ markedly inhibited the growth and the survival of all bacterial strains (FIG. 1).

TABLE 1

| Bacteria | Characteristics | | |
|---|---|---|---|
| *S. aureus* ATCC 29213 (MSSA) | Methicillin sensitive | | |
| *S. aureus* CCUG 35601 (MRSA) | Methicillin resistant | | |
| *S. epidermidis* ATCC 12228 | Biofilm negative | | |
| *S. epidermidis* RP62A | Biofilm positive | | |
| *S. epidermidis* N15 | Isolated from nose of a healthy individual | | |
| *S. epidermidis* 117 | Isolated from an infected hip joint prosthesis | | |
| L-PLNC8 αβ | | MIC | MBC |
| *S. aureus* ATCC 29213 (MSSA) | | 12.5 | 25 |
| *S. aureus* CCUG 35601 (MRSA) | | 12.5 | 25 |
| *S. epidermidis* ATCC 12228 | | 6.25 | 12.5 |
| *S. epidermidis* RP62A | | 6.25 | 6.25 |
| *S. epidermidis* N15 | | 6.25 | 6.25 |
| *S. epidermidis* 117 | | 12.5 | 12.5 |

Figure 15:
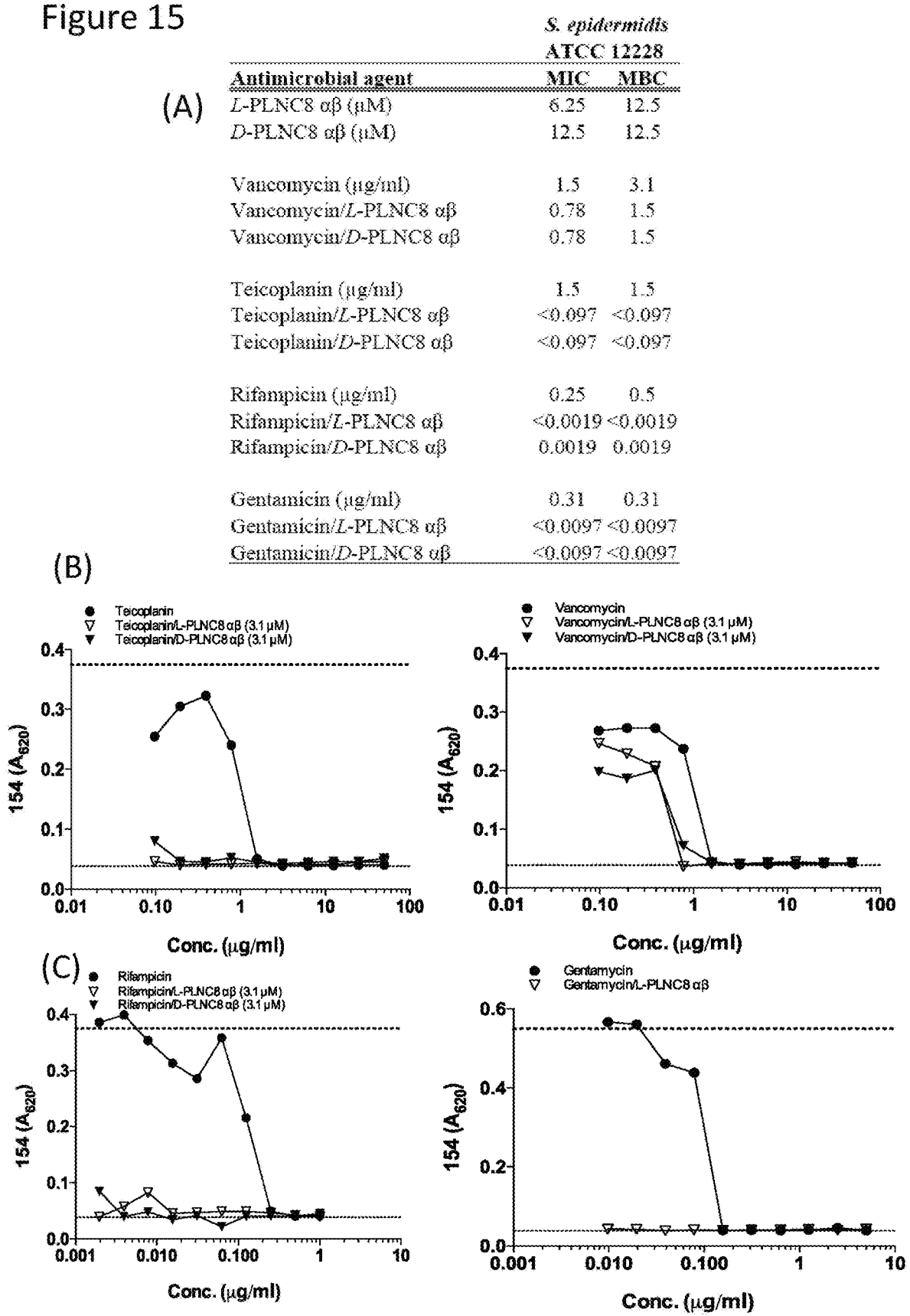
FIGS. 15A-15C. PLNC8 αβ acts synergistically with antibiotics. Synergistic antimicrobial effects between antibiotics and L- or D-PLNC8 αβ. S'. epidermidis (strain 154) was exposed to L-PLNC8 αβ or D-PLNC8 αβ (3.1 μM), a serial dilution of teicoplanin, vancomycin, rifampicin and gentamicin, alone or in their combination with 3.1 µM L-PLNC8 αβ or D-PLNC8 αβ.

Further, it was probed if the antimicrobial effect could be enhanced using combination therapy. In combination therapy, combinations of antimicrobial agents are utilized for the prevention of the development of resistance and to shorten the length of treatment time. It was investigated whether combinations of PLNC8 αβ together with different traditional antibiotics would be effective in the treatment of *S. epidermidis*. In FIG. 15, results are summarized for PLNC8 αβ together with rifampicin, vancomycin, gentamicin or teicoplanin. Here it was surprisingly found that PLNC8 αβ decreased MIC (minimum inhibitory concentration) and MBC (minimum bactericidal concentration) of teicoplanin more than 15-fold against *S. epidermidis* (FIG. 15). A combination of PLNC8 αβ and rifampicin was found to be even more effective.

MIC (minimum inhibitory concentration) and MBC (minimum bactericidal concentration) of rifampicin was lowered more than 100-fold when treating *S. epidermidis* in the presence of L-PLNC8 αβ or D-PLNC8 αβ. Furthermore, L-PLNC8 αβ decreased MIC and MBC of gentamicin 15-30 fold against *S. epidermidis*. L-PLNC8 αβ or D-PLNC8 αβ lowered MIC and MBC of vancomycin 2-fold. (FIG. 15 and Table 2).

TABLE 2

Antimicrobial effect is enhanced using PLNC8 αβ combination therapy.

| | *S. epidermidis* ATCC 12228 | |
|---|---|---|
| Antimicrobial agent | MIC | MBC |
| Z-PLNC8 αβ (μM) | 6.25 | 12.5 |
| D-PLNC8 αβ (μM) | 12.5 | 12.5 |
| Vancomycin (μg/ml) | 1.5 | 3.1 |
| Vancomycin/L-PLNC8 αβ | 0.78 | 1.5 |
| Vancomycin/D-PLNC8 αβ | 0.78 | 1.5 |
| Teicoplanin (μg/ml) | 1.5 | 1.5 |
| Teicoplanin/L-PLNC8 αβ | <0.097 | <0.097 |
| Teicoplanin/D-PLNC8 αβ | <0.097 | <0.097 |
| Rifampicin (μg/ml) | 0.25 | 0.5 |
| Rifampicin/L-PLNC8 αβ | <0.0019 | <0.0019 |
| Rifampicin/D-PLNC8 αβ | 0.0019 | 0.0019 |
| Gentamicin (μg/ml) | 0.31 | 0.31 |
| Gentamicin/L-PLNC8 αβ | <0.0097 | <0.0097 |
| Gentamicin/D-PLNC8 αβ | <0.0097 | <0.0097 |

This showed a surprisingly strong synergistic effect, with up to hundred fold decrease of MIC and MBC of the antibiotic against specific bacteria. Without being bound to theory, this may be due to the membrane permeabilizing effect of PLNC8 αβ, which may damage bacterial membranes and thus facilitate passage for the antibiotics, which thus more easily reach their intracellular targets (e.g., ribosomes, RNA polymerase). The consequence is that the concentration of antibiotics can be significantly lowered with reduced problems of both antibiotic resistance and cytotoxic side effects.

Figure 23:
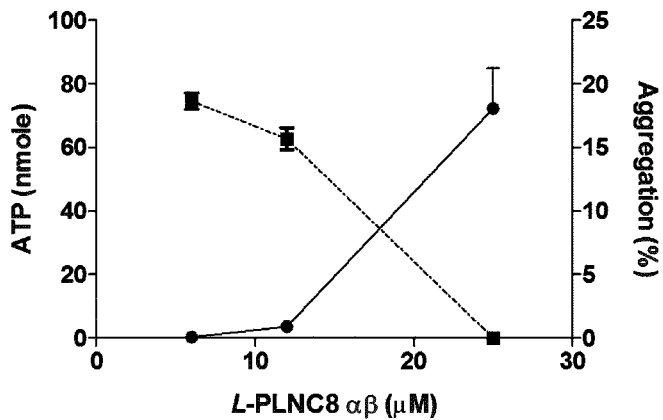

The membrane permeabilizing effect is shown in FIG. 23, where L-PLNC8 αβ effectively lyses *S. epidermidis*, which is demonstrated by a dose-dependent release of ATP. It is also demonstrated that bacteria aggregates when exposed to low concentrations of L-PLNC8 αβ. Also, in FIG. 24, it is shown that that PLNC8 αβ causes rapid membrane permeabilization of liposomes. PLNC8 β and PLNC8 αβ (1:1), but not PLNC8 α, of both the L-form and D-form, caused complete lysis of liposomes after 2 min.

The synergistic antimicrobial effect between PLNC8 αβ and traditional antibiotics against resistant strains of *Staphylococcus* is shown in table 3 below. Here the effects of vancomycin or teicoplanin combined with L-PLNC8 αβ against methicillin-resistant *Staphylococcus aureus* (MRSA) and methicillin-resistant *Staphylococcus epidermidis* (MRSE) are shown.

Figure 25:
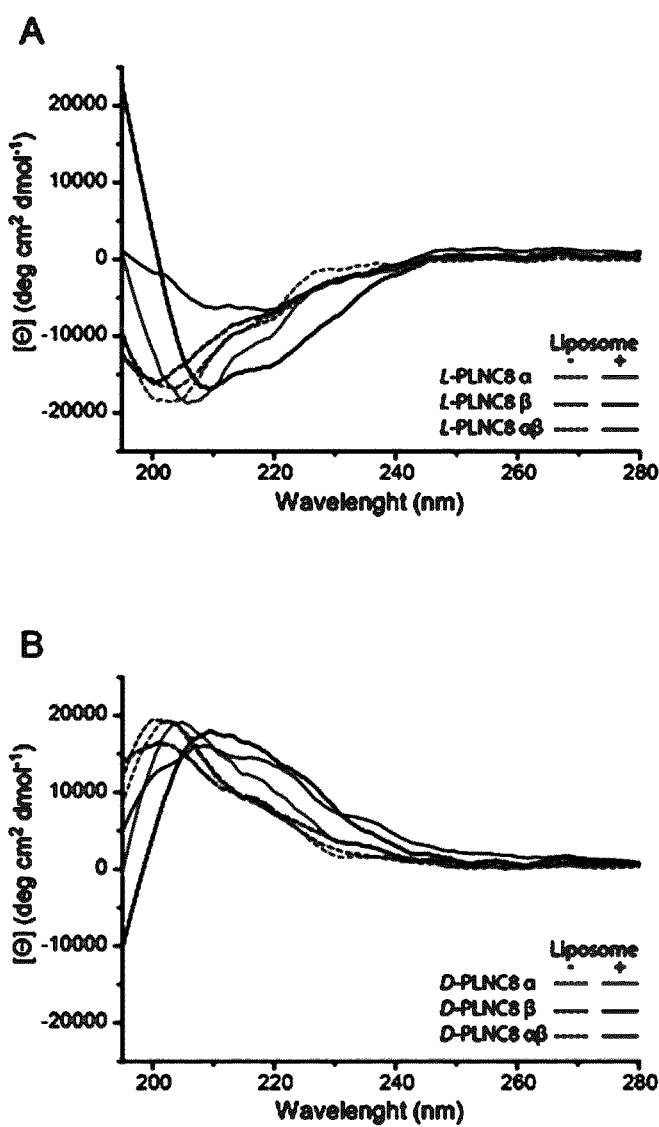

In FIG. 25, CD-spectroscopy shows that both L- and D-PLNC8 αβ has an ordered secondary structure in liposomes, which indicates that the α-helices are arranged in a definite order for the peptide to be active.

TABLE 3

Synergistic antimicrobial effect between PLNC8 αβ and traditional antibiotics against resistant strains of *Staphylococcus*.

| | MRSA | | S. epidermidis | | | | | |
| | | | 154 | | 126* | | 157* | |
| Antimicrobial agent | MIC | MBC | MIC | MBC | MIC | MBC | MIC | MBC |
|---|---|---|---|---|---|---|---|---|
| L-PLNC8 αβ (μM) | 12.5 | 25 | 6.25 | 12.5 | 12.5 | 50 | 12.5 | >50 |
| Vancomycin (μg/ml) | 1.5 | 3.1 | 1.5 | 3.1 | 3.1 | 3.1 | 6.25 | 6.25 |
| Vancomycin/L-PLNC8 αβ (10 μM) | <0.097 | 0.39 | <0.097 | <0.097 | <0.097 | 0.78 | 6.25 | 6.25 |
| Vancomycin/L-PLNC8 αβ (5 μM) | <0.097 | 0.78 | <0.097 | <0.097 | <0.097 | 0.78 | 6.25 | 6.25 |
| Teicoplanin (μg/ml) | 0.78 | 3.1 | 1.5 | 1.5 | 3.1 | 6.25 | 12.5 | 25 |
| Teicoplanin/L-PLNC8 αβ (10 μM) | <0.097 | 0.39 | <0.097 | <0.097 | <0.097 | 0.39 | 12.5 | 25 |
| Teicoplanin/L-PLNC8 αβ (5 μM) | <0.097 | 0.78 | <0.097 | <0.097 | <0.097 | 0.39 | 12.5 | 25 |

*hGISE strains

This shows that combination therapy with PLNC8 αβ and antibiotics is an efficient treatment strategy. This was further shown during trials using ESKAPE pathogens and *Escherichia coli*, one of the leading causes of nosocomial infections throughout the world. The acronym ESKAPE includes six pathogenic bacterial species (*Enterococcus faecium, Staphylococcus aureus, Klebsiella pneumoniae, Acinetobacter baumannii, Pseudomonas aeruginosa* and *Enterobacter*). These bacteria have become resistant to multiple antibiotics and are associated with higher rates of morbidity and mortality, indicating the need for new strategies to prevent and treat these types of infections. ESKAPE pathogens are prioritized by WHO to promote research and development of new antimicrobials, since multidrugresistance is a serious threat to global public health. Infections caused by these pathogens are often hospital-acquired, and pose a particular threat to patients requiring medical devices, such as catheters, ventilators and implants.

As can be seen in table 4, PLNC8αβ alone does not affect the growth of *E. coli*, however a sub-MIC concentration of the peptides significantly enhanced the effects of different antibiotics.

Similarly, PLNC8αβ alone is both inhibitory and bactericidal against *Enterococcus faecium*, and addition of sub-MIC concentrations significantly enhanced the effects of different antibiotics. This is shown in table 5 below.

Also, in table 6, it is shown that although PLNC8αβ alone does not affect the growth of *Pseudomonas aeruginosa*, addition of sub-MIC concentration of the peptides enhanced the effects of different antibiotics.

TABLE 4

PLNC8αβ markedly enhances the inhibitory and bactericidal effects of antibiotics against *Escherichia coli*

| | Non-ESBL E. coli | | Non-ESBL E. coli | | ESBL-producing E. coli | | ESBL-producing E. coli | |
| Antimicrobial agent | MIC | MBC | MIC | MBC | MIC | MBC | MIC | MBC |
|---|---|---|---|---|---|---|---|---|
| PLNC8αβ (μM) | >50 | >50 | >50 | >50 | >50 | >50 | >50 | >50 |
| Gentamicin | 1.56 | 1.56 | 1.56 | 3.125 | >50 | >50 | 3.125 | 6.25 |
| Gentamicin/PLNC8αβ* | 0.78 | 0.78 | 0.195 | 0.195 | >50 | >50 | <0.097 | <0.097 |
| Rifampicin | 6.25 | 12.5 | 6.25 | 25 | 12.5 | 12.5 | 12.5 | 12.5 |
| Rifampicin/PLNC8αβ* | 0.78 | 1.56 | 1.56 | 1.56 | <0.097 | 0.195 | <0.097 | 0.195 |
| Ciprofloxacin | 0.0125 | 0.0125 | 0.00625 | 0.00625 | >0.1 | >0.1 | >0.1 | >0.1 |
| Ciprofloxacin/PLNC8αβ* | 0.0125 | 0.0125 | 0.00078 | 0.0015 | <0.00019 | <0.00019 | 0.00078 | 0.00078 |
| Teicoplanin | >50 | >50 | >50 | >50 | >50 | >50 | >50 | >50 |
| Teicoplanin/PLNC8αβ* | >50 | >50 | >50 | >50 | <0.097 | <0.097 | <0.097 | <0.097 |

*Peptide concentration in combination with antibiotics is 10 μM

TABLE 5

PLNC8αβ markedly enhances the inhibitory and bactericidal effects of antibiotics against *Enterococcus faecium*.

| | E. faecium | | E. faecium | | Vancomycin resistant E. faecium (VRE) | |
| Antimicrobial agent | MIC | MBC | MIC | MBC | MIC | MBC |
|---|---|---|---|---|---|---|
| PLNC8αβ (μM) | 6.25 | 6.25 | 3.1 | 6.25 | 3.1 | 25 |
| Gentamicin | 50 | >50 | 50 | 50 | >50 | >50 |
| Gentamicin/PLNC8αβ* | 3.1 | 3.1 | 1.5 | 1.5 | >50 | >50 |
| Rifampicin | >50 | >50 | 25 | >50 | <0.097 | 3.1 |
| Rifampicin/PLNC8αβ* | 50 | >50 | 12.5 | 25 | <0.097 | <0.097 |
| Ciprofloxacin | >50 | >50 | >50 | >50 | >50 | >50 |

TABLE 5-continued

PLNC8αβ markedly enhances the inhibitory and bactericidal effects of antibiotics against *Enterococcus faecium*.

| Antimicrobial agent | E. faecium | | E. faecium | | Vancomycin resistant E. faecium (VRE) | |
|---|---|---|---|---|---|---|
| | MIC | MBC | MIC | MBC | MIC | MBC |
| Ciprofloxacin/PLNC8αβ* | <0.097 | <0.097 | <0.097 | <0.097 | <0.097 | 25 |
| Teicoplanin | >50 | >50 | 0.39 | 25 | 0.39 | 50 |
| Teicoplanin/PLNC8αβ* | >50 | >50 | <0.097 | <0.097 | <0.097 | 0.39 |

*Peptide concentration in combination with antibiotics is 1.5 μM

TABLE 6

PLNC8αβ markedly enhances the inhibitory and bactericidal effects of antibiotics against *Pseudomonas aeruginosa*.

| Antimicrobial agent | P. aeruginosa | | P. aeruginosa | |
|---|---|---|---|---|
| | MIC | MBC | MIC | MBC |
| PLNC8αβ (μM) | >50 | >50 | >50 | >50 |
| Levofloxacin | 1 | 2 | 4 | 4 |
| Levofloxacin/PLNC8αβ* | 0.25 | 0.25 | 0.013 | 0.12 |
| Meropenem | 25 | 50 | 25 | 25 |
| Meropenem/PLNC8αβ* | 0.19 | 0.39 | 0.39 | 0.78 |
| Ciprofloxacin | 0.25 | 0.25 | 0.016 | 0.016 |
| Ciprofloxacin/PLNC8αβ* | 0.5 | 1 | 0.016 | 0.063 |

*Peptide concentration in combination with antibiotics is 15 μM

Many hospital-acquired bacterial infections are found in superficial infections and severe infections associated with chronic wounds and insertion of medical devices, including catheters and prosthetic joint implants. This may subsequently increase the risk for development of life-threatening conditions, such as sepsis.

Keratinocytes constitute the predominant cell type in the epidermis. Although the primary function of keratinocytes is forming a physical barrier against microorganisms, these cells also participate in the initiation of an inflammatory response against invading microorganisms.

Figure 18:
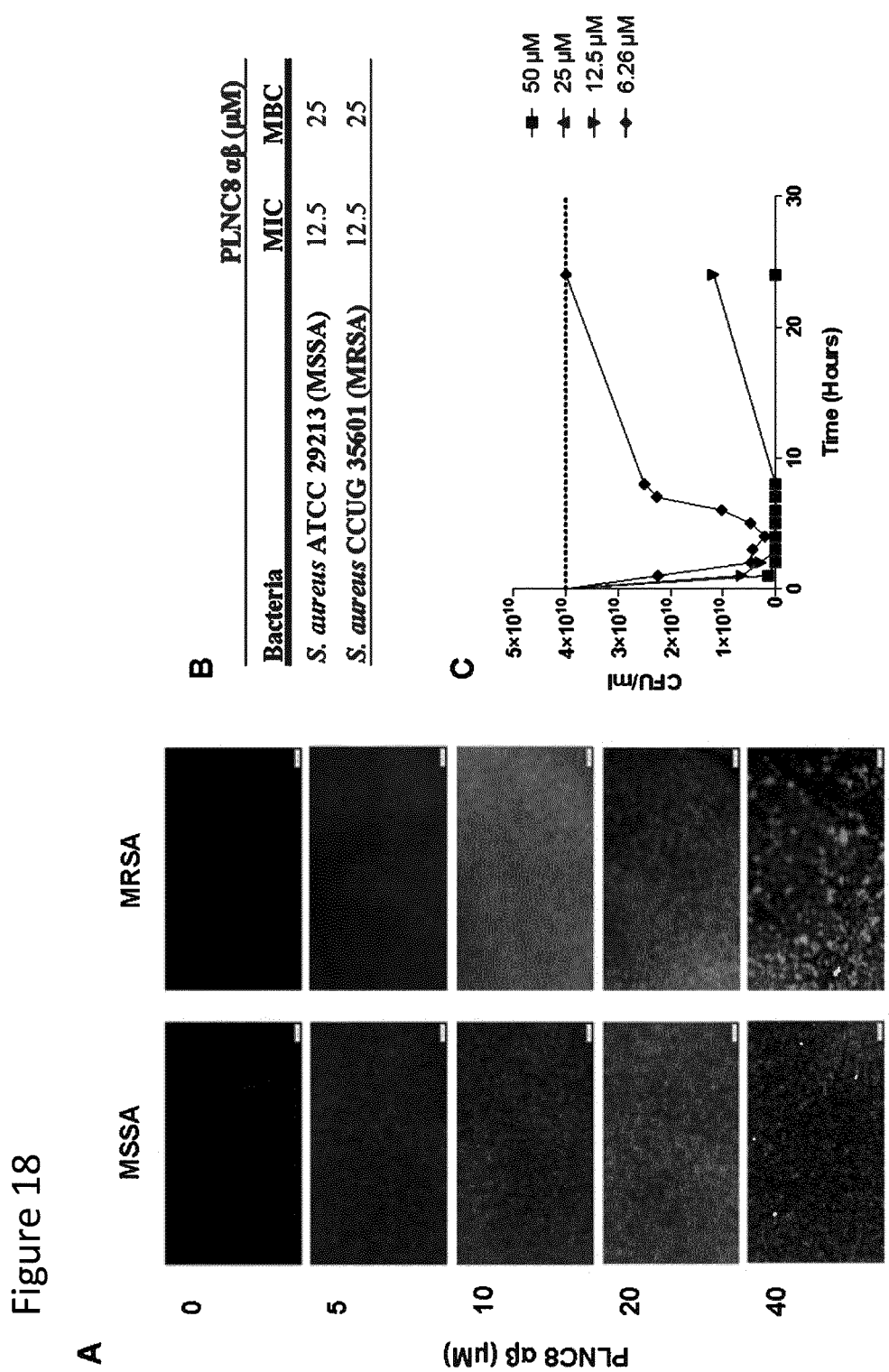
FIG. 18. PLNC8 αβ causes rapid lysis of S. aureus, independent of their resistance to antibiotics. (A) Dose-dependent increase in bacterial lysis, as indicated by Sytox green staining, following exposure to PLNC8 αβ for 5 min. (B) MIC and MBC values for MSSA and MRSA are indicated. (C) Time-kill assay indicated that PLNC8 αβ rapidly kills the bacteria in a dose-dependent manner, FIG. 19. PLNC8 αβ promotes wound healing of human keratinocytes. HaCaT cells were exposed to different concentrations of PLNC8 αβ or MSSA for 24 h. (A) PLNC8 αβ promoted wound healing, which was determined in vitro using scratch assay. While (B) IL-6 and (C) CXCL8 were increased by S. aureus, these inflammatory mediators were not altered by PLNC8 αβ, FIG. 20. PLNC8 αβ antagonizes S. aureus-mediated cytotoxicity and inflammatory responses of human keratinocytes. HaCaT cells were infected with MSSA for 1 h followed by addition of PLNC8 αβ for 6 h. (A) PLNC8 αβ antagonized S. aureus-mediated cytotoxicity, which was determined by LDH activity, and promoted cell viability. Secretion of (B) IL-6 and (C) CXCL8 were significantly reduced by the peptides. (D) Gene expression analysis of il-6 and cxcl8 confirmed the effects of PLNC8 αβ by preventing infection of keratinocytes by S. aureus. Furthermore, intracellular signaling events involves c-jun and c-fos, suggesting a role for the transcription factor AP-1 via MAPK, FIG. 21. PLNC8 αβ promotes wound healing and reduces inflammatory responses of human keratinocytes. HaCaT cells were infected with MSSA, in the presence or absence of PLNC8 αβ for 24 h. (A) PLNC8 promotes wound healing following an infection with S. aureus. The increased secretion of (B) IL-6 and (C) CXCL8 by S. aureus was significantly reduced by the peptides, FIG. 22. PLNC8αβ inhibits infection and promotes wound healing in vivo. Wound healing was evaluated in vivo using a porcine wound healing model. Wounds were either left un-exposed or infected with S. aureus ($10^8$ CFU/ml) for 3 days. Gentamicin (100 µg/ml) and/or PLNC8αβ (50 µM) were added once every other day and the wounds were monitored for 7 days (a total of 4 doses). The peptide, alone or in combination with gentamicin, antagonized the infection and promoted wound healing, FIG. 23. Aggregation (dotted line) and ATP release (solid line) were recorded to determine bacterial lysis by L-PLNC8 αβ, FIG. 24. PLNC8 αβ causes rapid membrane permeabilization on liposomes. PLNC8 β and PLNC8 αβ (1:1), but not PLNC8 α, of both the (A) L-form and (B) D-form, caused complete lysis of liposomes after 2 min, FIG. 25. CD-spectroscopy of PLNC8 αβ. CD measurements of (A) L-PLNC8 αβ and (B) D-PLNC8 αβ (100 µM each) without (dashed) and with (solid) liposomes (0.5 mg/ml, ~660 µM) in PBS. Three repeats with PBS as background. Liposome containing samples were incubated for at least 30 min prior to measurements, FIG. 26. IncuCyte live-cell analysis of infected keratinocytes, in the presence or absence of PLNC8 αβ S. aureus MOI:1 caused cell death after 8 h. A single dose of PLNC8 αβ prevented bacterial growth and protected the cells for up to 32 h. The combination PLNC8 αβ/gentamicin (5 µg/ml) efficiently eliminated S. aureus and prevented an infection, and subsequent cell death, over the entire experimental period (72 h), and FIG. 27. IncuCyte live-cell analysis of infected keratinocytes, in the presence or absence of PLNC8 αβ A—S. aureus MOI:0.1 caused cell death after 10 h. A single dose of PLNC8 αβ prevented bacterial growth and protected the cells for up to 42 h. The combination PLNC8 αβ/gentamicin (5 µg/ml) efficiently eliminated S. aureus and prevented an infection, and subsequent cell death, throughout the entire experimental period (72 h). B—Bacterial growth, measured by quantifying GFP fluorescence of the bacteria, reached maximum levels after 8-9 h. PLNC8 αβ prevented and delayed bacterial growth up to 38 h, and the combination PLNC8 αβ/gentamicin efficiently eliminated all the bacteria.

In FIG. 18, it is shown that PLNC8αβ is inhibitory and bactericidal against *S. aureus*, independent of their irresistance patterns against antibiotics.

Figure 19:
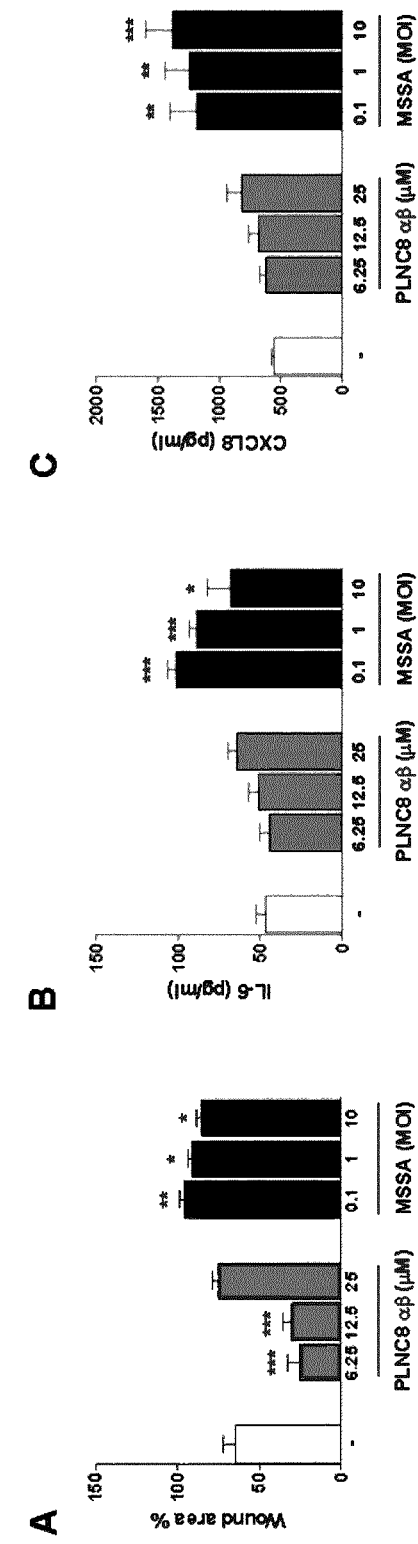

In FIG. 19, It is shown that PLNC8 αβ promotes wound healing of human keratinocytes, which was determined in vitro using scratch assay. While *S. aureus* increased IL-6 and CXCL8, these inflammatory mediators were not altered by PLNC8 αβ.

Figure 20:
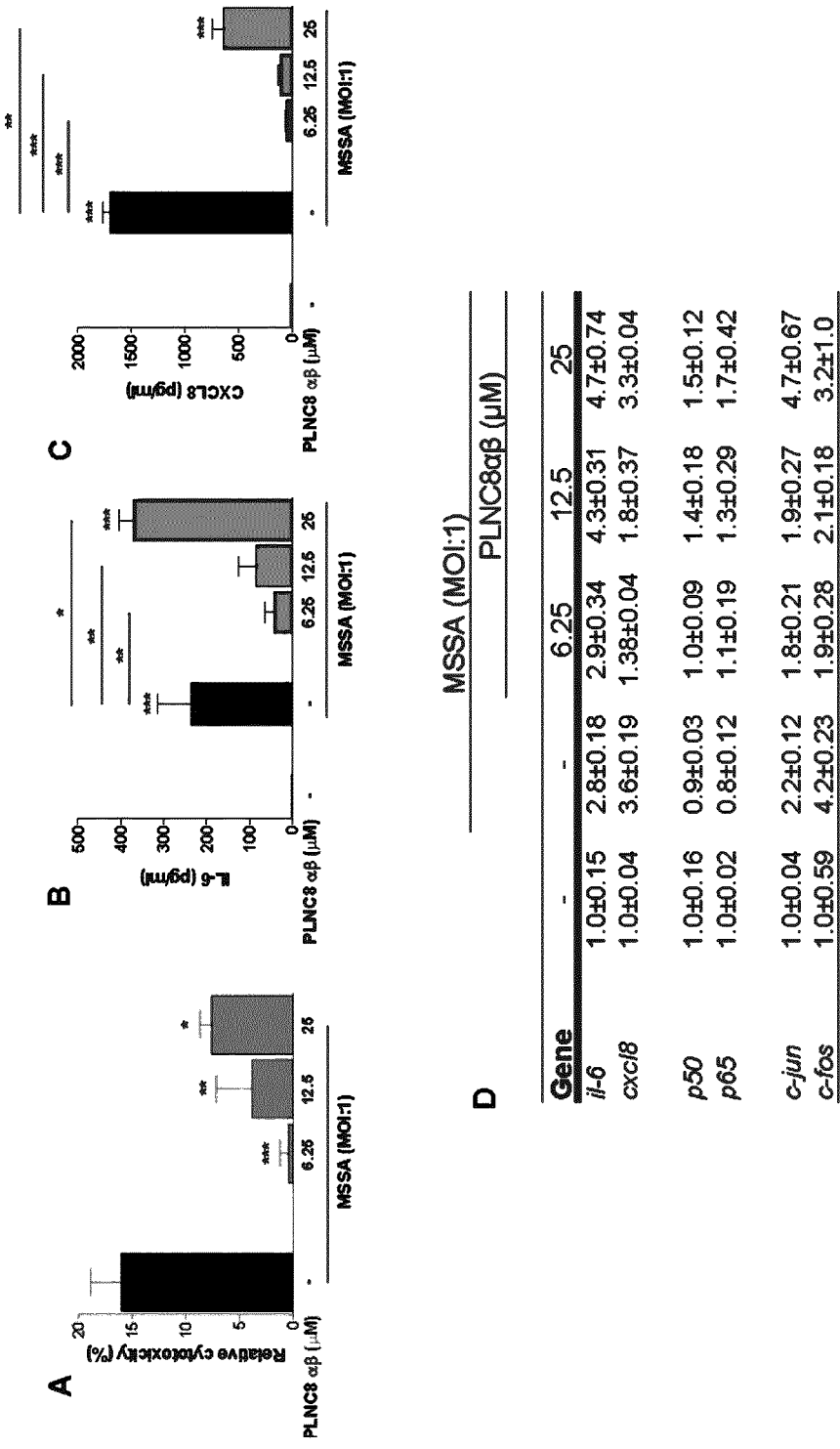

In FIG. 20, it is shown that the peptides efficiently counteract the cytotoxic and inflammatory effects of *S. aureus* on human keratinocytes.

Figure 21:
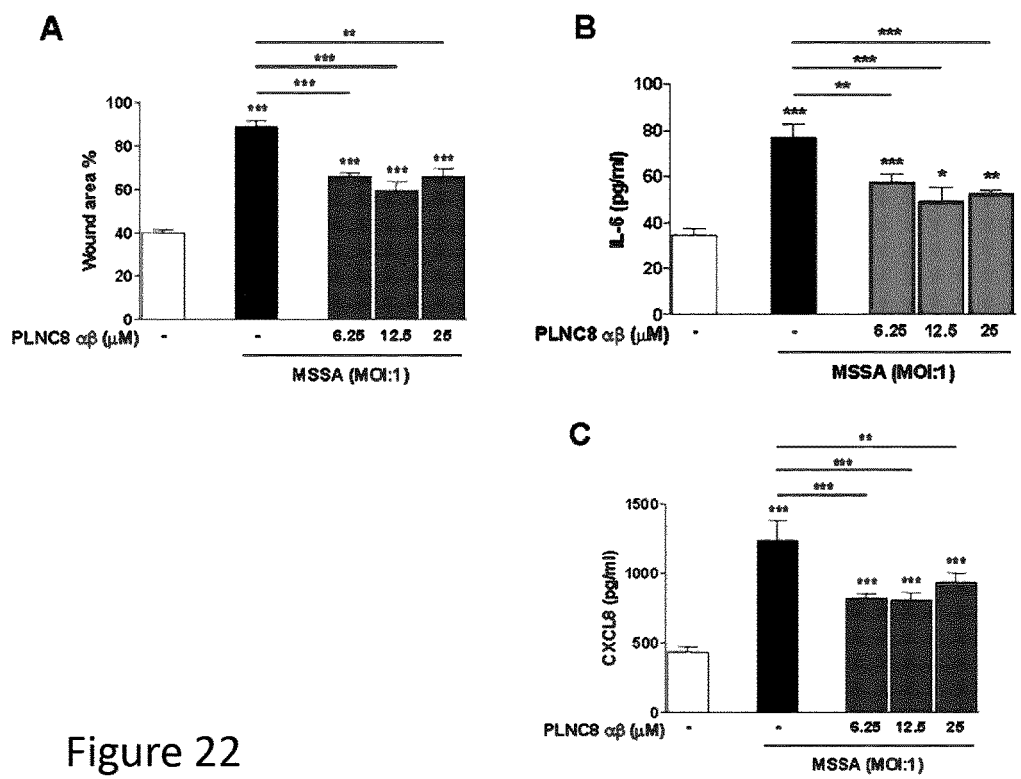

The infected cells are damaged which leads to increased secretion of IL-6 and CXCL8. Here, a significant reduction of these secretions can be attributed to the peptides. In FIG. 21, it is shown that PLNC8 promotes wound healing following an infection with *S. aureus*.

Figure 22:
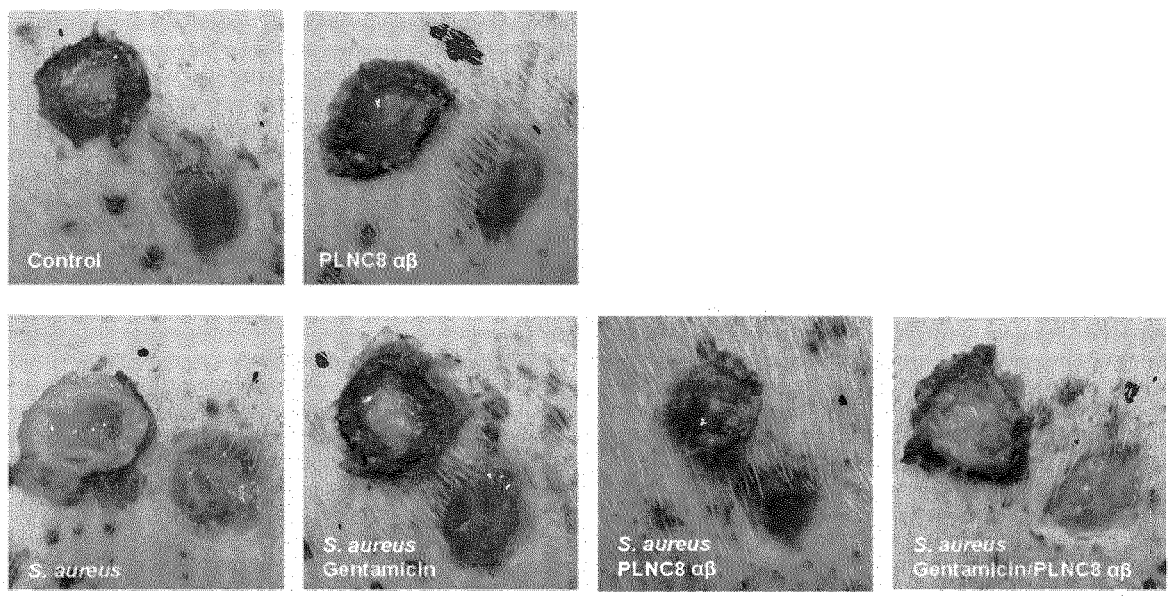

Using a porcine wound healing model, it was also shown that PLNC8αβ inhibits infection and promotes wound healing in vivo. In FIG. 22, the peptide, alone or in combination with gentamicin, antagonized the infection by *S. aureus* and promoted wound healing.

Figure 26:
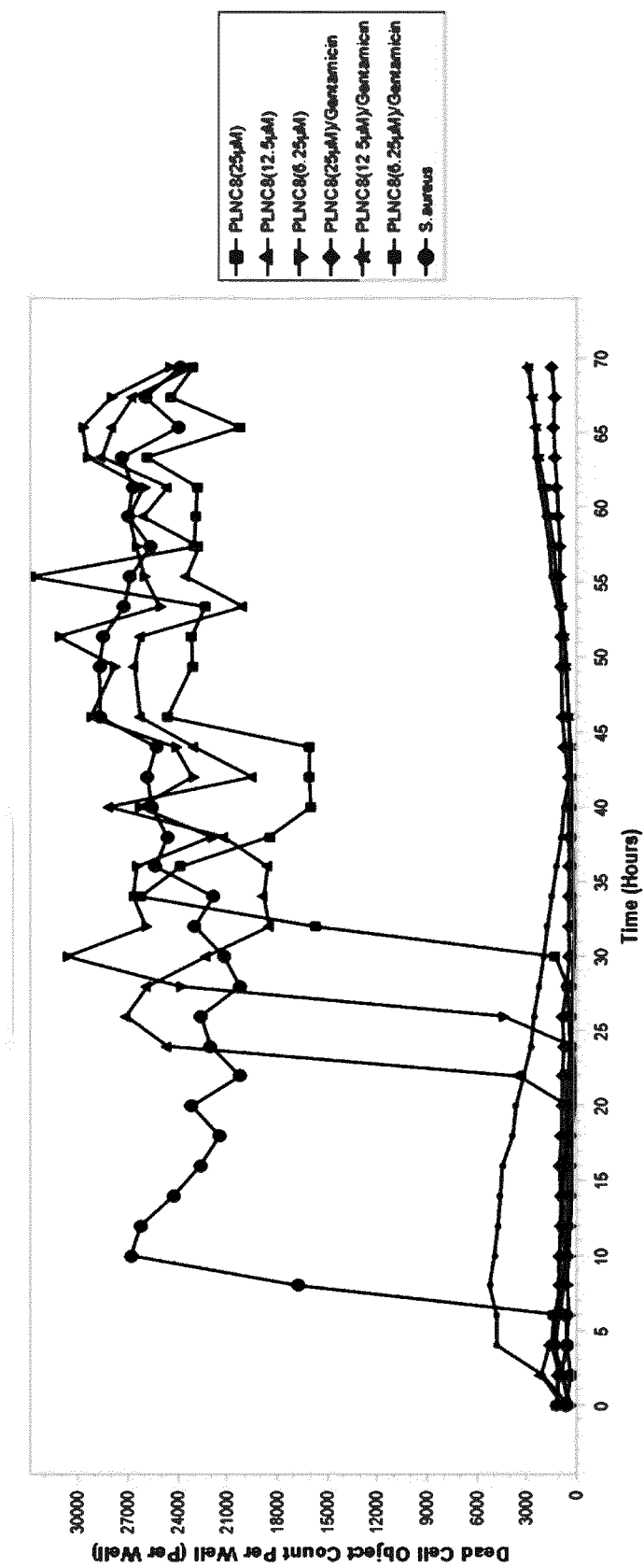

In FIG. 26, IncuCyte live-cell analysis of keratinocytes infected by *S. aureus*, (MOI:1) in the presence or absence of PLNC8 αβ. A single dose of PLNC8 αβ prevented bacterial growth and protected the cells for up to 32 h. Bacterial growth without peptides reached maximum levels after 8-9 h. The combination PLNC8 αβ/gentamicin (5 μg/ml) efficiently eliminated *S. aureus* and prevented an infection, and subsequent cell death, over the entire experimental period (72 h).

FIG. 27. IncuCyte live-cell analysis of keratinocytes infected by *S. aureus*, (MOI:0.1) in the presence or absence of PLNC8 αβ. A single dose of PLNC8 αβ prevented bacterial growth and protected the cells for up to 42 h. Bacterial growth without peptides reached maximum levels after 10 h. The combination PLNC8 αβ/gentamicin (5 μg/ml) efficiently eliminated *S. aureus* and prevented an infection, and subsequent cell death, through out the entire experimental period (72 h).

Another aspect of bacterial defense against antibiotics is the formation of bacterial biofilms. The bacterial biofilms seem to create resistance to antibiotics, disinfectant chemicals and to phagocytosis and other components of the innate and adaptive inflammatory defense system. As such, it is vital that a treatment can combat the formation of bacterial biofilms but also disrupt an already existing biofilm.

Therefore, the bacteriocins were not only tested using bacteria in a planktonic state, but also using biofilms consisting of *S. epidermidis*. It was found that PLNC8 αβ efficiently disrupted the biofilms and killed the bacteria (shown in FIG. 3). Also, the α and β peptide of PLNC8 exerted by themselves, although at higher concentrations, disruptive effects on the biofilms.

A biofilm is a structured consortium of bacteria embedded in a self-produced polymer matrix consisting of polysaccharides, protein and extracellular DNA. Gradients of nutrients and oxygen exist from the top to the bottom of biofilms and the bacterial cells located in nutrient poor areas have decreased metabolic activity and increased doubling times. These more or less dormant cells are therefore responsible for some of the tolerance to antibiotics. Thus, it is of importance that the antimicrobial agent can penetrate the biofilm to expose the biofilm bacteria to the antibiotic or antimicrobial agent and there exert antibacterial effect.

However, indications are that e.g. *Staphylococcus* biofilms are not totally impervious to antibiotics, and certain fluorescently tagged antimicrobials (such as daptomycin) have been shown to penetrate the biofilms of *S. aureus* and *S. epidermidis* by diffusion.

In the invention, it was hypothesized that the biofilm penetration of PLNC8 αβ could be increased through modifying the bacteriocins. Thus, truncated forms of PLNC8 αβ were developed. These shortened forms of the bacteriocins diffuse more rapidly into the biofilm due to their limited size. It was then investigated whether these truncated forms express antibacterial activities similar to the native bacteriocin or if they are even more effective.

Figure 9:
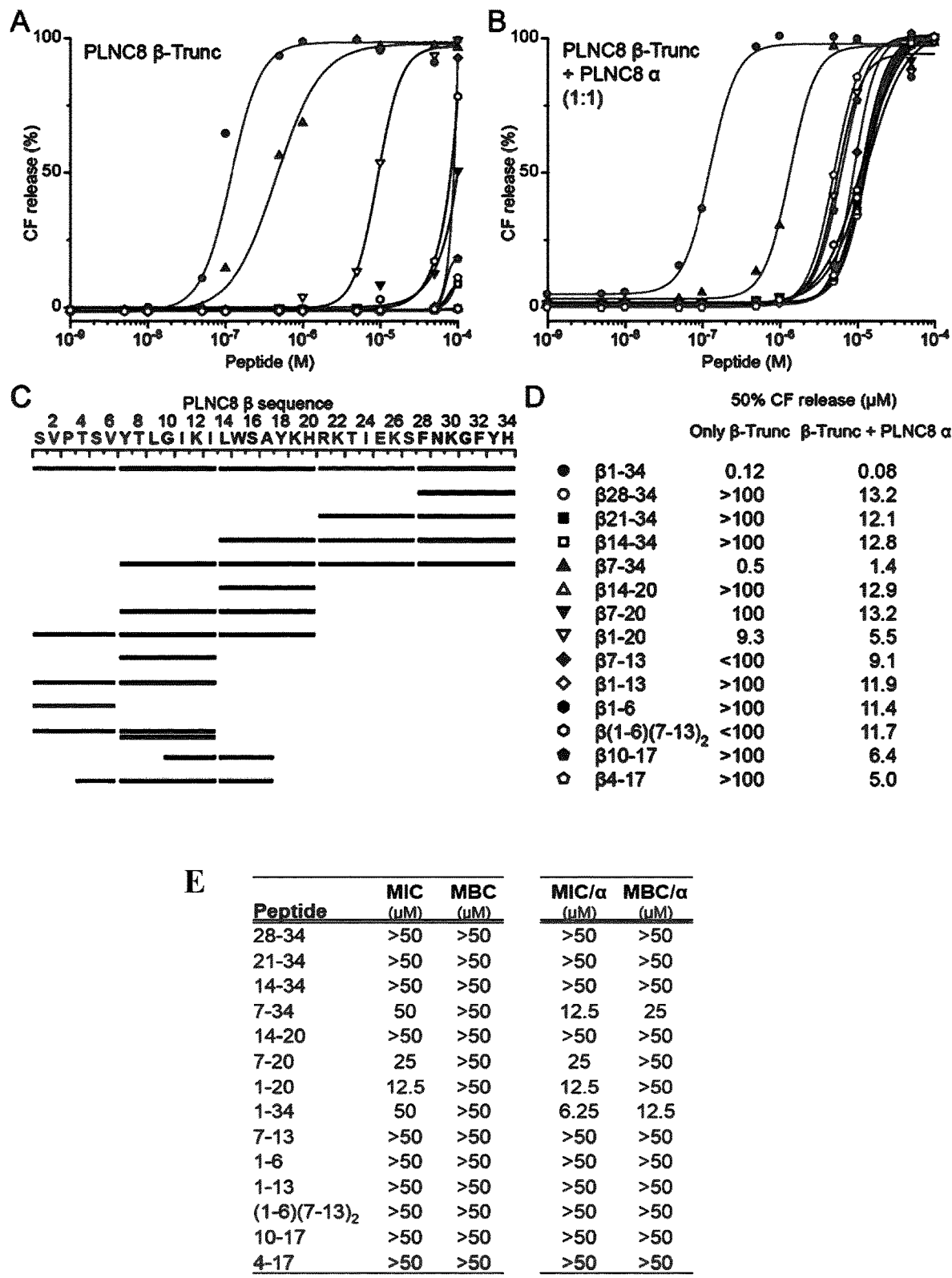
FIG. 9. Antimicrobial activities of truncated forms of PLNC8 β. In A. disruption of the membrane and release of (6)-carboxyfluorescein (CF) from liposomes was obtained with the β-peptides 1-34 (full-length), 7-34, 1-20 and 7-20. In B. when combined with a full length PLNC8 α peptide, effects were also obtained with the other truncated peptides, although at higher concentrations. In C, amino acid sequences of truncated peptides of L-PLNC8 β. In D, quantification of 50% CF release with truncated L-PLNC8 β, with and without L-PLNC8 α. In E, minimum inhibitory concentration (MIC) and minimum bactericidal concentration (MBC) of truncated PLNC8 β, in the absence or presence of full-length α-peptide, against S. epidermidis ATCC 12228. Growth of S. epidermidis was inhibited by the full-length β1-34, β7-34, β1-20 and β7-20.

Truncated peptides of PLNC8 α and PLNC8 β, respectively, were constructed in sequences of 6-7 amino acids, to correspond to the number of amino acids required for formation of an alpha helix (shown in FIG. 8). The effects of truncated PLNC8 α and PLNC8 β were tested on both a liposome system (resembling bacteria) and on *S. epidermidis*. Disruption of the liposome membranes, revealed by release of (6)-carboxyfluorescein (CF), was obtained with the β-peptides 1-34 (full-length), 7-34, 1-20 and 7-20 (FIG. 9). When combined with a full length PLNC8 α peptide, effects were also obtained with the other truncated peptides, although at higher concentrations. As such, it was surprisingly found that growth of *S. epidermidis* was most efficiently inhibited by sequence β1-20 and β7-20, respectively, and these truncated peptides were as effective, or even more effective, than the full-length native PLNC8 β (1-34) (FIG. 9).

It was further found that the peptide β-sequences β7-13 and β14-20 are crucial for the effects of PLNC8 β and are more efficient when combined with β1-6. Thus, the peptide β1-20 is most effective in inhibiting *S. epidermidis*. Furthermore, it was found that the effects of β1-20 and β7-20 were not further enhanced in combination with the full-length α-peptide.

The antimicrobial activities of truncated forms of PLNC8 α were further probed, as shown in FIG. 10 and Table 2. The truncated form 1-22 of the α-peptide and the full-length α-peptide (1-29) disrupted the membrane of the liposomes, revealed by a release of carboxyfluorescein. In combination with the β-peptide, α1-22 exerted inhibitory and bactericidal effects on *S. epidermidis* (FIG. 10).

A combination of truncated α1-22 or α1-15 with β1-20 or β7-20 and the effect on MIC and MBC against *S. epidermidis* is shown in FIG. 11. α1-22 and α1-15 did not further enhance the inhibitory effects of β1-20 and β7-20.

As such, the innovation pertains to a combination of PLNC8 αβ and antibiotics for synergistic effects, with several fold decrease of MIC and MBC of the antibiotic against specific bacteria. Furthermore, by truncating PLNC8 αβ) to shorter α and β peptides (e.g. α1-22, β1-20 and β7-20), synergistic antibacterial properties are retained, while higher diffusion rates in bacterial biofilms are obtained. This since the diffusion coefficients increase strongly as the system size increases. In a gel, such as a bacterial biofilm, diffusion is even more affected by particle size, since larger particles will also have a higher risk of becoming entrapped in pores of the gel.

Thus, in one embodiment, a pharmaceutical composition comprising a first and a second peptide, wherein the first peptide is a peptide of PLNC8 αβ, wherein the peptide of PLNC8 αβ is a peptide A having at least 90%, 95%, 96%, 97%, 98% or 99% sequence identity (% SI) with DLTTKLWSSWGYYLGKKARWNLKHPYVQF, (SEQ ID NO 1) or a peptide B having at least 90%, 95%, 96%, 97%, 98% or 99% sequence identity (% SI) with SVPTSVYTLGIKILWSAYKHRKTIEKSFNKGFYH (SEQ ID NO 2), and wherein when the first peptide is peptide A, the second peptide B' having 14 to 34 amino acids and comprising a peptide having at least 90%, 95%, 96%, 97%, 98% or 99% sequence identity (% SI) with YTLGIKILWSAYKH (SEQ ID NO 3), when the first peptide is peptide B, the second peptide A' having 15 to 29 amino acids and comprising a peptide having at least 90%, 95%, 96%, 97%, 98% or 99% sequence identity (% SI) with DLTTKLWSSWGYYLG (SEQ ID NO 4), and wherein the pharmaceutical composition further comprises at least one antibiotic.

Thus, according to the invention, a composition comprising a combination of full length α and truncated or full length β together with antibiotics or full length β and truncated or full length α together with antibiotics or full length α and full length β provide a surprisingly high antimicrobial effect as can be seen in Table 2 (high synergistic effects, with several fold decrease of MIC and MBC). Furthermore, the combinations comprising truncated α and/or β also has the advantage of higher diffusion rates resulting in better activity effect against bacterial biofilms.

According to one embodiment peptide B' has at least 90%, 95%, 96%, 97%, 98% or 99% sequence identity (% SI) with an amino acid sequence selected from the group consisting of SEQ ID NO 5, 6, 7, 8, 9, 10, 11, 12, 13, 14, 15, 16, 17, 18, 19, 20, 21, 22, 23, 24, and 2.

In one embodiment, peptide B' is a sequence selected from the group consisting of SEQ ID NO 5, 6, 7, 8, 9, 10, 11, 12, 13, 14, 15, 16, 17, 18, 19, 20, 21, 22, 23, 24, and 2.

In one embodiment, the peptide A' has at least 90%, 95%, 96%, 97%, 98% or 99% sequence identity (% SI) with an amino acid sequence selected from the group consisting of SEQ ID NO 1, 25, 26, 27, 28, 29, 30, 31, 32, 33, 34, 35, 36, 37 and 4.

In one embodiment, the peptide A' has a sequence selected from the group consisting of SEQ ID NO 1, 25, 26, 27, 28, 29, 30, 31, 32, 33, 34, 35, 36, 37 and 4.

In one embodiment, the peptide A' has at least 90%, 95%, 96%, 97%, 98% or 99% sequence identity (% SI) with an amino acid sequence selected from the group consisting of SEQ ID NO 1, 25, 26, 27, 28, 29, 30, and 31.

In one embodiment, the peptide A' has a sequence selected from the group consisting of SEQ ID NO 1, 25, 26, 27, 28, 29, 30, and 31.

In one embodiment, the first peptide is DLTTKLWSSWGYYLGKKARWNLKHPYVQF (SEQ ID NO 1), and the second peptide is chosen from SVPTSVYTLGIKILWSAYKHRKTIEKSFNKGFYH (SEQ ID NO 2), SVPTSVYTLGIKILWSAYKH (SEQ ID NO 5), and YTLGIKILWSAYKH (SEQ ID NO 3).

In one embodiment, the first peptide is DLTTKLWSSWGYYLGKKARWNLKHPYVQF (SEQ ID NO 1), and the second peptide is SVPTSVYTLGIKILWSAYKHRKTIEKSFNKGFYH (SEQ ID NO 2).

In one embodiment, the first peptide is DLTTKLWSSWGYYLGKKARWNLKHPYVQF (SEQ ID NO 1), and the second peptide is SVPTSVYTLGIKILWSAYKH (SEQ ID NO 5).

In one embodiment, the first peptide is DLTTKLWSSWGYYLGKKARWNLKHPYVQF (SEQ ID NO 1), and the second peptide is YTLGIKILWSAYKH (SEQ ID NO 3).

In one embodiment, the first peptide is SVPTSVYTLGIKILWSAYKHRKTIEKSFNKGFYH (SEQ ID NO 2), and the second peptide is chosen from DLTTKLWSSWGYYLGKKARWNL (SEQ ID NO 31).

In one embodiment, the first peptide is SVPTSVYTLGIKILWSAYKHRKTIEKSFNKGFYH (SEQ ID NO 2), and the second peptide is chosen from DLTTKLWSSWGYYLG (SEQ ID NO 4).

Sequence identity (% SI) as described herein may be assessed by any convenient method. Programs that compare and align pairs of sequences, like ALIGN (Myers and Miller, CABIOS, 4:11-17, 1988), FASTA (Pearson, Methods in Enzymology, 183:63-98, 1990) and gapped BLAST (Altschul et al., Nucleic Acids Res., 25:3389-3402, 1997), or BLASTP (Devereux et al., Nucleic Acids Res., 12:387, 1984) can be used for this purpose. If no such resources are at hand, according to one embodiment, sequence identity (%

SI) can be calculated as (% SI)=100%*(Nr of identical residues in pairwise alignment)/(Length of the shortest sequence).

A list of peptide sequences are supplied in table 7.

TABLE 7

SEQUENCE LIST

| PEPTIDE SEQUENCE ID | PEPTIDE SEQUENCE (AA) | Peptide decription |
|---|---|---|
| 1 | DLTTKLWSSWGYYLGKKARWNLKHPYVQF | α1-29 |
| 25 | DLTTKLWSSWGYYLGKKARWNLKHPYVQ | α1-28 |
| 26 | DLTTKLWSSWGYYLGKKARWNLKHPYV | α1-27 |
| 27 | DLTTKLWSSWGYYLGKKARWNLKHPY | α1-26 |
| 28 | DLTTKLWSSWGYYLGKKARWNLKHP | α1-25 |
| 29 | DLTTKLWSSWGYYLGKKARWNLKH | α1-24 |
| 30 | DLTTKLWSSWGYYLGKKARWNLK | α1-23 |
| 31 | DLTTKLWSSWGYYLGKKARWNL | α1-22 |
| 32 | DLTTKLWSSWGYYLGKKARWN | α1-21 |
| 33 | DLTTKLWSSWGYYLGKKARW | α1-20 |
| 34 | DLTTKLWSSWGYYLGKKAR | α1-19 |
| 35 | DLTTKLWSSWGYYLGKKA | α1-18 |
| 36 | DLTTKLWSSWGYYLGKK | α1-17 |
| 37 | DLTTKLWSSWGYYLGK | α1-16 |
| 4 | DLTTKLWSSWGYYLG | α1-15 |
| 5 | SVPTSVYTLGIKILWSAYKH | β1-20 |
| 6 | VPTSVYTLGIKILWSAYKH | β2-20 |
| 7 | PTSVYTLGIKILWSAYKH | β3-20 |
| 8 | TSVYTLGIKILWSAYKH | β4-20 |
| 9 | SVYTLGIKILWSAYKH | β5-20 |
| 10 | VYTLGIKILWSAYKH | β6-20 |
| 3 | YTLGIKILWSAYKH | β7-20 |
| 11 | YTLGIKILWSAYKHR | β7-21 |
| 12 | YTLGIKILWSAYKHRK | β7-22 |
| 13 | YTLGIKILWSAYKHRKT | β7-23 |
| 14 | YTLGIKILWSAYKHRKTI | β7-24 |
| 15 | YTLGIKILWSAYKHRKTIE | β7-25 |
| 16 | YTLGIKILWSAYKHRKTIEK | β7-26 |
| 17 | YTLGIKILWSAYKHRKTIEKS | β7-27 |
| 18 | YTLGIKILWSAYKHRKTIEKSF | β7-28 |
| 19 | YTLGIKILWSAYKHRKTIEKSFN | β7-29 |
| 20 | YTLGIKILWSAYKHRKTIEKSFNK | β7-30 |
| 21 | YTLGIKILWSAYKHRKTIEKSFNKG | β7-31 |
| 22 | YTLGIKILWSAYKHRKTIEKSFNKGF | β7-32 |
| 23 | YTLGIKILWSAYKHRKTIEKSFNKGFY | β7-33 |
| 24 | YTLGIKILWSAYKHRKTIEKSFNKGFYH | β7-34 |
| 2 | SVPTSVYTLGIKILWSAYKHRKTIEKSFNKGFYH | β1-34 |

To verify the synergy effect of peptides of PLNC8 αβ together with antibiotics, antibiotics from the three largest groups of antibiotics were selected and tested; antibiotics that inhibit bacterial cell wall synthesis, antibiotics that inhibit nucleic acid synthesis and antibiotics that inhibit protein synthesis. The combination of antibiotics and PLNC8 αβ provides a powerful synergistic effect, and reduces (up to 100 times) MIC and MBC for antibiotics from the three classes. As can be seen in FIG. 15 teicoplanin, vancomycin, rifampicin, and gentamicin were evaluated. Of these, synergistic effects were (from high to low) rifampicin [100 fold], gentamicin [15-30 fold] teicoplanin [10 fold] and vancomycin [2 fold]. The highest effect was thus shown for a combination of PLNC8 αβ and rifampicin.

In tables 4, 5 and 6, the synergy effects of PLNC8 αβ together with antibiotics selected from a group consisting of gentamicin, rifampicin, ciprofloxacin, teicoplanin, levofloxacin, and meropenem, are shown.

Thus, in one embodiment, the antibiotic is selected from the group consisting of antibiotics that inhibit bacterial cell wall synthesis, antibiotics that inhibit nucleic acid synthesis and antibiotics that inhibit protein synthesis.

In one further embodiment, the antibiotic is selected from a group consisting of gentamicin, rifampicin, ciprofloxacin, teicoplanin, levofloxacin, meropenem and vancomycin.

In one further embodiment, the antibiotic is selected from a group consisting of gentamicin, rifampicin, ciprofloxacin, teicoplanin, levofloxacin, and meropenem.

In one further embodiment, the antibiotic is selected from a group consisting of rifampicin, gentamicin, teicoplanin and vancomycin.

In one further embodiment, the antibiotic is selected from a group consisting of rifampicin, gentamicin, and teicoplanin.

Bacterial biofilms may also seek to combat antibiotics by a reaction with the antimicrobial agent. Similarly, infections are often associated with high proteolytic activity caused by both bacteria and the body's immune system, which means that antimicrobial peptides or proteins may be inactivated.

In the invention, it was hypothesized that the inactivation through proteolytic activity often targets specific sequence motifs. Hypothetically bacteriocin modifications altering the susceptibility to these target attacks could increase the lifetime, and thereby the effect, of the bacteriocin. However, such modifications risk altering the molecular structure of the peptide, which may affect the peptide function.

Figure 4:
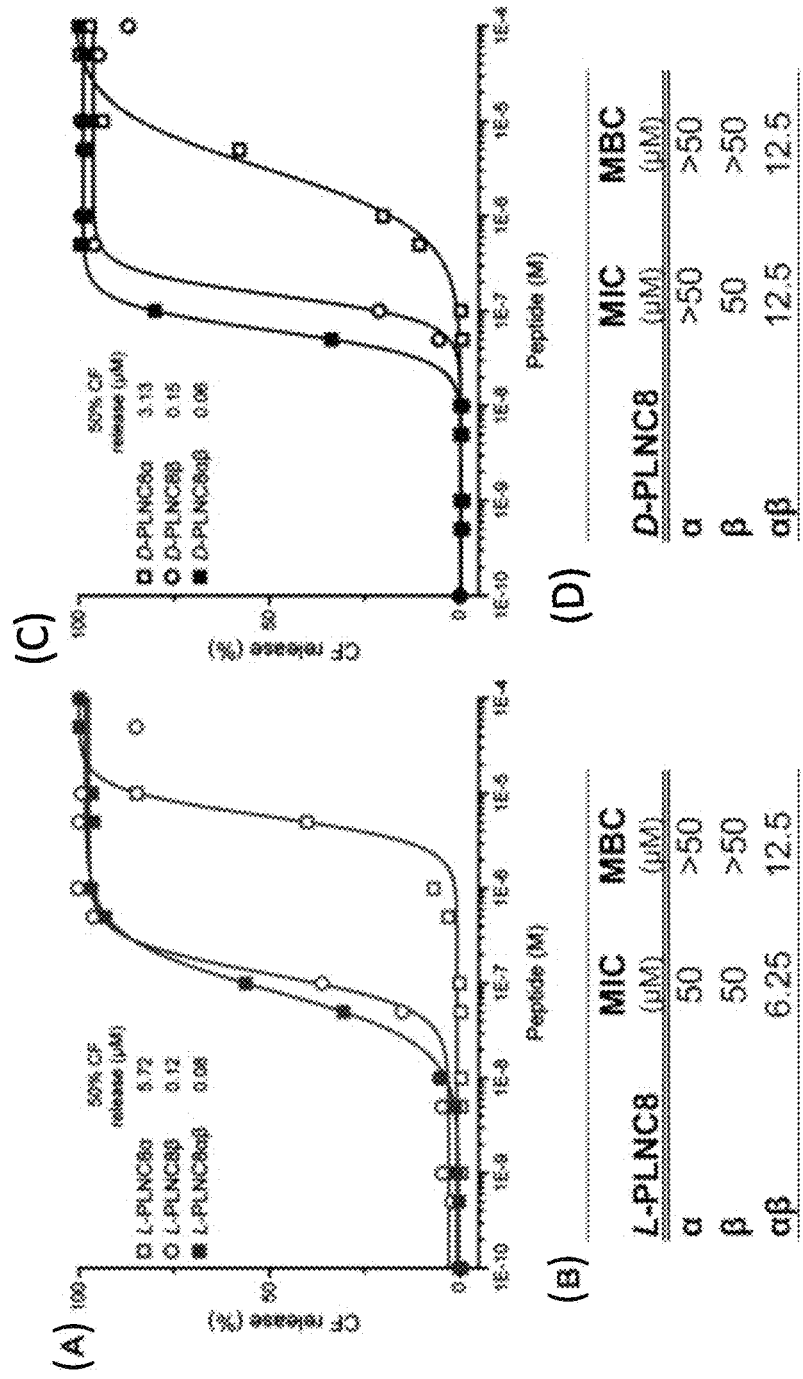
FIGS. 4A-4D. Membrane disrupting and a antimicrobial activity of PLNC8 α and β with L- or D-amino acids. A and C—CF release was recorded after exposure of liposomes with increasing concentrations of L- or D-variants of PLNC8 α, β or αβ (1:1). B and D—S. epidermidis ATCC 12228 was incubated with increasing concentrations of PLNC8 α and β, alone or in combination (1:1), for 20 h. Minimum inhibitory concentration (MIC) and minimum bactericidal concentration (MBC) for PLNC8 α, β and αβ are indicated.
Figure 5:
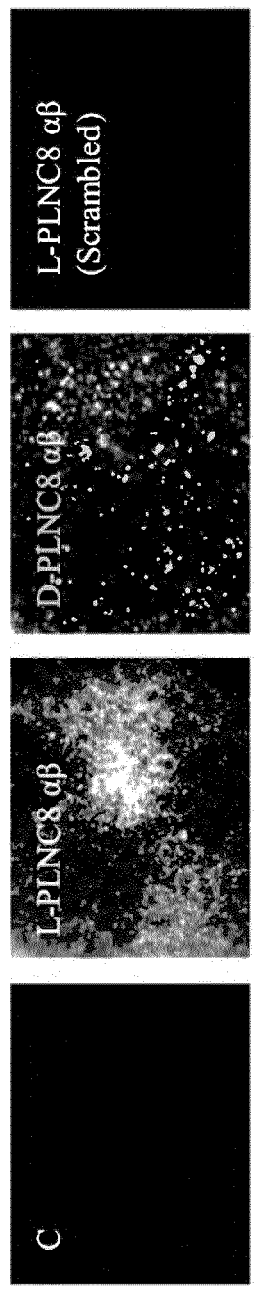
FIG. 5. The L- and D-variant of PLNC8 αβ rapidly permeabilize the plasma membrane of S. epidermidis. The uptake of Sytox Green by S. epidermidis ATCC 12228 after treatment with 5 μM of L-PLNC8 αβ, D-PLNC8 αβ or scrambled-PLNC8 αβ for 2 min, compared to untreated bacteria (C).

Under the hypothesis that a structurally stable structure might be provided if the whole peptide was modified, all L-amino acids of the peptides were replaced by D-amino acids (all alpha amino acids but glycine can exist in either of two enantiomers). It was also hypothesized that this could affect proteolytic cleavage of the peptides and thus increase efficacy. The effects of the L- and D-variants of PLNC8 αβ were tested on both a liposome system (resembling bacteria)

and on *S. epidermidis*. The D-variant of PLNC8 αβ was almost as effective in destroying liposomes and inhibiting/killing *S. epidermidis* as the L-variant (FIG. 4). The perturbation of the plasma membrane of *S. epidermidis* was equally rapid (2 min) for the L- and D-variant, respectively, of PLNC8 αβ (FIG. 5). FIG. 15 shows shown that the synergistic effect is maintained when treating *S. epidermidis* with rifampicin or teicoplanin in the presence of L-PLNC8 αβ or D-PLNC8 αβ (FIG. 15).

Figure 6:
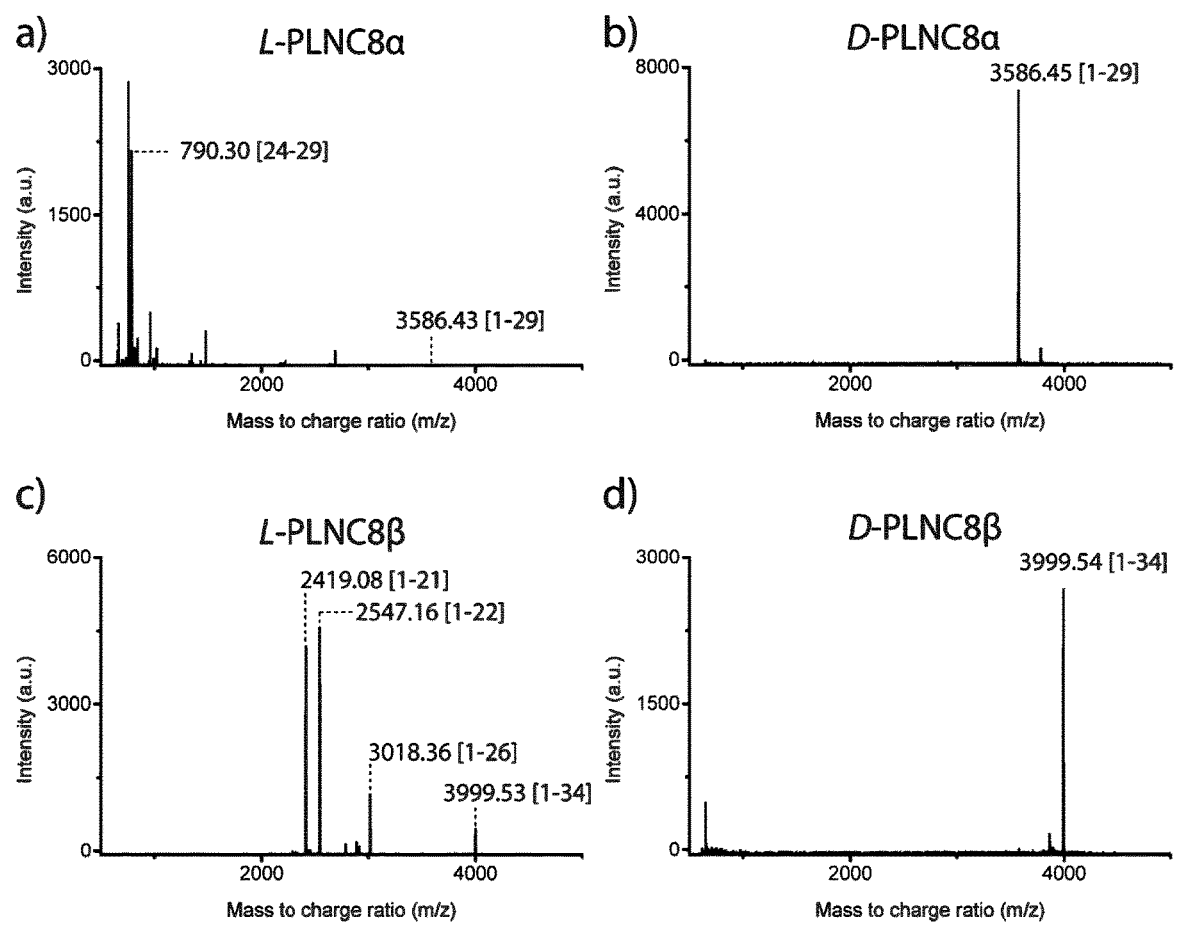
FIG. 6. The D-form of PLNC8 αβ is more stable and less sensitive to proteolytic cleavage. The peptides (100 μM) a) L-PLNC8α b) D-PLNC8α c) L-PLNC8βd) D-PLNC8β were treated with Trypsin (5 μM) in Ammonium Bicarbonate buffer (50 mM) for 16 h at 37° C. before being acified (2.5% TFA), dried, suspended in H2O+0.1% TFA, desalted (ZipTip) and analyzed by MALDI-ToF MS. Number above the peaks indicate molecular weights (Da) and number in brackets sequences of amino acids. Full-length α- and β-peptide, 1-29 and 1-34, respectively.

To analyze whether PLNC8 αβ with D-amino acids is more stable and less sensitive to proteolytic cleavage compared to the L-variant of PLNC8αβ; D-PLNC8α, D-PLNC8β, L-PLNC8α and L-PLNC8β were exposed to trypsin and the presence of proteolytic fragments was analyzed with MALDI-TOF mass spectrometry (FIG. 6). While trypsin generated several fragments of both the α- and β-peptide of L-PLNC8, no obvious fragmentation was observed of the α- and β-peptide of D-PLNC8. Thus, the D-variants are more resistant to trypsin-mediated degradation than the L-variants.

Furthermore, to clarify whether PLNC8 αβ (the L- and D-variant) exerts cytotoxic effects, lysis of erythrocytes isolated from human whole blood was investigated. However, no hemolytic activity was observed (FIG. 7). Thus, in one embodiment, least 90% of the amino acids in the first peptide and/or second peptide are D-amino acid residues.

In FIG. 25, CD measurements of (A) L-PLNC8 αβ and (B) D-PLNC8 αβ with or without liposomes are shown. Bacteriocins are often unstructured in solution but typically adopt a more ordered secondary structure when bound to the bacterial cell membrane as a result of membrane partitioning. However, results indicate that both L and D-PLNC8 αβ has an ordered secondary structure in liposomes.

The advantages of the D-variants are increased stability and less sensitivity to proteolytic cleavage. This results in a longer lifetime of the D-variant peptides and thus prolonged antibacterial effect.

Non-natural or modified amino acids can be introduced that enable convenient coupling chemistries, including click-chemistry approaches. The bacteriocins can also be modified with either N- or C-terminal azide groups to enable copper-free click reaction with e.g. cyclooctyne conjugated polymers. Using biodegradable polymers such as hyaluronic acid (HA), the release rate will be dependent on the hydrolysis rate of the biopolymer backbone and can be tuned to a certain extent by using different polymers. Interestingly, hyaluronidase is expressed by *S. aureus*, as a virulence factor, degrading polysaccharides between cells and thereby enabling spreading of the infection. Thus, if the biodegradable polymer is HA, the release rate of the peptides will increase in the presence of *S. aureus*.

PLNC8αβ is a two peptide bacteriocin, so in order to investigate the role of the PLNC8 α chain and PLNC8 β chain, respectively, in the inhibitory and bactericidal action of the bacteriocin, the effects of different molar ratios between the peptides on *S. epidermidis* were studied. It was found that a molar ratio of 1:1 is most efficient at inhibiting and killing *S. epidermidis* (FIG. 2). However, a ratio of between PLNC8 α chain and PLNC8 β chain of 1:1 to 1:7 also showed a good effect.

Thus, in one embodiment, the first and second peptides are present in a in a molar ratio of from between 5:1 to 1:20, preferably 1:1 to 1:7, most preferably 1:1.

The composition may comprise between 10 nM to 50 μM of the first peptide and/or of the second peptide. As shown in FIG. 15, concentrations within the micromolar range effectively reduce *S. epidermidis* in the presence of an antibiotic.

Thus in one embodiment, the pharmaceutical composition comprises between 10 nM to 50 μM of the first peptide and/or of the second peptide.

As can be seen in FIG. 15, MIC and MBC of rifampicin was lowered more then 100-fold when treating *S. epidermidis* in the presence of L-PLNC8 αβ or D-PLNC8 αβ, resulting in an effective amount already at 0.0019 μg/ml.

Thus, in one embodiment, the pharmaceutical composition comprises the antibiotic in an amount of at between 0.002 μg/ml to 50 μg/ml, such as at least 0.01 μg/ml to 5 μg/ml, such as at least 0.1 μg/ml to 1 μg/ml, such as at least 0.8 μg/ml.

Thus, in one embodiment, the pharmaceutical composition comprises the antibiotic in an amount of at least 0.78 μg/ml of vancomycin, at least 0.097 μg/ml for teicoplanin, at least 0.0019 for rifampicin and at least 0.0097 for gentamicin.

Traditionally, one may think of antibiotics treatment as administered orally. Such treatment may lead to unwanted side effects, such as affecting or even destroying the protective flora or stimulates the development of antibiotics resistance. Such treatment may also lead to changes in the intestinal bacterial composition, which may result in super-infection by fungi and other infective organisms.

PLNC8 αβ together with an antibiotic may beneficially be administered locally, in the form of a solution, cream, a gel or in immobilized form (as described further under coating below).

The formulations may further include a solvent and/or a variety of excipients, for instance to stabilize the peptides and suppress aggregation, such as solubilizers, surfactants, bulking agents (such as carbohydrates), thickeners (such as polymers) to increase solution viscosity, preservatives, vehicles, salts or sugars to stabilize proteins and to obtain physiological tonicity and osmolality and/or buffering agents to control pH.

Thus, in one embodiment, the composition is formulated as a solution, a cream, a gel, or an ointment or formulated in immobilized form as a coating on a device.

In another embodiment, the pharmaceutical composition is for use in the treatment or prophylaxis of a bacterial infection.

In one embodiment, the composition is administered locally on the site of infection, such as topically.

Figure 13:
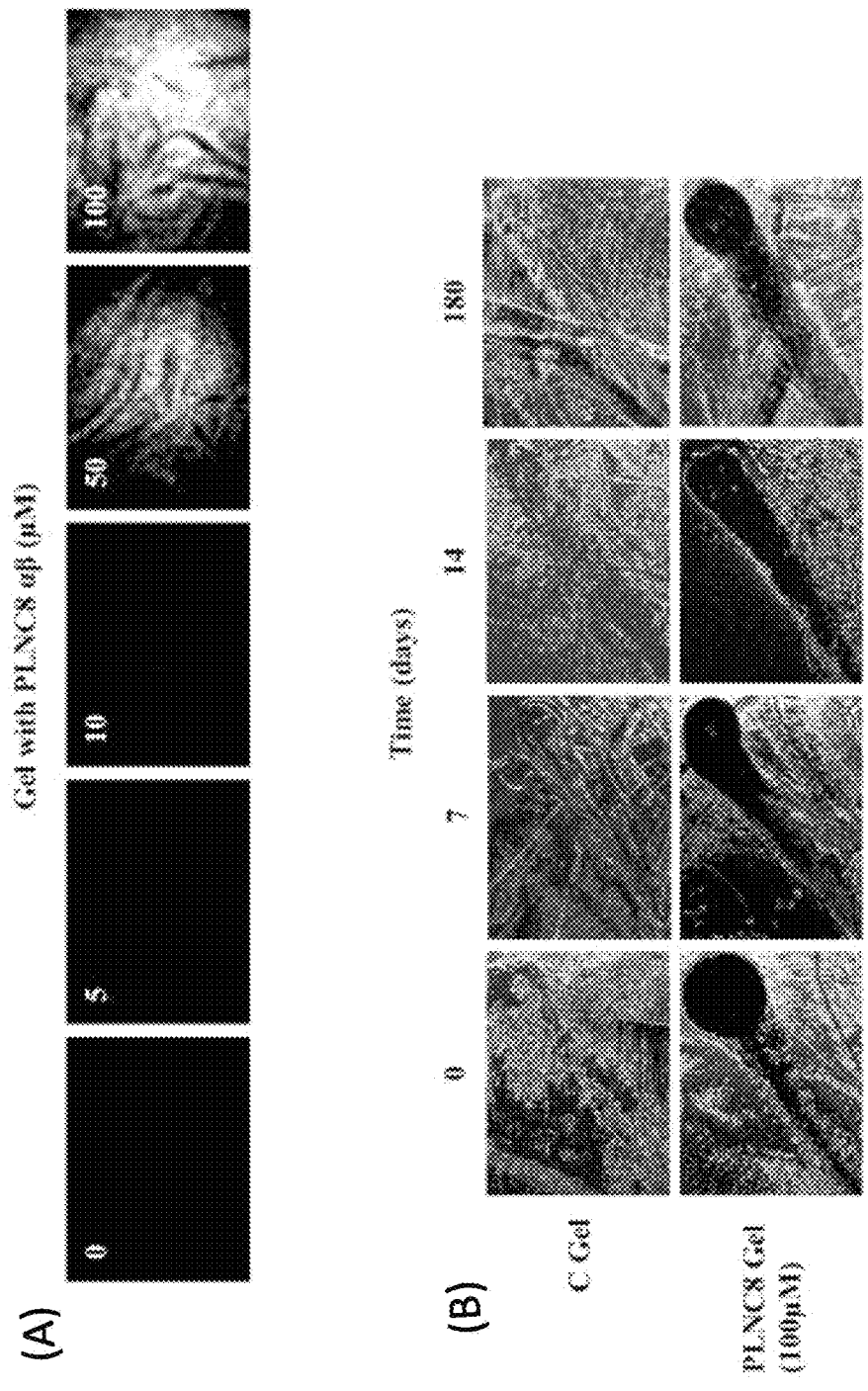
FIGS. 13A-13B. PLNC8 αβ in a formula is effective against S. epidermidis and retains its activity after long-term storage. Bacterial lysis was visualized by studying the uptake of Sytox Green by S. epidermidis ATCC 12228 exposed to a gel containing different concentrations (5-100 μM) of PLNC8 αβ. The activity of the formula with 100 μM PLNC8 αβ was also tested on blood-agar plates with S. epidermidis, at time zero and after long-term storage at 4° C. A gradient of PLNC8 αβ was created by spreading the gel over the agar surface with a plastic loop. Inhibition of bacterial growth is demonstrated by the translucent areas.

To be able to treat local infections, e.g. chronic wounds, PLNC8 αβ may be linked or associated with a supporting material. To test this, PLNC8 αβ was loaded in a formula (gel) consisting of gelatin and glycerol. PLNC8 αβ in the gel rapidly lysed *S. epidermidis* and the PLNC8 αβ-containing gel totally inhibited the growth of the bacteria on agar plates (FIG. 13). The activity of PLNC8 αβ in the gel was stable after long-term storage at 4° C. for at least 180 days.

Thus, in one embodiment, the composition is formulated as a gel, wherein the gel further comprises gelatine and glycerol.

The effect of formulating the composition as a gel is to provide a localized, long-term antibacterial effect.

The results indicate that PLNC8 αβ is effective against many pathogens that are responsible for causing severe hospital- and community acquired infections usually hard to treat (FIGS. 1-3, 11, 14, 17-18, 26-27, and Tables 4-6). Furthermore, PLNC8 αβ has synergistic effects with a wide range of antibiotics and can enhance their effects by 2-130 fold (FIGS. 15-16, 22, 26-27 and Tables 2-7). These results suggest that severe infections caused by antibiotic resistant bacteria may be efficiently treated by applying combination therapy of PLNC8 αβ with low concentrations of antibiotics.

In one embodiment, the bacterial infection is caused by *Staphylococcus* spp (including MRSA, MRSE), *Streptococcus* spp (e.g. *S. mutans, S. constellatus, S. anginosus*), *Enterococcus faecium* (including VRE), *Klebsiella pneumoniae, Acinetobacter baumannii, Pseudomonas aeruginosa, Enterobacter* spp and/or *Escherichia coli*.

In one embodiment, the bacterial infection is caused by *Staphylococcus* spp, *Streptococcus* spp, such as *S. mutans, S. constellatus, S. anginosus*.

In on embodiment, the bacterial infection is caused by *Staphylococcus* spp and/or *Streptococcus* spp.

The bacterial infection may be caused by gram-negative bacteria.

The bacterial infection may be caused by gram-positive bacteria.

The bacterial infection may be caused by *Escherichia coli*.

The bacterial infection may be caused by *Enterococcus* ssp.

The bacterial infection may be caused by *Pseudomonas aeruginosa*.

The bacterial infection may be caused by *Porphyromonas gingivalis*.

Such bacteria are a common cause of hospital-acquired infection (HAI). Among the categories of bacteria most known to infect patients are the ESKAPE pathogens (*Enterococcus faecium, Staphylococcus aureus, Klebsiella pneumoniae, Acinetobacter baumannii, Pseudomonas aeruginosa* and *Enterobacter*), including MRSA (Methicillin-resistant *Staphylococcus aureus*) and VRE (Vancomycin-resistant *Enterococcus*), *Streptococcus* spp and *Escherichia coli*. Thus, one advantage of the present invention is that infections caused by bacteria which are resistant to conventional antibiotics may be treated.

Bacterial infection and inflammation is sometimes linked to implants, caused by the bacterial adherence and colonization in the implant area. Treatment may include removing dead tissue, antibiotics, and improved hygiene. Preventive measures include polish the implant surface, to minimize bacterial adherence, which is a time consuming and costly procedure. Thus, implant coating or treatment with antibacterial material would minimize these incidences and avoid the high-cost of producing a highly polished surface on implant.

Thus, a coating comprising the first and second peptide of the invention (i.e. PLNC8 αβ) together with an antibiotic may be used to impart bacterial resistance to a coating for an implant.

Similarly, such a coating may be used for any medical device, or part of a medical device, where bacterial colonization on the surface should be prevented.

The medical device may also be a band-aid comprising the first and second peptide (i.e. PLNC8 αβ) and antibiotic of the invention. This would help facilitate local administration on a wound or infection site. The bacteriocin and antibiotic may either be tethered to a polymeric scaffold via a flexible linker or physically entrapped in a biopolymeric matrix, its bactericidal property will be retained, or even improved because of its high local concentration In one embodiment, the composition is formulated in immobilized form as a coating on a device, wherein the device is chosen from the group consisting of a wound dressing, an orthopedic implant, a dental implant, a urinary catheter and an urinary stent.

In one embodiment, a pharmaceutical composition is used in coating at least part of a device to limit colonization of bacteria on the surface of the device.

In one further embodiment, the device is a medical device, such as a prosthesis or a wound dressing.

In one further embodiment, the bacteria are *Staphylococcus* spp (including MRSA, MRSE), *Streptococcus* spp (e.g. *S. mutans, S. constellatus, S. anginosus*), *Enterococcus faecium* (including VRE), *Klebsiella pneumoniae, Acinetobacter baumannii, Pseudomonas aeruginosa, Enterobacter* spp and/or *Escherichia coli*.

In one further embodiment, the bacteria are *Staphylococcus* spp and/or *Streptococcus* spp, such as *S. mutans, S. constellatus, S. anginosus*.

Conclusions

Thus, it has been shown that a combination of full length α and truncated or full length β together with antibiotics or full length β and truncated or full length α together with antibiotics or truncated α and truncated length β, have a rapid and direct effect on different pathogens without expressing any toxic effects on surrounding human cells. In addition, it was found that this combination enhances, 2-130 fold, the effect and sensitivity of antibiotics. Substitution of L-amino acids of PLNC8α/β by D-amino acids does not change the anti-bacterial effects of the bacteriocin. However, the D-form of PLNC8α/β is much more stable against proteolytic cleavage and is thus adapted for a therapeutical use in vivo.

The data indicates that the use of a combination of full length α and truncated or full length β together with antibiotics or full length β and truncated or full length α together with antibiotics or truncated α and truncated length β is very well suited for the treatment of infections. This combination can be administered locally in soluble form in gels (ointments, creams) and in immobilized form, e.g. on wound dressings, orthopedic implants, dental implants, urinary catheters and stents, and act antibacterially with no cytotoxic side effects.

Such a combinations provide the following advantages: They act very fast (sec-min); are effective and very potent (nano-micromolar doses); have a wide anti-bacterial spectrum—both against gram-negative and gram-positive bacteria; facilitate and/or enhance the absorption, activity and efficacy of different antibiotics; enable the use of lower doses of antibiotics, which reduce resistance development; enable treatment of complex infections caused by multiple pathogens including multiresistant bacteria, such as MRSA, in suspension or biofilm; low or no effects on normal flora; low or no cytotoxic effects; simple and stable; cheap production.

This means that PLNC8 αβ and antibiotic combination according to the invention is in many respects superior to the various products currently on the market, such as traditional antibiotics, antiseptics and other more unspecific antibacterial substances.

Today there is no method of counteracting and treating chronic infections, for example caused by bacterial biofilms. Treatment of biofilms with antibiotics is very ineffective and costly, and there is also a risk that the protective normal flora is eradicated and that antibiotic resistance develops. Here it has been shown that PLNC8αβ acts synergistically with antibiotics and can effectively attack different pathogens, in suspension or biofilm. Thus it constitutes a more specific, potent and direct anti-bacterial treatment of troublesome infections and associated diseases, and thus lead to less human suffering and greater health-economic effects compared to current forms of treatment.

The invention can be implemented in any suitable form or any combination of forms. Although the present invention has been described above with reference to (a) specific embodiment(s), it is not intended to be limited to the specific form set forth herein. Rather, the invention is limited only by the accompanying claims and, other embodiments than the specific above are equally possible within the scope of these appended claims, e.g. different than those described above.

In the claims, the term "comprises/comprising" does not exclude the presence of other elements or steps. Furthermore, although individually listed, a plurality of means, elements or method steps may be implemented. Additionally, although individual features may be included in different claims, these may advantageously be combined, and the inclusion in different claims does not imply that a combination of features is not feasible and/or advantageous. In addition, singular references do not exclude a plurality. The terms "a", "an", "first", "second" etc do not preclude a plurality.

Experimental Section

Bacterial Culture Conditions

*Staphylococcus aureus* CCUG 35601 (MRSA, Culture Collection, University of Gothenburg) and *Staphylococcus aureus* ATCC 29213 (MSSA, ATCC, Manassas, VA). *Staphylococcus epidermidis* ATCC 12228 (ATCC, Manassas, VA), RP62A, N15 and 10 clinical isolates of *Staphylococcus epidermidis* that have previously been characterized. Isolated *Escherichia coli*, *Enterococcus faecium* (including VRE), *Pseudomonas aeruginosa*, *Klebsiella pneumoniae*, *Enterobacter* spp and *Acinetobacter baumannii* were obtained from Orebro University hospital. Isolated *Streptococcus mutans*, *Streptococcus constellatus* and *Streptococcus anginosus* were obtained from Malmo University. The bacteria were grown on Luria-Bertani (LB) agar plates, supplemented with 5% defibrinated horse blood, and incubated at 37° C. overnight. Single colonies were inoculated into 5 ml of LB broth and incubated on a shaker (300 rpm) at 37° C. overnight. The bacterial concentration was determined by viable count and adjusted to correlate with approximately $10^9$ CFU/ml.

Peptide Synthesis

All chemicals were bought from Sigma Aldrich unless otherwise noted and used without further purification.

PLNC8α (H2N-DLTTKLWSSWGYYLGKKARWNLKHPYVQF-COOH - SEQ ID NO: 1),

PLNC8β (H2N SVPTSVYTLGIKILWSAYKHRKTIEKSFNKGFYH-COOH - SEQ ID NO: 2), scrambled-PLNC8 α (H2N-TWLKYGHGDAKLWSWSKPLNLTFRYQYVK-COOH - SEQ ID NO: 60), scrambled-PLNC8β (H2N-LKLWNTYGTFSRFYTSKSEVKTAHGIKSIHVPYK-COOH - SEQ ID NO: 61), and truncated forms of PLNC8α and PLNC8β were synthesized using conventional Fmoc chemistry on a Quartet automated peptide synthesizer (Protein Technologies, Inc) in a 100 µmol scale. Peptide elongation was performed using a four-fold excesses of amino acid (Iris Biotech GmbH) and activator (TBTU, Iris Biotech GmbH) and using an eightfold excesses of base (DIPEA). Fmoc removal was accomplished by treatment with Piperidine (20% in DMF, v/v). All peptides were cleaved from their solid support using a mixture of TFA, triisoproylsilane and water (95:2.5:2.5, v/v/v) for 2 h before being, filtered, concentrated and precipitated twice in cold diethylether. Crude peptides were purified on a C-18 reversed phase column (Kromatek HiQ-Sil C18HS) attached to a semi preparative HPLC system (Dionex) using an aqueous gradient of acetonitrile (10-46%) containing 0.1% TFA. Mass identity of all peptides was confirmed by MALDI-TOF MS (Applied Biosystems) using α-cyano-4-hydroxycinnamic acid as matrix.

To study the effects and stability of D-forms of PLNC8α and PLNC8β, the L-form of amino acids was substituted with the D-form of amino acids during peptide synthesis. The sensitivity to proteolytic cleavage of D-PLNC8α, D-PLNC8β, L-PLNC8α and L-PLNC8β was analyzed by exposing the peptides to Trypsin for 16 h, whereafter the presence of proteolytic fragments was determined with MALDI-TOF mass spectrometry.

Liposome Preparation

Liposomes were prepared by dry film formation, hydration and finally extrusion through a polycarbonate membrane to form monodisperse large unilamellar vesicles. The lipids 1-palmitoyl-2-oleoyl-sn-glycero-3-phospho-L-serine (POPS) and 1-palmitoyl-2-oleoyl-sn-glycero-3-phosphatidylcholine (POPC) (Avanti Polar Lipids, Alabaster, USA) were mixed at molar ratios 1:99, 5:95 and 10:90 while dissolved in chloroform. A dry lipid film was formed by evaporation of the chloroform by nitrogen flow and overnight lyophilization. The film was hydrated with either 10 mM phosphate buffer (PB) pH 7 or 10 mM phosphate buffer saline (PBS) pH 7, and the solution was vortexed for 1 min and put on a shaker for 1 h before extruded 21 times through a 100 nm pore-sized polycarbonate membrane. For fluorescence leakage assay the lipid film was hydrated with buffer (PBS) containing self-quenching concentration (50 mM) of 5(6)-carboxyfluorescein (CF) (Sigma Aldrich) and liposomes were prepared as described above. Removal of unencapsulated CF was done by gel filtration using a PD-25 column (GE Healthcare, Uppsala, Sweden) and liposomes with encapsulated CF were eluted with PBS.

Fluorescence Leakage Assay

Leakage of the liposome encapsulated fluorophore CF due to additions of the bacteriocins was recorded using a fluorescence plate reader (Infinite 200, Tecan, Austria) where $\lambda_{ex}=485$ nm and $\lambda_{em}=520$ nm. CF was encapsulated at self-quenching concentration, and CF release results in an increased fluorescence signal. Liposomes were diluted to 25 µM (total lipid concentration) in PBS, followed by additions of 0, 0.005, 0.01, 0.02, 0.05, 0.1, 0.2, 0.5, 1 and 2 µM of the L-form or D-form of PLNC8 α and β, separately and combined, and truncated forms of PLNC8 α, separately and combined with PLNC8 β, and truncated forms of PLNC8 β, separately and combined with PLNC8 α. In order to estimate the maximum release from each sample a final addition of 0.5% Triton X-100 was made at the end of all measurements and the total amount of CF (100% release) was estimated after 15 min incubation. The CF release is presented as percentage release for each time interval (measurements taken every minute). The percentage CF release is calculated as $100 \times (F-F_0)/(F_T-F_0)$ where $F_0$ is the initial fluorescence intensity of CF before peptide addition, F is the fluorescence intensity of CF at time point t and $F_T$ is the maximum fluorescence after the addition of Triton X-100. Results are shown in FIG. 4.

Antimicrobial Activity of PLNC8 αβ

The broth microdilution method was used to determine minimal inhibitory concentration (MIC) and minimal bactericidal concentration (MBC). Two-fold serial dilutions of the peptides were used and the final concentrations ranged from 0.097-50 µM. The final concentrations of the antibiotics vancomycin and teicoplanin ranged from 0.097-50 µg/ml, while rifampicin ranged from 0.0019-1 µg/ml and gentamicin 0.0097-5 µg/ml. The effect of bacteriocin-antibiotic combinations was accomplished by using the same concentration series of antibiotics with a constant concentration of PLNC8 αβ (3.1 µM) in all the wells. The MIC was determined visually and spectroscopically (620 nm) as the first concentration that completely inhibited bacterial growth. All concentrations that resulted in complete inhibition of bacterial growth were cultured (10 µl) on blood-agar plates, and the lowest concentration where no growth was observed on agar represented the MBC. All experiments were repeated at least three times.

Microscopy

The fluorescent dye Sytox® Green, which can only cross damaged membranes and fluoresce upon binding to nucleic acids, was used to study the antimicrobial activity of PLNC8 αβ on *S. epidermidis*, *S. aureus* (MSSA, MRSA) and *Streptococcus* spp. The bacteria were washed and resuspended in Krebs-Ringer Glucose buffer (KRG) (120 mM NaCl, 4.9 mM KCl, 1.2 mM $MgSO_4$, 1.7 mM $KH_2PO_4$, 8.3 mM $Na_2HPO_4$, and 10 mM glucose, pH 7.3) and incubated in the presence or absence of different combinations of PLNC8 αβ in 96-well microtiter plates for 2 min. Images were captured with Olympus BX41 at 40× magnification.

Figure 12:
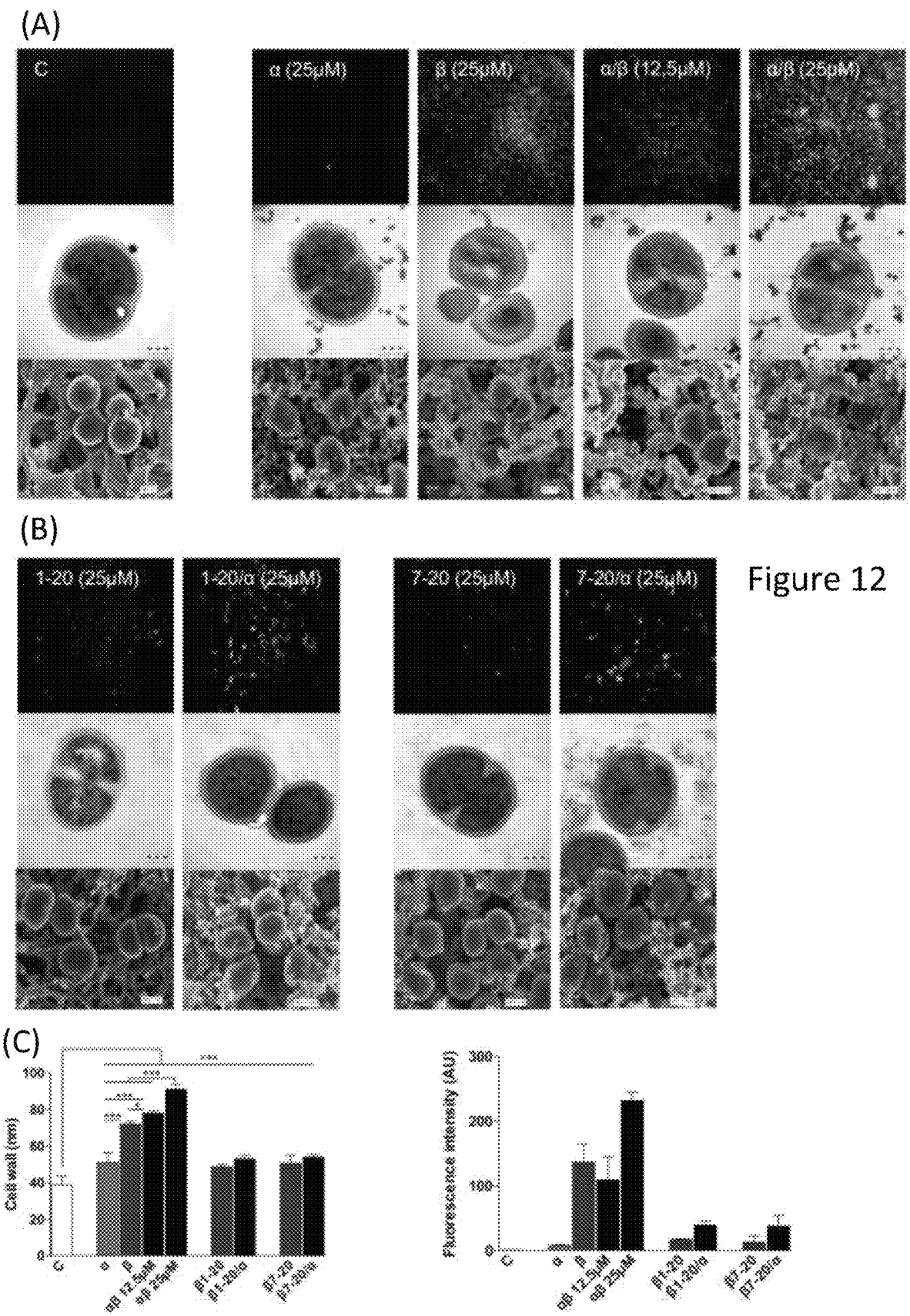
FIGS. 12A-12C. Morphological effects of PLNC8 αβ on S. epidermidis using TEM and SEM. PLNC8 α caused massive bleb formation and PLNC8 β induced bacterial lysis shown by an extracellular release of intracellular content. PLNC8 αβ was most efficient causing complete bacterial lysis. The truncated forms of PLNC8 β, β1-20 and β7-20, induced fragmentation of the bacterial cell wall and in combination with PLNC8 α S. epidermidis went through lysis.

Electron microscopy was used to visualize the damage of bacteria caused by PLNC8 αβ. Briefly, bacteria were pelleted and washed with Krebs-Ringer Glucose buffer (KRG) (120 mM NaCl, 4.9 mM KCl, 1.2 mM $MgSO_4$, 1.7 mM $KH_2PO_4$, 8.3 mM $Na_2HPO_4$, and 10 mM glucose, pH 7.3). The bacteria were then treated with different concentrations of PLNC8 αβ in a ratio of 1:1 for 5 min, followed by fixation in 2.5% glutaraldehyde in 0.1M phosphate buffer, pH 7.3. Critical point drying was applied for specimens for SEM coated with Gold using a Sputter coater. Specimens for TEM were washed in 0.1M phosphate buffer, postfixed in 2% osmium tetroxide in 0.1M phosphate buffer for 2 hours and embedded into LX-112 (Ladd, Burlington, Vermont, USA). Ultrathin sections (approximately 50-60 nm) were cut by a Leica ultracut UCT/Leica EM UC 6 (Leica, Wien, Austria). Sections were contrasted with uranyl acetate followed by lead citrate and examined in a Hitachi HT 7700 (Tokyo, Japan). Digital images were taken by using a Veleta camera (Olympus Soft Imaging Solutions, GmbH, Münster, Germany). Representative images of three independent experiments can be seen in FIG. 12.

Circular Dichroism (CD) Spectroscopy

Bacteriocins are often unstructured in solution but typically adopt a more ordered secondary structure when bound to the bacterial cell membrane as a result of membrane partitioning. Circular dichroism spectroscopy measurements were performed on a Chirascan (Applied Photophysics, United Kingdom) using a 1 mm cuvette at room temperature. A wavelength scan of 195-280 nm was recorded 3 times for each sample, averaged and baseline corrected using PB buffer (pH 7.4, 10 mM). In all samples, the concentration of each peptide was 30 µM, prepared in PB buffer. In experiments with liposomes the final lipid concentration was 660 µM (0.5 mg/ml). To compensate for the different total peptide concentrations used, the averaged data were converted to mean residue ellipticity (MRE).

Proteolytic Degradation

Full length PLNC8 αβ (100 µM) in both L- and D-form was subjected to Trypsin (0.125 mg/ml, ~5 µM) in ammonium bicarbonate buffer (50 mM, pH 8.5) for 16 hours at 37° C. Sample solutions were acidified by adding 2.5% TFA and dried in an exicator at room temperature. Samples were resuspended in MQ-water containing 0.1% TFA, desalted using ZipTip-C18 columns (Millipore) and analyzed using MALDI-ToF MS (UltraflexXtreme, Bruker Daltonics) with α-cyano-4-hydroxycinnamic acid as matrix.

Hemolysis

The hemolytic activity of the peptides was investigated by collecting blood from healthy volunteers in heparinized vacutainers. The blood was centrifuged at 600×g for 5 min and the erythrocyte pellet was washed three times in PBS. The cells were then suspended in PBS and added to 96-well plates (15% erythrocyte suspension/well), containing the peptides with two-fold serial dilution. The plates were incubated for 1 h at 37° C. followed by centrifugation for 5 min at 900×g and measurement of the supernatants at 540 nm. Haemolytic activity (%) was calculated by subtracting the negative control from all values and normalization against the positive control (0.5% Triton X-100), that was set to 100%. All experiments, each in duplicate, were repeated three times.

Aggregation and ATP Release

Aggregation and extracellular release of ATP were used to study the effects of PLNC8 αβ on the bacteria. ATP was registered using a luciferin/luciferase bioluminescence assay (Sigma, St. Louis, Mo, USA) in bacterial suspensions (2.5× $10^8$ CFU/ml). The bacteria were exposed to different concentrations of PLNC8 αβ, and real-time changes in light transmission and bioluminescence were recorded in a Chronolog lumi-aggregometer (Chrono-Log, Haverton, PA, USA) for 30 min. The levels of ATP were calculated based on the bioluminescence signals recorded in response to known concentrations of ATP.

Bacterial Biofilms

*S. epidermidis* RP62A was inoculated into 5 ml of LB broth and incubated on a shaker at 37° C. overnight. The bacterial culture was diluted 1:100 into fresh media and 100 µl of bacterial suspension per well was added in a 96-well microtiter plate and incubated statically at 37° C. for 20 h. The wells were washed three times by submerging the plate into a container with distilled water to remove unattached cells. Fresh LB media was added to each well (100 µl) followed by addition of the peptides in different concentrations. The plate was incubated statically for 1 h. Detached material in the wells were transferred to a new microtiter plate for absorbance measurements at 620 nm. The remaining attached biofilms were stained with 0.1% crystal violet for 15 min before the plate was washed four times in distilled water as mentioned above and allowed to dry at room temperature for 2 h. The crystal violet was solubilized in 30% acetic acid for 15 min and the absorbance quantified at 550 nm. Each experiment, with three replicates, was repeated three times.

Cell Culture Conditions

Human keratinocytes (HaCaT) were cultured in Dulbecco's modified Eagle medium (DMEM, Fisher Scientific, New York, USA) supplemented with 10% FBS (FBS, Invitrogen Ltd, Paisley, UK) incubated in a stable environment at 95% air, 5% $CO_2$ and 37° C. The cells were used at passages 1-20.

HaCaT cells were cultured overnight in a 24-well plate at a seed-count of 2×$10^5$ cells per well. The cells were either treated with PLNC8 αβ (6.25, 12.5 and 25 µM) or MSSA (MOI: 0.1, 1 and 10) alone for 24 h. Co-stimulation was performed by infection of human keratinocytes, in the presence or absence of PLNC8 αβ, for 24 h, or infection of the cells for 1 h followed by addition of different concentrations of PLNC8 αβ for 6 h. Furthermore, infection of keratinocytes, with or without PLNC8 αβ, were monitored in real-time for 72 hours using IncuCyte Live-cell Analysis System. Bacterial load was quantified by measuring the fluorescence of green fluorescent protein (GFP) and cell viability was determined by measuring the fluorescent dye Draq7 that stains nuclei of dead cells.

Enzyme-Linked Immunosorbent Assay (ELISA)

ELISA was performed on supernatants retrieved from human keratinocytes that were exposed to MSSA and PLNC8 αβ. The levels of CXCL8 (Human IL-8 ELISA MAX Deluxe, Nordic Biosite, Sweden) and IL-6 (Human IL-6 ELISA MAX Deluxe, Nordic Biosite, Sweden) were quantified according to the manufacturer's instructions.

Reverse Transcription Quantitative PCR (RT-qPCR)

RT-qPCR was used to determine gene expression levels of a selected number of genes. Briefly, RNA was extracted using GeneJET™ RNA Purification Kit (Fermentas, Sweden) according to the manufacturer's recommendations. Reverse transcription (100 ng RNA/sample) was performed using iScript cDNA Synthesis Kit (Biorad, Sweden). Thermal cycling conditions for SYBR Green (Maxima® SYBR Green/ROX qPCR Master Mix, Fermentas, Sweden) consisted of a denaturation step at 95° C. for 10 min followed by 40 cycles of 95° C. for 15 s and 60° C. for 60 s. Gene expression was analyzed using a 7900 HT real-time PCR instrument (Applied Biosystems). The obtained Ct values were normalized against gapdh. Relative quantification of gene-expression was determined by using the ΔΔCt method. Fold change was generated by using the formula $2^{\Delta\Delta Ct}$.

Porcine Wound Model

Full-thickness wounds measuring 1.5×1.5 cm were created on the dorsum of the pig and covered with sterile wound chambers (S2Medical, Linkoping). Three wounds were created per condition with the following conditions: control (PBS), PLNC8 αβ, MSSA, MSSA/PLNC8 αβ, MSSA/gentamicin and MSSA/gentamicin/PLNC8 αβ. The wounds were either left untreated (sterile PBS), treated with PLNC8 αβ (50 μM) or infected with MSSA ($10^8$ CFU/ml). The pig was returned to the pen and monitored during recovery from anesthesia. After three days, the wounds were washed with sterile PBS and treatment was started (gentamicin 100 μg/ml, PLNC8 αβ 50 μM or a combination of both gentamicin and PLNC8 αβ, 10 μg/ml and 50 μM, respectively). This procedure was repeated every other day for seven days (a total of four doses of treatment of the infected wounds).

LDH Cytotoxicity Assay

Cytotoxicity of HaCaT cells was determined by measuring extracellular lactate dehydrogenase (LDH) activity using LDH cytotoxicity assay. The procedure was performed using Thermo Scientific™ Pierce™ LDH Cytotoxicity Assay Kit according to the manufacturer's instructions. The method relies on the fact that the cytosolic enzyme LDH is released into the surrounding cell culture media if the cell membrane is damaged. Extracellular LDH undergoes an enzymatic reaction, which combined with the assay chemicals culminates in the formation of a red formazan compound which then can be measured in a photo spectrometer at 490 nm. Cytotoxic effects were calculated relative to the untreated cells that were set to 0.

Statistical Analysis

All data were analyzed using GraphPad Prism 5.0 (GraphPad Software, La Jolla, CA, USA). One-way ANOVA with Bonferroni's post hoc test was used for the comparisons between the different treatments. P-values are referred to as *p<0.05; p<0.01; *p<0.001.

Ethics Statement

This work deals with clinical bacterial isolates from human infections. No tissue material or other biological material was stored from the patients, only subcultured bacterial isolates. Swedish law does not require ethical approval for work with bacterial isolates from humans. All information regarding these isolates was anonymized. Animal experiments were performed under the strict regulation of the Ethics Committee for Animal Experimentation, with all the appropriate ethical permissions.

Results

The effects of PLNC8αβ on different strains of *S. aureus* and *S. epidermidis* were studied (Table 1). PLNC8αβ markedly inhibited the growth and the survival of all bacterial strains (FIG. 1).

TABLE 1

| Bacteria | Characteristics |
|---|---|
| S. aureus ATCC 29213 (MSSA) | Methicillin sensitive |
| S. aureus CCUG 35601 (MRSA) | Methicillin resistant |
| S. epidermidis ATCC 12228 | Biofilm negative |
| S. epidermidis RP62A | Biofilm positive |
| S. epidermidis N15 | Isolated from nose of a healthy individual |
| S. epidermidis 117 | Isolated from an infected hip joint prosthesis |

| L-PLNC8 αβ | MIC | MBC |
|---|---|---|
| S. aureus ATCC 29213 (MSSA) | 12.5 | 25 |
| S. aureus CCUG 35601 (MRSA) | 12.5 | 25 |
| S. epidermidis ATCC 12228 | 6.25 | 12.5 |
| S. epidermidis RP62A | 6.25 | 6.25 |
| S. epidermidis N15 | 6.25 | 6.25 |
| S. epidermidis 117 | 12.5 | 12.5 |

In addition, PLNC8 αβ permeabilized and killed *Streptococcus* spp (FIG. 17), *Pseudomonas aeruginosa*, *Escherichia coli* and *Enterococcus faecium* (Table 4-6).

In order to investigate the role of PLNC8 α and PLNC8 β, respectively, in the inhibitory and bactericidal action of the bacteriocin, the effects of different molar ratios between the peptides on *S. epidermidis* were studied. It was found that a PLNC8 α to PLNC8 β molar ratio of 1:1 is most efficient at inhibiting and killing *S. epidermidis* (FIG. 2). However, ratios between 1:1 and 1:7 were also found to be effective.

Figure 3:
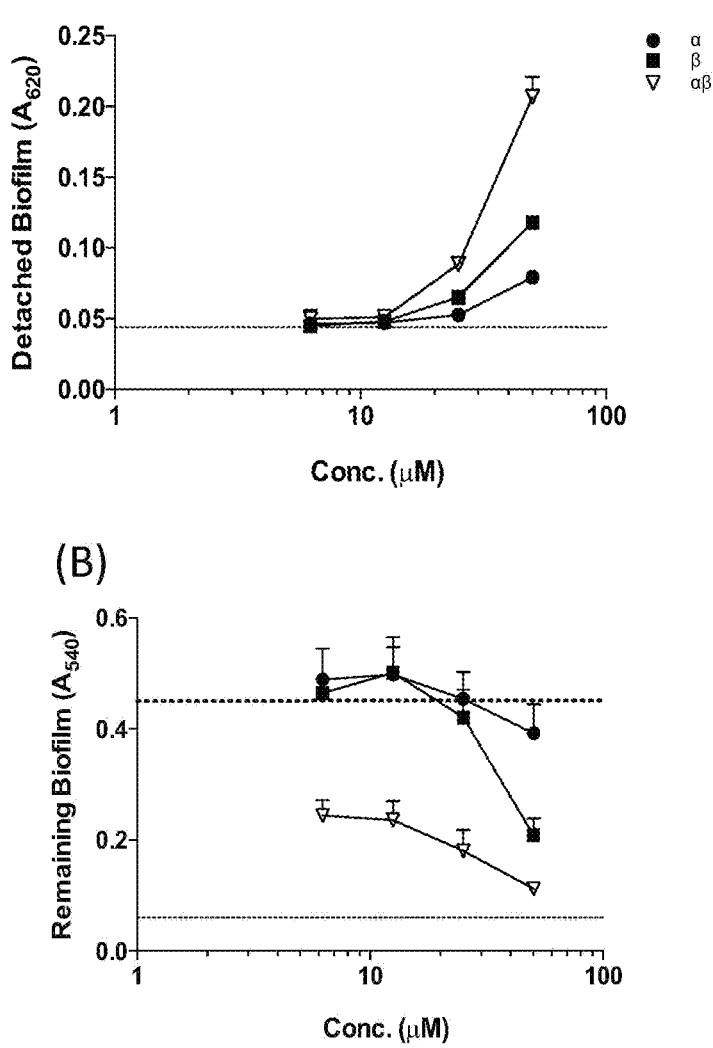
FIGS. 3A and 3B. PLNC8 αβ is effective at disrupting S. epidermidis biofilms. The biofilm positive strain S. epidermidis RP62A was allowed to form biofilms followed by removal of suspended bacteria and then incubation with PLNC8 αβ, PLNC8 α or PLNC8 β for 1 h. A—Absorbance measurement of detached biofilms. B—Crystal violet staining of the remaining attached biofilms. PLNC8 αβ is most efficient and rapid at disrupting biofilms of S. epidermidis.

Since most bacteria grow and are a part of complex biofilms, where they often are more resistant against antibiotic treatment compared to when they exist in a planktonic state, the effects of PLNC8 αβ on biofilms consisting of *S. epidermidis* were tested. It was found that PLNC8 αβ efficiently disrupted the biofilms and killed the bacteria (FIG. 3). Also the α and β peptide of PLNC8 exerted by themselves, although at higher concentrations, disruptive effects on the biofilms.

The antibacterial activity of PLNC8 αβ may in vivo be restricted by proteolytic activity exerted by proteases from both bacteria and human cells. In order to circumvent the problem with a proteolytic cleavage of PLNC8 αβ, the L-form of amino acids, that normally occurs in peptides such as PLNC8 αβ, was substituted with the D-form of amino acids. The effects of the L- and D-variants of PLNC8 αβ were tested on both a liposome system (resembling bacteria) and on *S. epidermidis*. It was found that the D variant of PLNC8 αβ was as effective in destroying liposomes and inhibiting and/or killing S. epidermidis as the L-variant (FIG. 4). Furthermore, the perturbation of the plasma membrane of S. epidermidis was equally rapid (2 min) for the L- and D-variant, respectively, of PLNC8 αβ (FIG. 5).

To analyze whether PLNC8 αβ with D-amino acids is more stable and less sensitive to proteolytic cleavage compared to the L-variant of PLNC8αβ; D-PLNC8α, D-PLNC8β, L-PLNC8α and L-PLNC8β were exposed to trypsin and the presence of proteolytic fragments was analyzed with MALDI-TOF mass spectrometry (FIG. 6). While trypsin generated several fragments of both the α- and β-peptide of L-PLNC8, no obvious fragmentation was observed of the α- and β-peptide of D-PLNC8.

To clarify whether PLNC8 αβ (the L- and D-variant) exerts cytotoxic effects, lysis of erythrocytes isolated from human whole blood was investigated. However, no hemolytic activity was observed (FIG. 7).

Truncated forms of PLNC8 αβ express antibacterial activities similar to the native bacteriocin or are even more effective. Truncated peptides of PLNC8 α and PLNC8 β, respectively, were constructed in sequences of 6-7 amino acids corresponding to the number of amino acids needed for formation of an alpha helix (FIG. 8). The effects of truncated PLNC8 α and PLNC8β were tested on both a liposome system (resembling bacteria) and on S. epidermidis. Disruption of the liposome membranes, revealed by release of (6)-carboxyfluorescein (CF), was obtained with the β-peptides 1-34 (full-length), 7-34, 1-20 and 7-20 (FIG. 9). When combined with PLNC8 α, effects were also obtained with the other truncated peptides, although at higher concentrations.

Interestingly, growth of S. epidermidis was most efficiently inhibited by sequence β1-20 and β7-20, respectively, and these truncated peptides were more effective than the full-length native PLNC8 β (1-34) (FIG. 9).

The peptide β-sequences β7-13 and β14-20 are crucial for the effects of PLNC8 β and are more efficient when combined with β1-6. Thus, the peptide β1-20 is most effective in inhibiting S. epidermidis.

The truncated form 1-22 of the α-peptide and the full-length α-peptide (1-29) disrupted the membrane of the liposomes, revealed by a release of carboxyfluorescein (FIG. 10). However, the different truncated forms of the α-peptide had no significant effects on S. epidermidis. In combination with the β-peptide, α1-22 exerted inhibitory and bactericidal effects (FIG. 10).

To be able to treat local infections, e.g. chronic wounds, PLNC8 αβ was used with a supporting material. PLNC8 αβ was loaded in a formula (gel) consisting of gelatin and glycerol. PLNC8 αβ in the gel rapidly lysed S. epidermidis and the PLNC8 αβ-containing gel totally inhibited the growth of the bacteria on agar plates (FIG. 13). The activity of PLNC8 αβ in the gel was stable after long-term storage at 4° C. for at least 180 days.

Heterogeneous glycopeptide intermediate S. epidermidis (hGISE) is common in prosthetic joint infections (PJIs). Glycopeptide treatment, such as treatment with vancomycin and teicoplanin, is not sufficient in many cases of PJIs. We found that PLNC8 αβ effectively inhibits different strains of S. epidermidis isolated from PJIs, including S. epidermidis (hGISE) (FIG. 14). The D-form of PLNC8 αβ is almost as effective as the L-form in inhibiting strain S. epidermidis 154 (FIG. 15).

Combination therapy is utilized both to prevent the development of antibiotic resistance and to shorten the length of treatment. The effect of the combination of L-PLNC8 αβ or D-PLNC8 αβ with different antibiotics belonging to different classes was also shown: the cell wall synthesis inhibitors vancomycin and teicoplanin, the nucleic acid synthesis inhibitor rifampicin and the protein synthesis inhibitor gentamicin, in the treatment of S. epidermidis.

Both L-PLNC8 αβ and D-PLNC8 αβ decreased MIC and MBC of teicoplanin more then 10-fold against S. epidermidis (FIG. 15). A combination of PLNC8 αβ and rifampicin was even more effective. MIC and MBC of rifampicin was lowered more then 100-fold when treating S. epidermidis in the presence of L-PLNC8 αβ or D-PLNC8 αβ (FIG. 15). Furthermore, L-PLNC8 αβ and D-PLNC8 αβ decreased MIC and MBC of gentamicin more than 30 fold against S. epidermidis. However, L-PLNC8 αβ or D-PLNC8 αβ lowered MIC and MBC of vancomycin 2-fold (FIG. 15).

Figure 16:
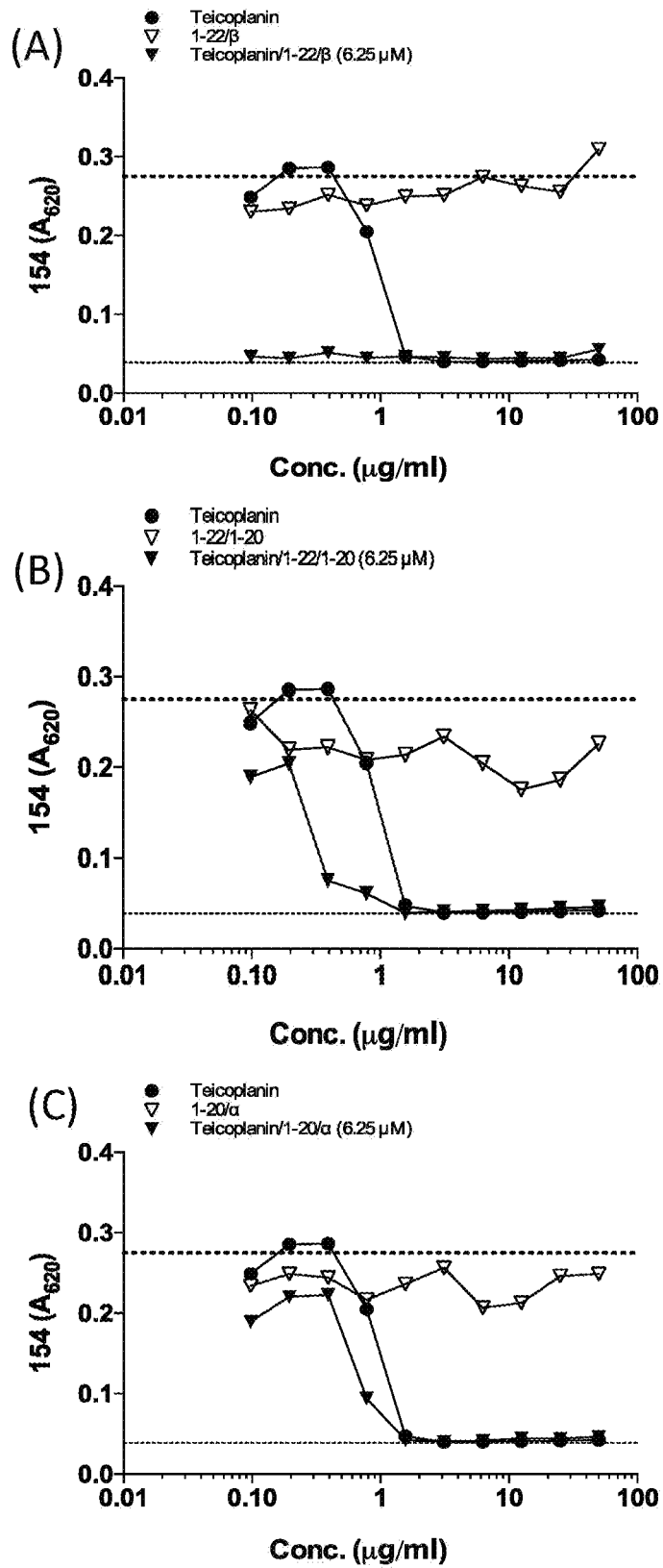
FIGS. 16A-16C. Synergistic antimicrobial effects between teicoplanin and PLNC8 αβ. PLNC8 β and truncated PLNC8 α markedly amplify the inhibitory effects of teicoplanin against S', epidermidis. S. epidermidis (strain 154) was exposed to a serial dilution of teicoplanin or full-length/truncated PLNC8 αβ alone or in their combination (serial dilution of teicoplanin and 6.25 µM full-length/truncated PLNC8 αβ), FIGS. 17A and 17B. PLNC8 αβ markedly permeabilizes and kills different species of Streptococcus. Streptococcus spp (S', mutans (Sm), S. constellatus (Sc) and S', anginosus (Sa)) were treated with 5 µM PLNC8 αβ for 2 min, followed by analysis of uptake of Sytox Green. S. constellatus and S. anginosus were more susceptible to PLNC8 αβ than S. mutans.

A combination of the truncated α-peptide 1-22 with full-length β-peptide decreased MIC and MBC of teicoplanin more then 10-fold against S. epidermidis (FIG. 15), i.e. the same effects as with PLNC8 αβ (FIG. 14). α1-22 and β1-20 lowered MIC and MBC of teicoplanin approximately 4-fold, however, full-length α-peptide and β1-20 had no effects (FIG. 16). As can be seen in table 8 below, the full-length and truncated PLNC8 β and PLNC8 α markedly amplify the inhibitory and bactericidal effects of teicoplanin and rifampicin against S. epidermidis.

TABLE 8

Teicoplanin and rifampicin against S. epidermidis

| Antimicrobial agent | MIC | MBC |
|---|---|---|
| Teicoplanin (μg/ml) | 1.5 | 1.5 |
| Rifampicin (μg/ml) | 0.25 | 0.5 |
| α/β1-20 (μM) | 12.5 | >50 |
| Teicoplanin/α/β1-20 (6.25 μM) | 0.78 | 1.5 |
| Rifampicin/α/β1-20 (6.25 μM) | 0.25 | 0.5 |
| α1-22/β (μM) | 25 | 50 |
| Teicoplanin/α1-22/β (6.25 μM) | <0.097 | 0.39 |
| Rifampicin/α1-22/β (6.25 μM) | 0.063 | 0.25 |
| α1-22/β1-20 (μM) | 12.5 | >50 |
| Teicoplanin/α1-22/β1-20 (6.25 μM) | 0.39 | 1.5 |
| Rifampicin/α1-22/β1-20 (6.25 μM) | 0.25 | 0.5 |

A combination of the truncated α-peptide 1-22 with full-length β-peptide decreased MIC of rifampicin approximately 4-fold against S. epidermidis. α1-22 and β1-20, respectively full-length α-peptide and β1-20, have 2-fold effect (FIG. 16).

PLNC8 αβ rapidly and markedly permeabilized and killed different species of Streptococcus (S. mutans, S. constellatus and S. anginosus). S. constellatus and S. anginosus were more susceptible to PLNC8 αβ than S. mutans (FIG. 17).

PLNC8 αβ dose-dependently and rapidly lysed and killed S. aureus, independent of their resistance to antibiotics (MSSA and MRSA) (FIG. 18).

PLNC8 αβ promoted wound healing in vitro of human keratinocytes. determined using scratch assay. S. aureus increased IL-6 and CXCL8, however, these inflammatory mediators were not altered by PLNC8 αβ (FIG. 19).

PLNC8 αβ antagonized S. aureus-mediated cytotoxicity and inflammatory responses, and promoted cell viability, of human keratinocytes. Secretion of IL-6 and CXCL8 were significantly reduced by the peptides, which was confirmed by gene expression analysis of il-6 and cxcl8. Intracellular signaling events involve c-jun and c-fos, suggesting a role for the transcription factor AP-1 via MAPK (FIG. 20).

PLNC8 αβ promoted wound healing in vitro of human keratinocytes following an infection with *S. aureus* and reduced bacteria-induced secretion of IL-6 and CXCL8 (FIG. 21).

PLNC8αβ inhibited infection and promoted wound healing in vivo, shown in a porcine wound healing model. The peptide, alone or in combination with gentamicin, antagonized the infection and promoted wound healing (FIG. 22).

Figure 24:
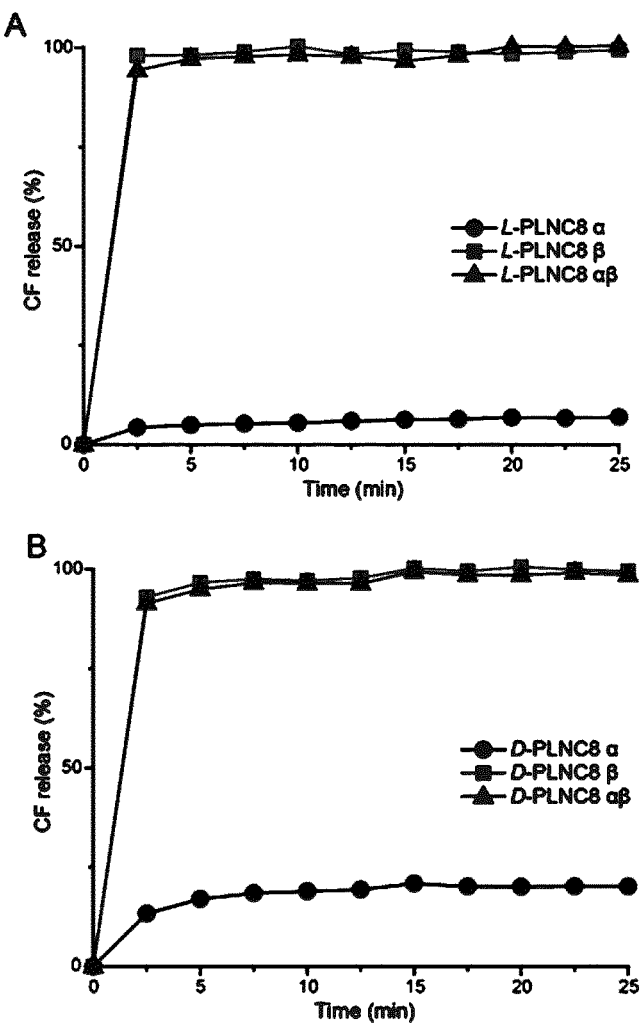

PLNC8 αβ effectively lysesd *S. epidermidis* demonstrated by a dose-dependent release of ATP. (FIG. 23) PLNC8 β and PLNC8 αβ (1:1), but not PLNC8 α, of both the L-form and D-form, caused complete lysis of liposomes after 2 min (FIG. 24)

CD-spectroscopy indicated that both L- and D-PLNC8 αβ has an ordered secondary structure in liposomes (FIG. 25).

IncuCyte live-cell analysis of keratinocytes infected by *S. aureus*, (MOI:1) showed that PLNC8 αβ prevented bacterial growth and protected the cells for up to 32 h. Bacterial growth without peptides reached maximum levels after 8-9 h The combination PLNC8 αβ/gentamicin efficiently eliminated *S. aureus* and prevented an infection, and subsequent cell death, over the entire experimental period (72 h) (FIG. 26).

IncuCyte live-cell analysis of keratinocytes infected by *S. aureus*, (MOI:0.1) showed that PLNC8 αβ prevented bacterial growth and protected the cells for up to 42 h. Bacterial growth without peptides reached maximum levels after 10 h. The combination PLNC8 αβ/gentamicin efficiently eliminated *S. aureus* and prevented an infection, and subsequent cell death, through out the entire experimental period (72 h). (FIG. 27).

PLNC8αβ alone did not affect the growth of *Escherichia coli*, however a sub-MIC concentration of the peptides significantly enhanced the effects of different antibiotics (Table 4).

PLNC8αβ alone was both inhibitory and bactericidal against *Enterococcus faecium*, and addition of sub-MIC concentrations significantly enhanced the effects of different antibiotics (Table 5).

PLNC8αβ alone did not affect the growth of *Pseudomonas aeruginosa*, however, sub-MIC concentration of the peptides enhanced the effects of different antibiotics (Table 6).

REFERENCES

1) Khalaf, H., Nakka S., Sandén, C., Svärd, A., Scherbak, N., Hultenby, K., Aili, D., Bengtsson, T. (2016) Antibacterial effects of *Lactobacillus* and bacteriocin PLNC8 αβ on the periodontal pathogen *Porphyromonas gingivalis*, BMC Microbiology, 18:88.
2) Bengtsson, T., Zhang, B., Selegård, R., Wiman, E., Aili, D., Khalaf, H. (2017). Dual action bacteriocin PLNC8 αβ through inhibition of *Porphyomonas gingivalis* infection and promotion of cell proliferation. Pathogens and Disease, Jun. 12, 2017. Doi: 10.1093/femspd/ftx064

The invention claimed is:

1. A pharmaceutical composition comprising a combination of a) at least one antibiotic and b) a first peptide and a second peptide,
wherein the first peptide is a peptide of the bacteriocin Plantaricin NC8 (PLNC8 αβ) selected from peptide A and peptide B,
wherein
peptide A comprises the amino acid sequence

DLTTKLWSSWGYYLGKKARWNLKHPYVQF (SEQ ID NO: 1)

or the amino acid sequence comprising at least 90%, 95%, 96%, 97%, 98% or 99% sequence identity (% SI) with SEQ ID NO: 1; and
peptide B comprises the amino acid sequence

SVPTSVYTLGIKILWSAYKHRKTIEKSENKGFYH (SEQ ID NO: 2)

or the amino acid sequence comprising at least 90%, 95%, 96%, 97%, 98% or 99% sequence identity (% SI) with SEQ ID NO: 2;
wherein
(i) when the first peptide is peptide A, the second peptide is peptide B' comprising 14 to 34 amino acids in length and comprising the amino acid sequence

YTLGIKILWSAYKH (SEQ ID NO: 3)

or the amino acid sequence comprising at least 90%, 95%, 96%, 97%, 98% or 99% sequence identity (% SI) with SEQ ID NO:3; or
(ii) when the first peptide is peptide B, the second peptide is peptide A' comprising 15 to 29 amino acids in length and comprising the amino acid sequence

DLTTKLWSSWGYYLG (SEQ ID NO: 4)

or the amino acid sequence comprising at least 90%, 95%, 96%, 97%, 98% or 99% sequence identity (% SI) with SEQ ID NO: 4; and
wherein the combination synergistically treats a bacterial infection.

2. The pharmaceutical composition according to claim 1, wherein peptide B' is or comprises at least 90%, 95%, 96%, 97%, 98% or 99% sequence identity (% SI) with the amino acid sequence selected from the group consisting of:

SVPTSVYTLGIKILWSAYKH, (SEQ ID NO: 5)

VPTSVYTLGIKILWSAYKH, (SEQ ID NO: 6)

PTSVYTLGIKILWSAYKH, (SEQ ID NO: 7)

TSVYTLGIKILWSAYKH, (SEQ ID NO: 8)

SVYTLGIKILWSAYKH, (SEQ ID NO: 9)

VYTLGIKILWSAYKH, (SEQ ID NO: 10)

YTLGIKILWSAYKH, (SEQ ID NO: 3)

YTLGIKILWSAYKHR, (SEQ ID NO: 11)

YTLGIKILWSAYKHRK, (SEQ ID NO: 12)

YTLGIKILWSAYKHRKT, (SEQ ID NO: 13)

YTLGIKILWSAYKHRKTI, (SEQ ID NO: 14)

```
                                                     (SEQ ID NO: 15)
YTLGIKILWSAYKHRKTIE, (SEQ ID NO: 16)
YTLGIKILWSAYKHRKTIEK, (SEQ ID NO: 17)
YTLGIKILWSAYKHRKTIEKS, (SEQ ID NO: 18)
YTLGIKILWSAYKHRKTIEKSF, (SEQ ID NO: 19)
YTLGIKILWSAYKHRKTIEKSFN, (SEQ ID NO: 20)
YTLGIKILWSAYKHRKTIEKSFNK, (SEQ ID NO: 21)
YTLGIKILWSAYKHRKTIEKSFNKG, (SEQ ID NO: 22)
YTLGIKILWSAYKHRKTIEKSFNKGF, (SEQ ID NO: 23)
YTLGIKILWSAYKHRKTIEKSFNKGFY, (SEQ ID NO: 24)
YTLGIKILWSAYKHRKTIEKSFNKGFYH, and (SEQ ID NO: 2)
SVPTSVYTLGIKILWSAYKHRKTIEKSENKGFYH.
```

3. The pharmaceutical composition according to claim 1, wherein peptide A' is or comprises at least 90%, 95%, 96%, 97%, 98% or 99% sequence identity (% SI) with the amino acid sequence selected from the group consisting of:

```
                                                     (SEQ ID NO: 1)
DLTTKLWSSWGYYLGKKARWNLKHPYVQF, (SEQ ID NO: 25)
DLTTKLWSSWGYYLGKKARWNLKHPYVQ, (SEQ ID NO: 26)
DLTTKLWSSWGYYLGKKARWNLKHPYV, (SEQ ID NO: 27)
DLTTKLWSSWGYYLGKKARWNLKHPY, (SEQ ID NO: 28)
DLTTKLWSSWGYYLGKKARWNLKHP, (SEQ ID NO: 29)
DLTTKLWSSWGYYLGKKARWNLKH, (SEQ ID NO: 30)
DLTTKLWSSWGYYLGKKARWNLK, (SEQ ID NO: 31)
DLTTKLWSSWGYYLGKKARWNL, (SEQ ID NO: 32)
DLTTKLWSSWGYYLGKKARWN, (SEQ ID NO: 33)
DLTTKLWSSWGYYLGKKARW, (SEQ ID NO: 34)
DLTTKLWSSWGYYLGKKAR, (SEQ ID NO: 35)
DLTTKLWSSWGYYLGKKA, (SEQ ID NO: 36)
DLTTKLWSSWGYYLGKK, (SEQ ID NO: 37)
DLTTKLWSSWGYYLGK, and (SEQ ID NO: 4)
DLTTKLWSSWGYYLG.
```

4. The pharmaceutical composition according to claim 1, wherein the first peptide is peptide A,

```
                                                     (SEQ ID NO: 1)
DLTTKLWSSWGYYLGKKARWNLKHPYVQF,
``` and the second peptide is peptide B' selected from the group consisting of:

```
                                                     (SEQ ID NO: 2)
SVPTSVYTLGIKILWSAYKHRKTIEKSENKGFYH, (SEQ ID NO: 5)
SVPTSVYTLGIKILWSAYKH,
and (SEQ ID NO: 3)
YTLGIKILWSAYKH.
```

5. The pharmaceutical composition according to claim 1, wherein the first peptide is peptide B,

```
                                                     (SEQ ID NO: 2)
SVPTSVYTLGIKILWSAYKHRKTIEKSENKGFYH,
``` and the second peptide is peptide A'

```
                                                     (SEQ ID NO: 31)
DLTTKLWSSWGYYLGKKARWNL.
```

6. The pharmaceutical composition according to claim 1, wherein the antibiotic is selected from the group consisting of antibiotics that inhibit bacterial cell wall synthesis, antibiotics that inhibit nucleic acid synthesis, and antibiotics that inhibit protein synthesis.

7. The pharmaceutical composition according to claim 1, wherein the antibiotic is selected from the group consisting of gentamicin, rifampicin, ciprofloxacin, teicoplanin, levofloxacin, meropenem and vancomycin.

8. The pharmaceutical composition according to claim 1, wherein at least 90% of the amino acids in the first peptide and/or the second peptide are D-amino acid residues.

9. The pharmaceutical composition according to claim 1, wherein the first and second peptides are present in a molar ratio of from between 5:1 to 1:20.

10. The pharmaceutical composition according to claim 1, wherein the pharmaceutical composition comprises between 100 nM to 50 µM of the first peptide and/or 100 nM to 50 µM of the second peptide.

11. The pharmaceutical composition according to claim 1, wherein the pharmaceutical composition comprises the antibiotic in an amount of between 0.002 µg/ml to 50 µg/ml.

12. The pharmaceutical composition according to claim 1, wherein the pharmaceutical composition is a solution, a cream, a gel, an ointment, or an immobilized form as a coating on a device.

13. The pharmaceutical composition according to claim 12, wherein the composition is a gel.

14. The pharmaceutical composition according to claim 1, wherein the first and second peptides are present in a molar ratio of from 1:1 to 1:7.

15. The pharmaceutical composition according to claim 1, wherein the first and second peptides are present in a molar ratio of 1:1.

16. The pharmaceutical composition according to claim 11, wherein the pharmaceutical composition comprises the antibiotic in an amount of 0.01 µg/ml to 5 µg/ml.

17. The pharmaceutical composition according to claim 11, wherein the pharmaceutical composition comprises the antibiotic in an amount of 0.1 µg/ml to 1 µg/ml.

18. The pharmaceutical composition according to claim 11, wherein the pharmaceutical composition comprises the antibiotic in an amount of 0.8 µg/ml to 50 µg/ml.

19. The pharmaceutical composition according to claim 13, wherein the gel comprises gelatine and glycerol.

20. A device having an immobilized coating comprising the pharmaceutical composition according to claim 1, wherein the device is chosen from the group consisting of a wound dressing, an orthopedic implant, a dental implant, a urinary catheter and a urinary stent.

21. A method of treating a bacterial infection in a subject, comprising administering to the subject in need thereof a therapeutically effective amount of the pharmaceutical composition according to claim 12.

22. The method according to claim 21, wherein the bacterial infection is selected from the group consisting of *Staphylococcus* spp, *Streptococcus* spp, *Enterococcus faecium*, *Klebsiella pneumoniae*, *Acinetobacter baumannii*, *Pseudomonas aeruginosa*, *Enterobacter* spp and *Escherichia coli*.

23. The method according to claim 21, wherein the bacterial infection is selected from the group consisting of *Staphylococcus* spp and *Streptococcus* spp.

24. The method according to claim 21, wherein administration of the pharmaceutical composition is at a site of infection.

25. The method according to claim 21, wherein administration of the pharmaceutical composition is topically at a site of infection.

26. The method according to claim 21, wherein the bacterial infection is selected from the group consisting of methicillin-resistant *Staphylococcus aureus*, methicillin-resistant *Staphylococcus epidermidis*, *S. mutans*, *S. constellatus*, *S. anginosus*, and vancomycin-resistant *Enterococcus*.

27. The method according to claim 26, wherein the bacterial infection is selected from the group consisting of *S. mutans*, *S. constellatus*, and *S. anginosus*.

28. A method of treating a bacterial infection in a subject, comprising administering to the subject in need thereof a therapeutically effective amount of the pharmaceutical composition according to claim 1.

29. The method according to claim 28, wherein the bacterial infection is selected from the group consisting of *Staphylococcus* spp, *Streptococcus* spp, *Enterococcus faecium*, *Klebsiella pneumoniae*, *Acinetobacter baumannii*, *Pseudomonas aeruginosa*, *Enterobacter* spp and *Escherichia coli*.

30. The method according to claim 28, wherein the bacterial infection is selected from the group consisting of methicillin-resistant *Staphylococcus aureus*, methicillin-resistant *Staphylococcus epidermidis*, *S. mutans*, *S. constellatus*, *S. anginosus*, and vancomycin-resistant *Enterococcus*.

31. The method according to claim 30, wherein the bacterial infection is selected from the group consisting of *S. mutans*, *S. constellatus*, and *S. anginosus*.

32. A pharmaceutical composition comprising a combination of a) at least one antibiotic selected from the group consisting of gentamicin, ciprofloxacin, levofloxacin, and meropenem, and b) a first peptide and a second peptide, wherein the first peptide is a peptide of the bacteriocin Plantaricin NC8 αβ (PLNC8 αβ) selected from peptide A and peptide B, wherein peptide A comprises the amino acid sequence

```
                                              (SEQ ID NO: 1)
DLTTKLWSSWGYYLGKKARWNLKHPYVQF
``` or the amino acid sequence comprising at least 90%, 95%, 96%, 97%, 98% or 99% sequence identity (% SI) with SEQ ID NO: 1; and peptide B comprises the amino acid sequence

```
                                              (SEQ ID NO: 2)
SVPTSVYTLGIKILWSAYKHRKTIEKSFNKGFYH
``` or the amino acid sequence comprising at least 90%, 95%, 96%, 97%, 98% or 99% sequence identity (% SI) with SEQ ID NO: 2; and wherein (i) when the first peptide is peptide A, the second peptide is peptide B' comprising 14 to 34 amino acids in length and comprising the amino acid sequence YTLGIKILWSAYKH (SEQ ID NO: 3) or the amino acid sequence comprising at least 90%, 95%, 96%, 97%, 98% or 99% sequence identity (% SI) with SEQ ID NO: 3; or (ii) when the first peptide is peptide B, the second peptide is peptide A' comprising 15 to 29 amino acids in length and comprising the amino acid sequence DLTTKLWSSWGYYLG (SEQ ID NO: 4) or the amino acid sequence comprising at least 90%, 95%, 96%, 97%, 98% or 99% sequence identity (% SI) with SEQ ID NO: 4.

33. The pharmaceutical composition according to claim 32, wherein peptide B' is or comprises at least 90%, 95%, 96%, 97%, 98% or 99% sequence identity (% SI) with the amino acid sequence selected from the group consisting of:

```
                          (SEQ ID NO: 5)
SVPTSVYTLGIKILWSAYKH, (SEQ ID NO: 6)
VPTSVYTLGIKILWSAYKH, (SEQ ID NO: 7)
PTSVYTLGIKILWSAYKH, (SEQ ID NO: 8)
TSVYTLGIKILWSAYKH, (SEQ ID NO: 9)
SVYTLGIKILWSAYKH, (SEQ ID NO: 10)
VYTLGIKILWSAYKH, (SEQ ID NO: 3)
YTLGIKILWSAYKH, (SEQ ID NO: 11)
YTLGIKILWSAYKHR,
```

-continued

```
                                          (SEQ ID NO: 12)
YTLGIKILWSAYKHRK, (SEQ ID NO: 13)
YTLGIKILWSAYKHRKT, (SEQ ID NO: 14)
YTLGIKILWSAYKHRKTI, (SEQ ID NO: 15)
YTLGIKILWSAYKHRKTIE, (SEQ ID NO: 16)
YTLGIKILWSAYKHRKTIEK, (SEQ ID NO: 17)
YTLGIKILWSAYKHRKTIEKS, (SEQ ID NO: 18)
YTLGIKILWSAYKHRKTIEKSF, (SEQ ID NO: 19)
YTLGIKILWSAYKHRKTIEKSFN, (SEQ ID NO: 20)
YTLGIKILWSAYKHRKTIEKSFNK, (SEQ ID NO: 21)
YTLGIKILWSAYKHRKTIEKSFNKG, (SEQ ID NO: 22)
YTLGIKILWSAYKHRKTIEKSFNKGF, (SEQ ID NO: 23)
YTLGIKILWSAYKHRKTIEKSFNKGFY, (SEQ ID NO: 24)
YTLGIKILWSAYKHRKTIEKSFNKGFYH, and (SEQ ID NO: 2)
SVPTSVYTLGIKILWSAYKHRKTIEKSFNKGFYH.
```

34. The pharmaceutical composition according to claim 32, wherein peptide A' is or comprises at least 90%, 95%, 96%, 97%, 98% or 99% sequence identity (% SI) with the amino acid sequence selected from the group consisting of:

```
                                          (SEQ ID NO: 1)
DLTTKLWSSWGYYLGKKARWNLKHPYVQF, (SEQ ID NO: 25)
DLTTKLWSSWGYYLGKKARWNLKHPYVQ, (SEQ ID NO: 26)
DLTTKLWSSWGYYLGKKARWNLKHPYV, (SEQ ID NO: 27)
DLTTKLWSSWGYYLGKKARWNLKHPY, (SEQ ID NO: 28)
DLTTKLWSSWGYYLGKKARWNLKHP, (SEQ ID NO: 29)
DLTTKLWSSWGYYLGKKARWNLKH, (SEQ ID NO: 30)
DLTTKLWSSWGYYLGKKARWNLK, (SEQ ID NO: 31)
DLTTK LWSSWGYYLGKKARW NL, (SEQ ID NO: 32)
DLTTKLWSSWGYYLGKKARWN, (SEQ ID NO: 33)
DLTTKLWSSWGYYLGKKARW, (SEQ ID NO: 34)
DLTTKLWSSWGYYLGKKAR, (SEQ ID NO: 35)
DLTTKLWSSWGYYLGKKA, (SEQ ID NO: 36)
DLTTKLWSSWGYYLGKK, (SEQ ID NO: 37)
DLTTKLWSSWGYYLGK, and (SEQ ID NO: 4)
DLTTKLWSSWGYYLG.
```

35. The pharmaceutical composition according to claim 32, wherein the first peptide is peptide A,

```
                                          (SEQ ID NO: 1)
DLTTKLWSSWGYYLGKKARWNLKHPYVQF,
``` and
the second peptide is peptide B' selected from the group consisting of:

```
                                          (SEQ ID NO: 2)
SVPTSVYTLGIKILWSAYKHRKTIEKSFNKGFYH, (SEQ ID NO: 5)
SVPTSVYTLGIKILWSAYKH, and (SEQ ID NO: 3)
YTLGIKILWSAYKH.
```

36. The pharmaceutical composition according to claim 32, wherein
the first peptide is peptide B,

```
                                          (SEQ ID NO: 2)
SVPTSVYTLGIKILWSAYKHRKTIEKSFNKGFYH, and
``` the second peptide is peptide A'

```
                                          (SEQ ID NO: 31)
DLTTKLWSSWGYYLGKKARWNL.
```

37. The pharmaceutical composition according to claim 32, wherein at least 90% of the amino acids in the first peptide and/or the second peptide are D-amino acid residues.

38. The pharmaceutical composition according to claim 32, wherein the first and second peptides are present in a molar ratio of from between 5:1 to 1:20.

39. The pharmaceutical composition according to claim 32, wherein the pharmaceutical composition comprises between 100 nM to 50 μM of the first peptide and/or 100 nM to 50 μM of the second peptide.

40. The pharmaceutical composition according to claim 32, wherein the pharmaceutical composition comprises the antibiotic in an amount of between 0.002 μg/ml to 50 μg/ml.

41. The pharmaceutical composition according to claim 32, wherein the pharmaceutical composition is a solution, a cream, a gel, an ointment, or an immobilized form as a coating on a device.

42. The pharmaceutical composition according to claim 41, wherein the composition is as a gel.

43. The pharmaceutical composition according to claim 32, wherein the first and second peptides are present in a molar ratio of from 1:1 to 1:7.

44. The pharmaceutical composition according to claim 32, wherein the first and second peptides are present in a molar ratio of 1:1.

45. The pharmaceutical composition according to claim 40, wherein the pharmaceutical composition comprises the antibiotic in an amount of 0.01 µg/ml to 5 µg/ml.

46. The pharmaceutical composition according to claim 40, wherein the pharmaceutical composition comprises the antibiotic in an amount of 0.1 µg/ml to 1 µg/ml.

47. The pharmaceutical composition according to claim 40, wherein the pharmaceutical composition comprises the antibiotic in an amount of 0.8 µg/ml to 50 µg/ml.

48. The pharmaceutical composition according to claim 42, wherein the gel comprises gelatine and glycerol.

49. A device having an immobilized coating comprising the pharmaceutical composition according to claim 32, wherein the device is chosen from the group consisting of a wound dressing, an orthopedic implant, a dental implant, a urinary catheter and a urinary stent.

50. A method of treating a bacterial infection in a subject, comprising administering to the subject in need thereof a therapeutically effective amount of the pharmaceutical composition according to claim 41.

51. The method according to claim 50, wherein the bacterial infection is selected from the group consisting of *Staphylococcus* spp, *Streptococcus* spp, *Enterococcus faecium*, *Klebsiella pneumoniae*, *Acinetobacter baumannii*, *Pseudomonas aeruginosa*, *Enterobacter* spp and *Escherichia coli*.

52. The method according to claim 50, wherein the bacterial infection is selected from the group consisting of *Staphylococcus* spp and *Streptococcus* spp.

53. The method according to claim 50, wherein administration of the pharmaceutical composition is at a site of infection.

54. The method according to claim 50, wherein administration of the pharmaceutical composition is topically at a site of infection.

55. The method according to claim 50, wherein the bacterial infection is selected from the group consisting of methicillin-resistant *Staphylococcus aureus*, methicillin-resistant *Staphylococcus epidermidis*, *S. mutans*, *S. constellatus*, *S. anginosus*, and vancomycin-resistant *Enterococcus*.

56. The method according to claim 50, wherein the bacterial infection is selected from the group consisting of *S. mutans*, *S. constellatus*, and *S. anginosus*.

57. A method of treating a bacterial infection in a subject, comprising administering to the subject in need thereof a therapeutically effective amount of the pharmaceutical composition according to claim 32.

58. The method according to claim 57, wherein the bacterial infection is selected from the group consisting of *Staphylococcus* spp, *Streptococcus* spp, *Enterococcus faecium*, *Klebsiella pneumoniae*, *Acinetobacter baumannii*, *Pseudomonas aeruginosa*, *Enterobacter* spp and *Escherichia coli*.

59. The method according to claim 57, wherein the bacterial infection is selected from the group consisting of methicillin-resistant *Staphylococcus aureus*, methicillin-resistant *Staphylococcus epidermidis*, *S. mutans*, *S. constellatus*, *S. anginosus*, and vancomycin-resistant *Enterococcus*.

60. The method according to claim 59, wherein the bacterial infection is selected from the group consisting of *S. mutans*, *S. constellatus*, and *S. anginosus*.

\* \* \* \* \*